US011690818B2

(12) United States Patent
Cui

(10) Patent No.: US 11,690,818 B2
(45) Date of Patent: Jul. 4, 2023

(54) DRUG CONTAINING LIVER TARGETING SPECIFIC LIGAND AND THYROID HORMONE RECEPTOR AGONIST

(71) Applicant: KYLONOVA (XIAMEN) BIOPHARMA CO., LTD., Xiamen (CN)

(72) Inventor: Kunyuan Cui, Xiamen (CN)

(73) Assignee: KYLONOVA (XIAMEN) BIOPHARMA CO., LTD., Xiamen (CN)

( * ) Notice: Subject to any disclaimer, the term of this patent is extended or adjusted under 35 U.S.C. 154(b) by 165 days.

(21) Appl. No.: 17/298,740

(22) PCT Filed: Dec. 2, 2019

(86) PCT No.: PCT/CN2019/122318
§ 371 (c)(1),
(2) Date: Jun. 1, 2021

(87) PCT Pub. No.: WO2020/108657
PCT Pub. Date: Jun. 4, 2020

(65) Prior Publication Data
US 2022/0054443 A1 Feb. 24, 2022

(30) Foreign Application Priority Data
Nov. 30, 2018 (CN) .......................... 201811452803.5

(51) Int. Cl.
A61K 31/198 (2006.01)
A61P 1/16 (2006.01)
A61K 47/54 (2017.01)

(52) U.S. Cl.
CPC ............ A61K 31/198 (2013.01); A61K 47/54 (2017.08); A61K 47/545 (2017.08);
(Continued)

(58) Field of Classification Search
CPC ........ A61K 31/198; A61K 47/549; A61P 1/16
See application file for complete search history.

(56) References Cited

U.S. PATENT DOCUMENTS

2019/0388510 A1* 12/2019 Dimarchi ................ A61P 9/10

FOREIGN PATENT DOCUMENTS

CN 1268517 A 10/2000
CN 107929273 A 4/2018
(Continued)

OTHER PUBLICATIONS

Nair et al. "Multivalent N-acetylgalactosamine-conjugated siRNA localizes in hepatocytes and elicits robust RNAi-Mediated Gene silencing," J. Am. Chem. Soc. 2014, vol. 136, pp. 16958-16961 (Year: 2014).*

(Continued)

Primary Examiner — Shengjun Wang
(74) Attorney, Agent, or Firm — Ladas & Parry LLP

(57) ABSTRACT

Provided is a drug containing a liver targeting specific ligand and a thyroid hormone receptor agonist in its structure, which is a new drug structure formed by linking the liver targeting specific ligand with the thyroid hormone receptor agonist through a branched chain, a linker and a linking chain. Thyroid hormone receptors (TRs) are divided into two subtypes, TR-α and TR-β, wherein, TR-β is mainly expressed in liver, and TR-α is mainly expressed in heart, nervous system, etc. In certain embodiments, it is envisaged that the provided drug has the action of liver targeting, can specifically bring the thyroid hormone receptor agonist into liver, without entering heart and other issues, and may thereby avoid side effects caused by the action of the thyroid hormone receptor agonist on other issues, and maintain its therapeutic efficacy in the treatment of lipid metabolism disorders and related complications.

4 Claims, 11 Drawing Sheets

(52) U.S. Cl.
CPC .......... *A61K 47/548* (2017.08); *A61K 47/549* (2017.08); *A61P 1/16* (2018.01)

(56) References Cited

FOREIGN PATENT DOCUMENTS

| | | | |
|---|---|---|---|
| CN | 109331185 A | 2/2019 | |
| WO | WO-2009073809 A2 * | 6/2009 | ............ A61K 31/70 |
| WO | WO2016149668 A1 | 9/2016 | |

OTHER PUBLICATIONS

International Search Report for International Application PCT/CN2019/122318.
Written Opinion for International Application PCT/CN2019/122318.
CN107929273 A_English Translation.
CN109331185 A_English Translation.
CN1268517 A_English Translation.
Rostislav A. Petrov, et al.: New Small-Molecule Glycoconjugates of Docetaxel and GalNAc for Targeted Delivery to Hepatocellular Carcinoma: Molecular Pharmaceutics: pubs.acs.org/molecularpharmaceutics: dated Dec. 2, 2020.

* cited by examiner

Oil red staining	HE staining

DRUG CONTAINING LIVER TARGETING SPECIFIC LIGAND AND THYROID HORMONE RECEPTOR AGONIST

RELATED APPLICATION

This application is an application under 35 U.S.C. 371 of International Application No. PCT/CN2019/122318 filed on 2 Dec. 2019, which claims priority from Chinese Application 201811452803.5 filed 30 Nov. 2018, the disclosures of which are incorporated in their entirety by reference herein.

TECHNICAL FIELD

The present invention relates to the field of biomedicine, in particular to the field of targeted drugs, and more specifically, to a compound for liver-targeted treatment of liver-derived diseases.

BACKGROUND ART

Hepatic asialoglycoprotein receptor (ASGPR) is a receptor specifically expressed by hepatocytes and a highly efficient endocytic receptor. Since the exposed secondary terminal of various glycoproteins is galactosyl after enzymatic or acidic hydrolysis of sialic acid under in vivo physiological conditions, the sugar specifically bound by ASGPR is galactosyl, and therefore ASGPR is also called galactose specific receptor. Monosaccharide and polysaccharide molecules such as galactose, galactosamine, and N-acetylgalactosamine have high affinity to ASGPR. The main physiological function of ASGPR is to mediate the clearance of asialoglycoprotein, lipoprotein and the like in blood, and is closely related to the occurrence and development of liver diseases such as viral hepatitis, cirrhosis and liver cancer. The discovery of this characteristic of ASGPR plays an important role in diagnosis and treatment of liver diseases (Ashwell G. and Harford J., Carbohydrate specific Receptors of the Liver [J], Ann. Rev. Biochem. 1982 51:531-554).

The feasibility study of monosaccharide or polysaccharide molecules using a receptor on cell membrane to target drug delivery system started in 1971 (Benjamin G. et al., Current Opinion in Drug Discovery & Development 5:279-288; Rogers J. C. et al., Biochem. Biophys. Res. Commun. 45:622-629). The specific binding of ASGPR to galactose molecules have attracted attention in the field of biomedical research and development (Schwartz A. L. et al., J. Biol. Chem. 255: 9033-9036; M. Spiess, Biochemistry 29: 10009-10018). This feature of ASGPR allows targeting delivery of a therapeutic drug having a structure containing galactose or galactosamine or a derivative thereof for liver-derived diseases, ensuring that the drug acts in the liver, and reducing the distribution of the drug in other tissues so as to reduce side effects of the drug on other tissues.

Early researchers have recognized the advantages of ASGPR and have made a lot of efforts. It has been studied to use this feature of ASGPR to target gene fragments to hepatocytes by linking to its specific ligand galactose or acetylgalactosamine (Seymour L., J. Clin. Oncol. 20: 1668-1676). Studies have shown that clustered saccharide residues can have an affinity to ASGPR receptor much higher than that of non-clustered saccharide residues by simultaneously occupying the binding sites of ASGPR receptor. Trisaccharide residues have an affinity 50 to 100 times higher than that of monosaccharide residues. The affinity order is tetrasaccharide residue>trisaccharide residue>>disaccharide residue>>monosaccharide residue. Compared with trisaccharide residues, the affinity to ASGPR of tetrasaccharide residues is not significantly improved, which may be due to the fact that the binding of trisaccharide residues to the receptor is saturated. This phenomenon is called "cluster effect". Among early researches, Merwin et al. designed and synthesized a vector system modified with three galactosamines (Merwin J. R. et al., Bioconjug. Chem. 1994 5(6):612-620). It has been demonstrated that, in animals, this system can mediate plasmid DNA rapidly and massively enriching into mouse liver, and successfully express luciferase. In later studies, galactosamine was applied in administration of antisense nucleotides (oligodeoxynucleosidemethylphosphonate, Oligo-MP) (Hangeland J. J. et al., Bioconjug. Chem. 1995 6(6):695-701), antisense peptide nucleic acid (asPNA) (Biessen E. A., Bioconjug. Chem. 2002 13(2):295-302), etc., and desired therapeutic effects were achieved. US Alnylam Pharmaceuticals Inc. has made a breakthrough in use of this characteristic drug delivery mechanism of ASGPR, and its product ALN-TTRSC for treatment of amyloidosis has been in phase n clinical stage.

Through using the above-mentioned characteristics of ASGPR, the present invention provides a compound containing a specific ligand for ASGPR and a thyroid hormone receptor agonist in the structure, wherein a liver targeting specific ligand and a thyroid hormone receptor agonist is connected through a branched chain, a linker and a linking chain to form a new compound structure.

Thyroid hormone receptors (TRs) are divided into two subtypes, TR-α and TR-β, which are nuclear hormone receptors of two genes (Lazar M., Endocr. Rev. 14: 348-399). These two receptors mediate different physiological effects due to difference in tissue expression abundance, that is, these two receptors have different tissue specificities (Forrest D. et al., Thyroid 10:41-31). Among them, TR-α is a main receptor that regulates heart rate (HR) (Johansson C. et al., Am. J. Physiol. 275: R640-R646; Gloss B. et al., Endocrinology 142: 544-551), and TR-β is mainly expressed in the liver. TR-β agonists (thyroid hormone analogs, a class of new compounds based on structural modification of thyroid hormones) have always been an important development area for new drugs for treatment of non-alcoholic fatty liver diseases (NAFLD), and some new drugs have been in clinical studies. For example, the TRs selective agonist GC-1 (Sobetirome, as a TRs selective agonist, is a non-alcoholic fatty liver drug that was give high hope, and was developed by Bristol-Myers Squibb Co.) can effectively reduce plasma cholesterol level and minimize the effect in heart of mice, but GC-1 only showed a relatively low entry into the heart, is not the expected specific TR-β agonist and highly selective agonist (Trost S et al., Endocrinology 141: 3057-3064), and is finally terminated in clinical phase I. Another TRs selective agonist KB211S (the generic name is Eprotrome, developed by Karo Bio, USA) was terminated in clinical phase III due to specific pharmacological reasons. A TR-β agonist with clinical value for treatment of liver-derived diseases must have a wide therapeutic dose range without tachycardia and side effects of other tissues, have high selectivity for lowering total cholesterol (TC), and be safe and effective. However, the TRs selective agonists currently under development cannot fully meet these conditions. Non-alcoholic fatty liver disease is caused by factors other than alcohol and other definite liver-damaging factors. It is a metabolic disease related to obesity, hypercholesterolemia and diabetes, including simple fatty liver disease and steatohepatitis (NASH) and liver cirrhosis derived thereof. Current treatment methods are mainly based on changes in lifestyle, including diet and exercise (Mendez-Sanchez N., et al., Liver Int. 2007 27:1157-1165; Oh M. K., et al., Aliment Pharmacol. Ther. 28:503-522), and there are no approved therapeutic drugs.

Physiological thyroid hormones [thyroxine (T4) and 3,3', 5-triiodo-L-thyroxine (T3)] regulate glucose and lipid metabolism through a variety of ways, and play an important physiological role in lipid metabolism by interacting with specific hormone receptors TR-α and TR-β that are widely distributed throughout the body. TR-β is mainly expressed in the liver, and has important effects on lipid metabolism, including lowering low-density lipoprotein (LDL) cholesterol and reducing systemic obesity and body weight (Pramfalk C., et al., Biochim. Biophys. Acta 1812:929-937), and can reduce lipid content by increasing lipid metabolism rate in the liver. A study by Perra A. et al. showed that T3 can (Perra A. et al., FASEB J. 22:2981-2989), which indicates an extraordinary potential therapeutic effect of T3 in non-alcoholic fatty liver.

However, excessive thyroid hormones are prone to side effects, especially adverse reactions to the heart (including tachycardia and sudden death), bones and muscles (Braverman L. E., et al., editors. Lippincott: The Thyroid 2000: 515-517). Due to these adverse effects, it is restricted that thyroid hormones are further applied in the treatment of non-alcoholic fatty liver. If the side effects of thyroid hormones on the heart and other organs may be eliminated or reduced, a predictable therapeutic effect may be achieved. It is an innovation in development of new drugs for treatment of NAFLD/NASH to bring a thyroid hormone or a thyroxine-like compound, such as GC-1 and KB2115, into the liver by liver-targeted delivery so as to reduce or avoid entering other tissues outside the liver. This invention has clinical and practical economic significance.

Therefore, there is a need to prepare a new structural compound directly targeting liver cells by using thyroid hormones T3, T4 and their metabolites, or thyroid hormone analogs for liver-derived diseases that cannot be used as medicine due to side effects as a part of the compound, so as to reduce side effects of the original drug on other tissues. This will not only innovate research and development ideas, but also improve the current status of no clinically effective drugs for non-alcoholic fatty liver.

MODE FOR THE INVENTION

The present invention allows targeted delivery of a compound or candidate compound for liver-derived diseases that cannot be used as medicine due to side effects into the liver to treat corresponding diseases, by using the above-mentioned characteristics of the asialoglycoprotein receptor. More precisely, the present invention prepares a compound by using the high affinity of the asialoglycoprotein receptor and its ligand, so that it can specifically bring the therapeutic compound into the liver cells with little or no entry into tissue cells outside the liver, thereby reducing the side effects of the therapeutic compound on the tissue cells outside the liver.

The present invention prepares a drug containing a liver targeting specific ligand and a thyroid hormone receptor agonist in the structure.

The liver targeting specific ligand may be selected from galactose and its derivatives, preferably galactosamine, acetylgalactosamine or trivalent acetylgalactosamine.

The liver targeting specific ligand X in the drug is connected to the thyroid hormone receptor agonist T sequentially through a branched chain L containing a structure for stabilizing steric hindrance, a linker B and a linking chain D. The drug is represented by Formula (I) of

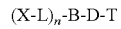

wherein n is a positive integer of 1 to 15.

The linker B in Formula (I) is branched multiple times, and the resulting branches are used to connect n (X-L)s and one (D-T) in Formula (I).

In some preferred embodiments, when n is greater than 1, each X may have the same or different structure.

In some preferred embodiments, when n is greater than 1, each L may have the same or different structure.

When n=1, Formula (I) is X-L-B-D-T.

When n=2, 3, 4, 5 or 6, Formula (I) may have a structure as shown in sequence below:

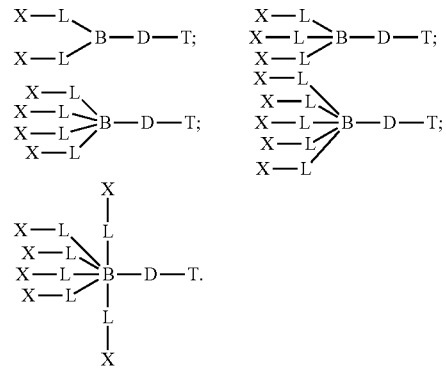

The liver targeting specific ligand is one or more selected from the following structures: a polysaccharide, a polysaccharide derivative, a monosaccharide and a monosaccharide derivative.

The monosaccharide is one or more selected from the following structures: mannose, galactose, D-arabinose, glucose, fructose, xylose, glucosamine, ribose.

The mannose is one or more selected from the following structures: D-mannopyranose, L-mannopyranose, α-D-mannofuranose, β-D-mannofuranose, α-D-mannopyranose, β-D-mannopyranose.

The galactose is one or more selected from the following structures: L-galactose, D-galactose, α-D-galactopyranose, β-D-galactopyranose, α-D-galactofuranose, β-D-galactofuranose The glucose is one or more selected from the following structures: D-glucose, L-glucose, α-D-glucopyranose, β-D-glucopyranose, α-D-glucofuranose, β-D-glucofuranose.

The fructose is one or more selected from the following structures: α-D-fructofuranose, α-D-fructopyranose.

The xylose is one or more selected from the following structures: D-xylofuranose, L-xylofuranose.

The ribose is one or more selected from the following structures: ribose, D-ribose, L-ribose.

The monosaccharide derivative is one or more selected from the following structures: mannose derivatives, galactose derivatives, glucose derivatives, ribose derivatives and other derivatives.

The mannose derivative is 4,6-dideoxy-4-carboxamido-2,3-di-O-methyl-D-mannopyranose.

The galactose derivative is one or more selected from the following structures: α-D-galactosamine, N-acetylgalactosamine, 4-thio-β-D-galactopyranose.

The glucose derivative is one or more selected from the following structures: 2-amino-3-O—[(R)-1-carboxyethyl]-

2-deoxy-β-D-glucopyranose, 2-deoxy-2-methylamino-L-glucopyranose, 2-deoxy-2-sulfoamido-D-glucopyranose, 5-thio-β-D-glucopyranose, methyl 2,3,4-tri-O-acetyl-1-thio-6-O-trityl-α-D-glucopyranoside.

The ribose derivative is one or more selected from the following structures: D-4-thioribose, L-4-thioribose.

The other derivative is one or more selected from the following structures: 2,5-anhydro-D-allosenitrile, sialic acid, N-glycolyl-α-neuraminic acid, 3,4,6,7-tetra-O-acetyl-2-deoxy-1,5-dithio-α-D-glucopyranoheptanoside ethyl ester.

The liver targeting specific ligand is represented by the structural formula (II) of

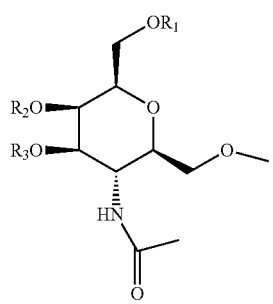

wherein R$_1$, R$_2$ and R$_3$ are hydrogen or a hydroxyl protecting group.

The hydroxy protecting group is selected from the following structures: an acyl and a silyl.

Preferably, the hydroxy protecting group is selected from the following structures: acetyl, benzoyl, phenoxyacetyl, pivaloyl, isobutyryl, tert-butyldimethylsilyl, tert-butyldiphenylsilyl, triisopropylsilyl and isopropyldimethylsilyl.

In some preferred embodiments, the liver targeting specific ligand is one or more selected from the following structures;

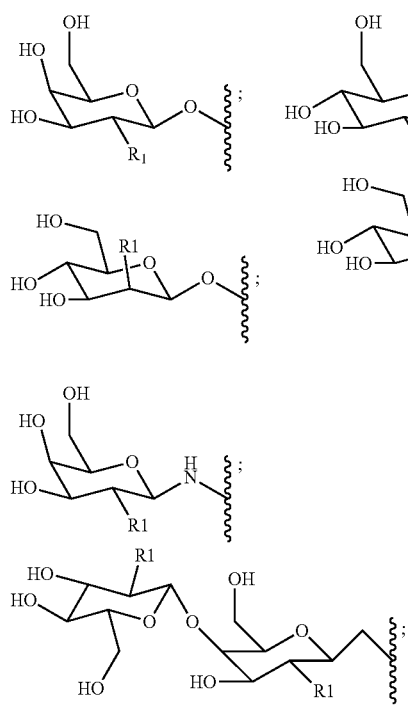

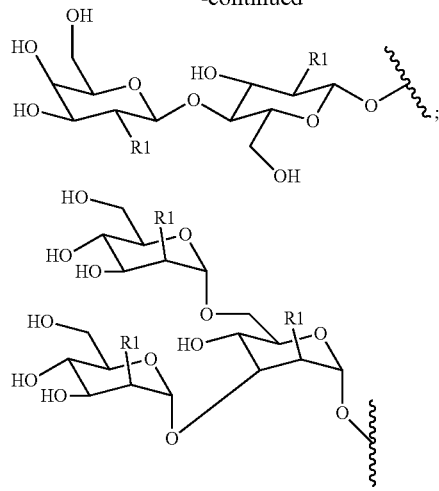

wherein, R1 is one or two selected from OH and NHC(O)CH$_3$.

In some preferred embodiments, the liver targeting specific ligand is acetylgalactosamine.

The branched chain L is one or more selected from the following structures:

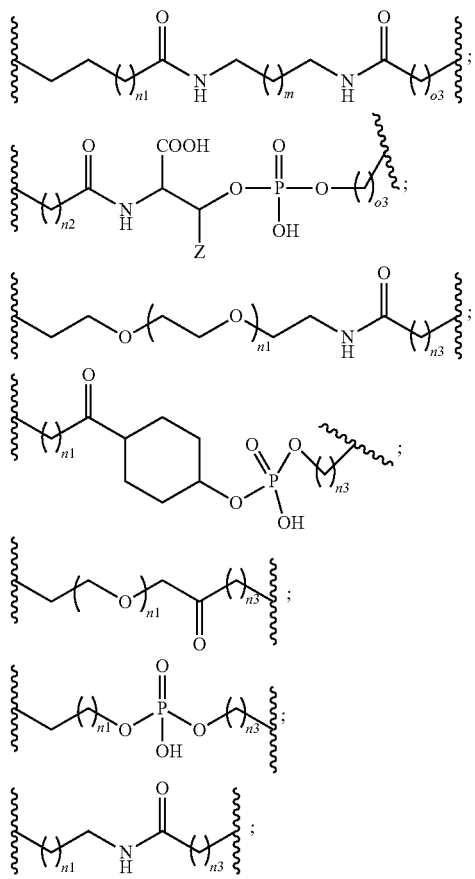

wherein, in the formulae, n1 is a positive integer of 1 to 10, m is a positive integer of 1 to 5, n2 is an integer of 0 to 20, n3 is a positive integer of 0 to 12, Z is H or CH$_3$; and the branched chain L containing a structure for stabilizing steric hindrance has a left end connected to the liver targeting specific ligand X, and a right end connected to the left end of the linker B.

The linker B is selected from the following structures:

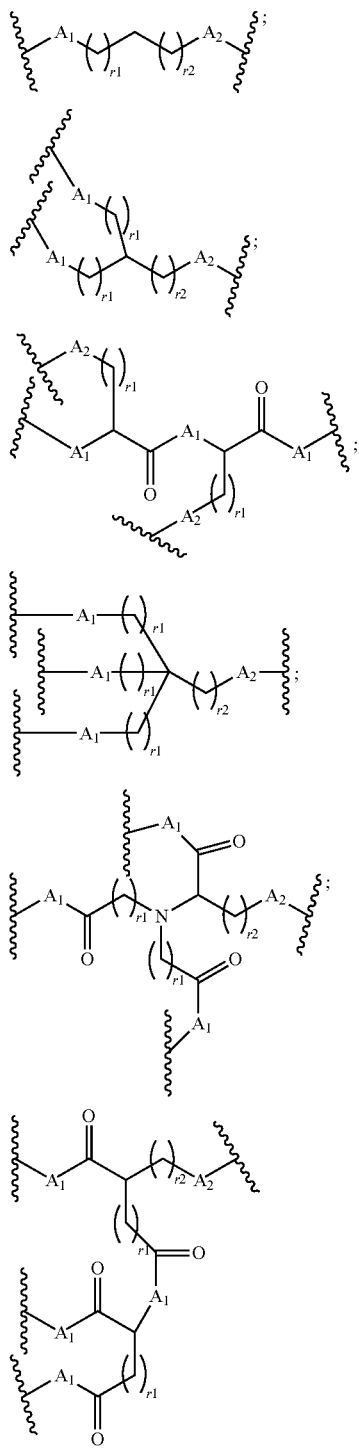

The linker B is selected from the following structures:

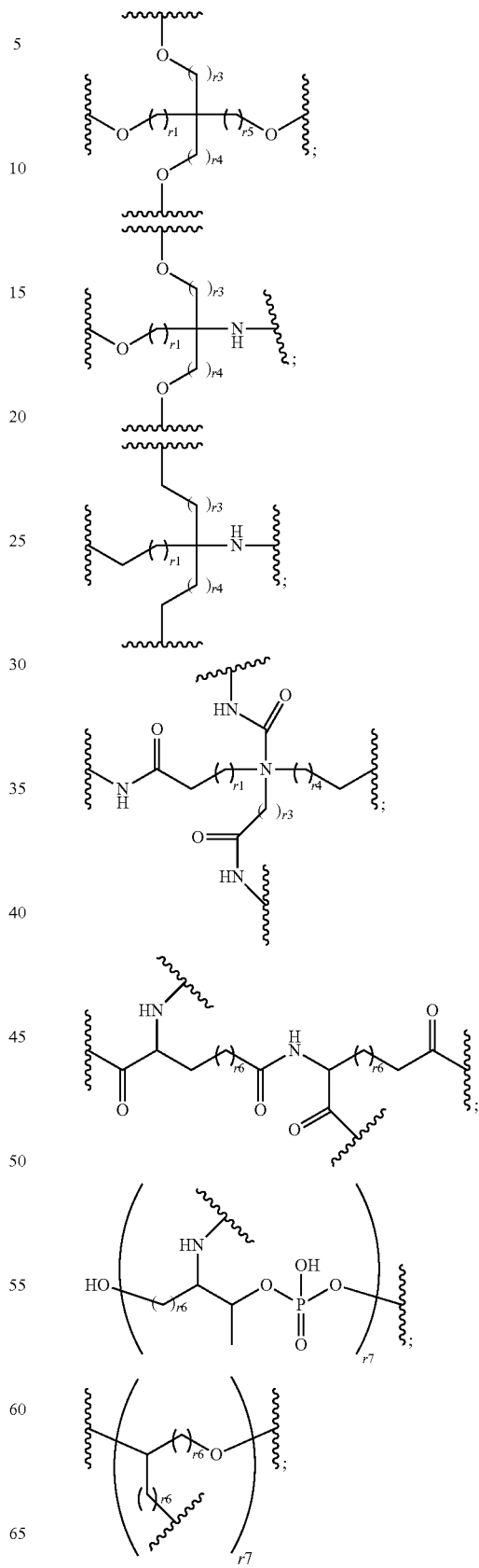

wherein, $A_1$ is C, O, S or NH, r1 is a positive integer of 1 to 15; $A_2$ is selected from C1-C10 linear alkanes, a fragment with amino, amido, phosphoryl, thiophosphoryl, oxygen, sulfur or a cyclic compound, r2 is an integer of 0 to 15.

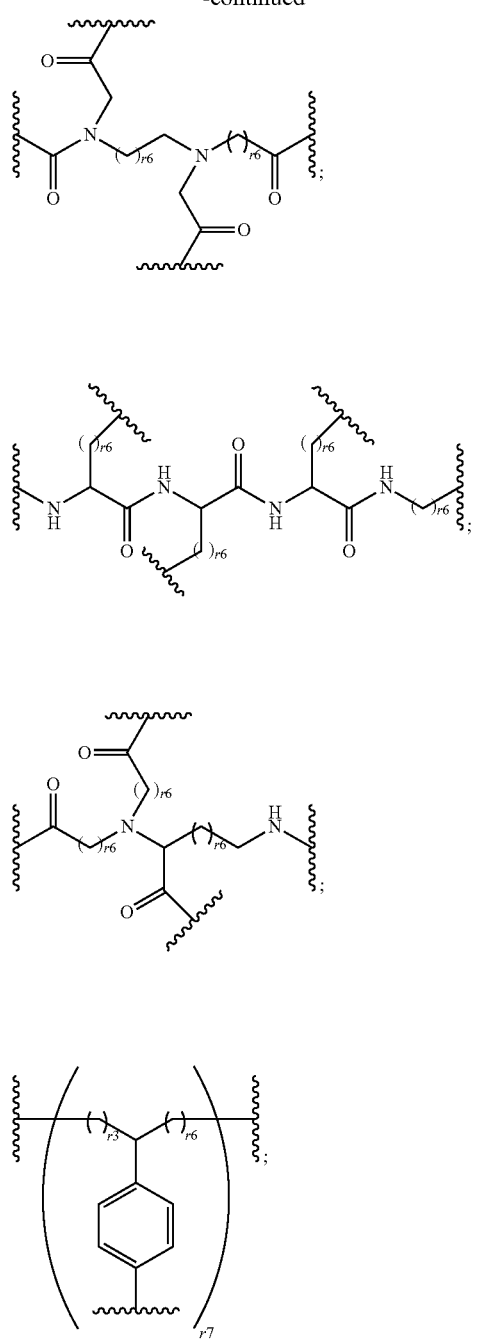
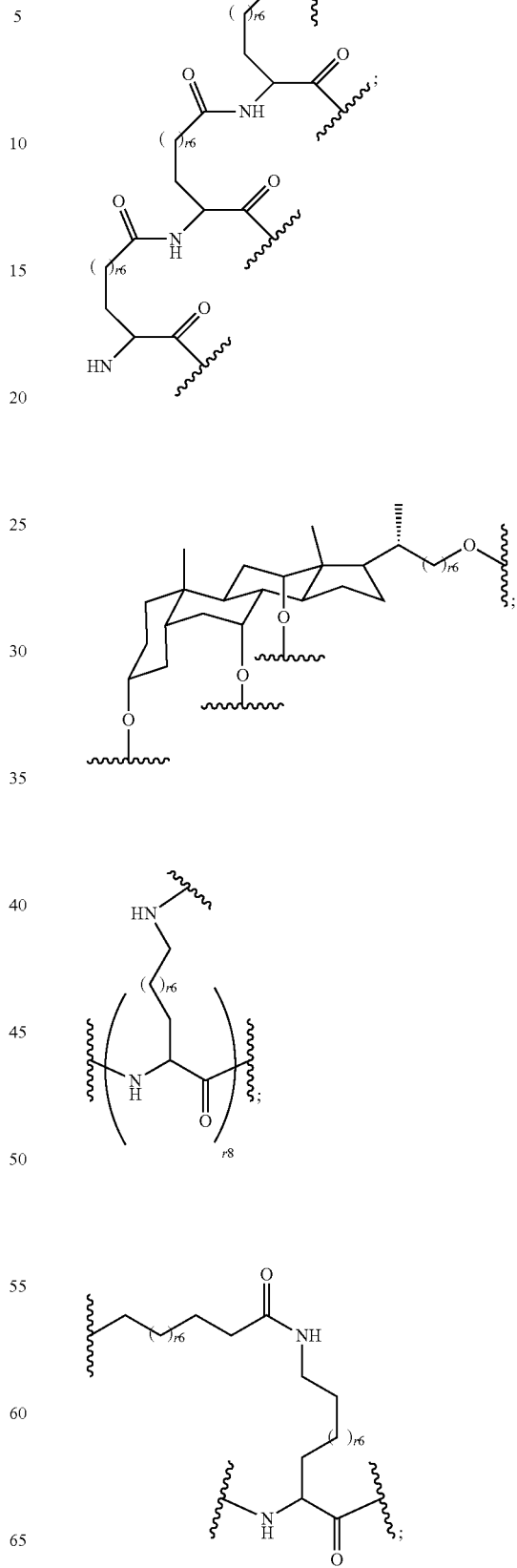

-continued
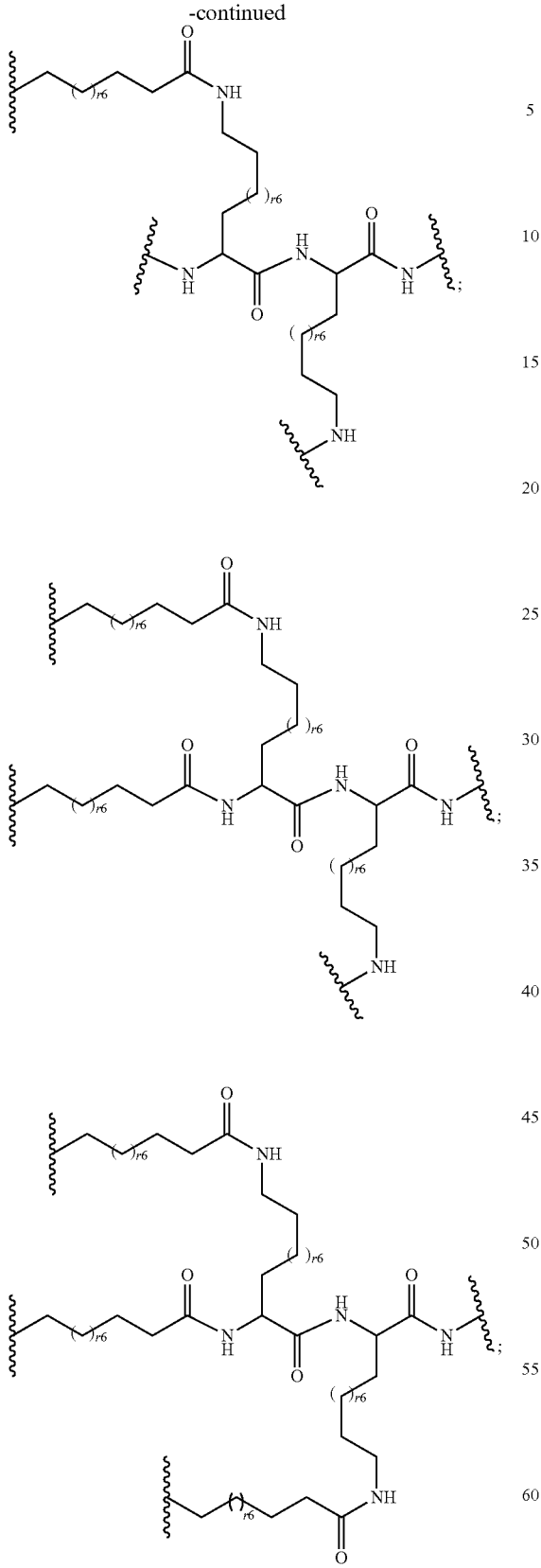
wherein r1, r3, r4 and r5 are positive integers of 1 to 15; r6 is a positive integer of 1 to 20, r7 is a positive integer of 2 to 6, and r8 is a positive integer of 1 to 3.
The linker B is selected from the following structures:
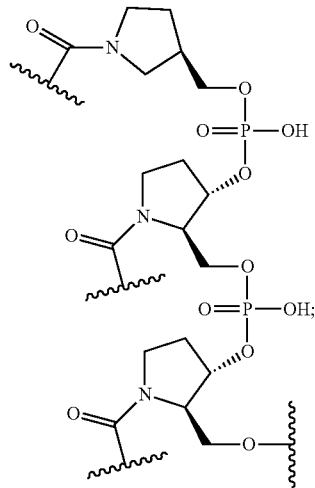
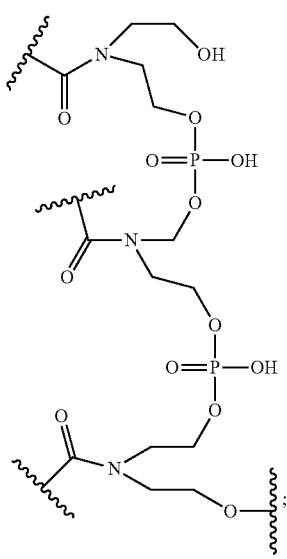
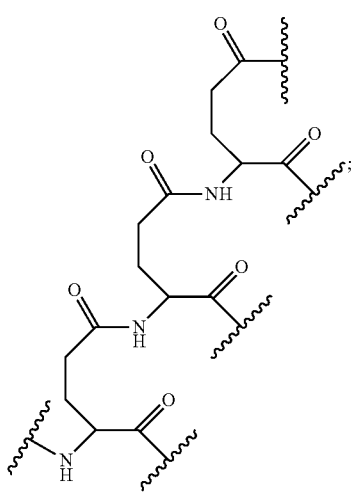

-continued
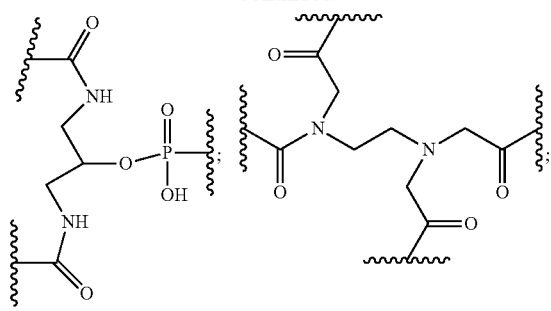
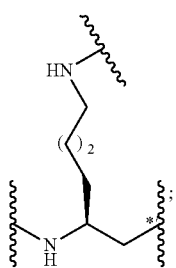
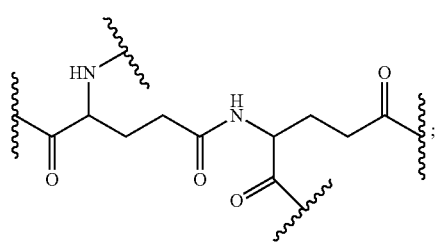
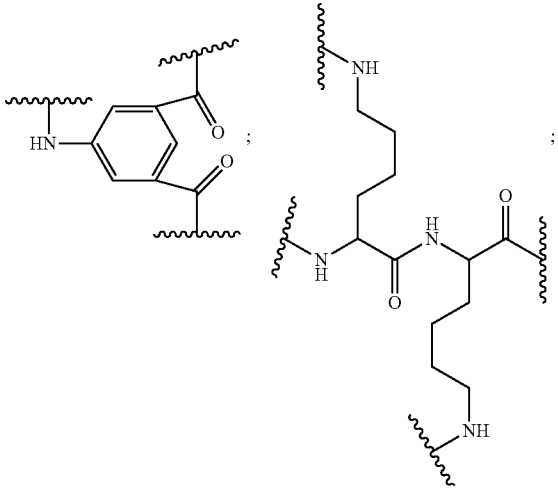
-continued
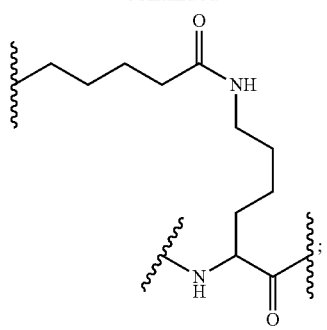
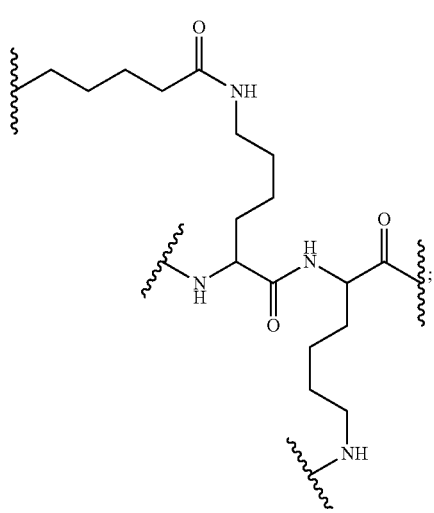
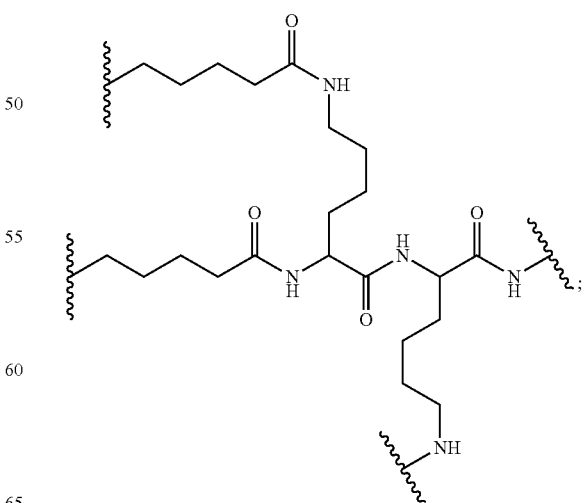

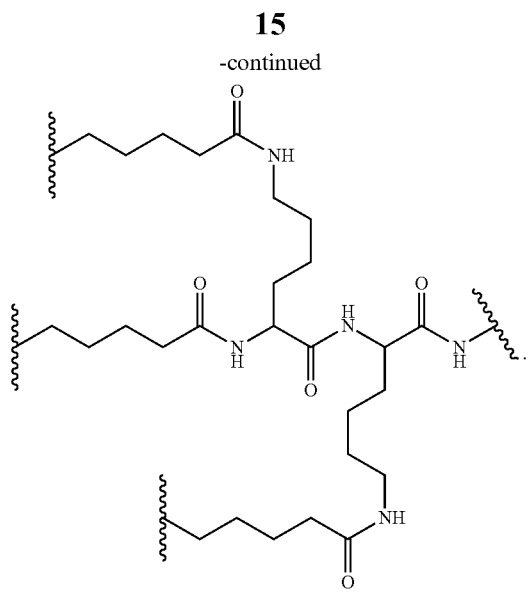

The linking chain D contains C5-C20, and may contain amino, carbonyl, amido, oxygen, sulfur, thiophosphoryl, phosphoryl, cyclic structure or a combination of these groups, and the right end of the linking chain D is connected to the corresponding part of the thyroid hormone receptor agonist T.

The linking chain D may be selected from the following structures:

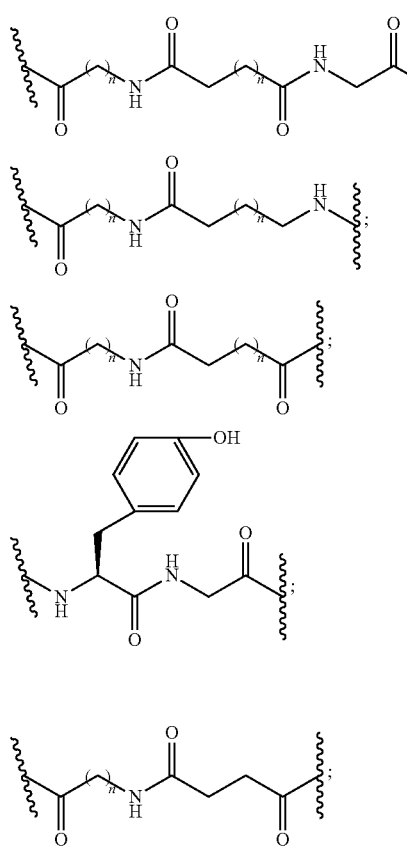

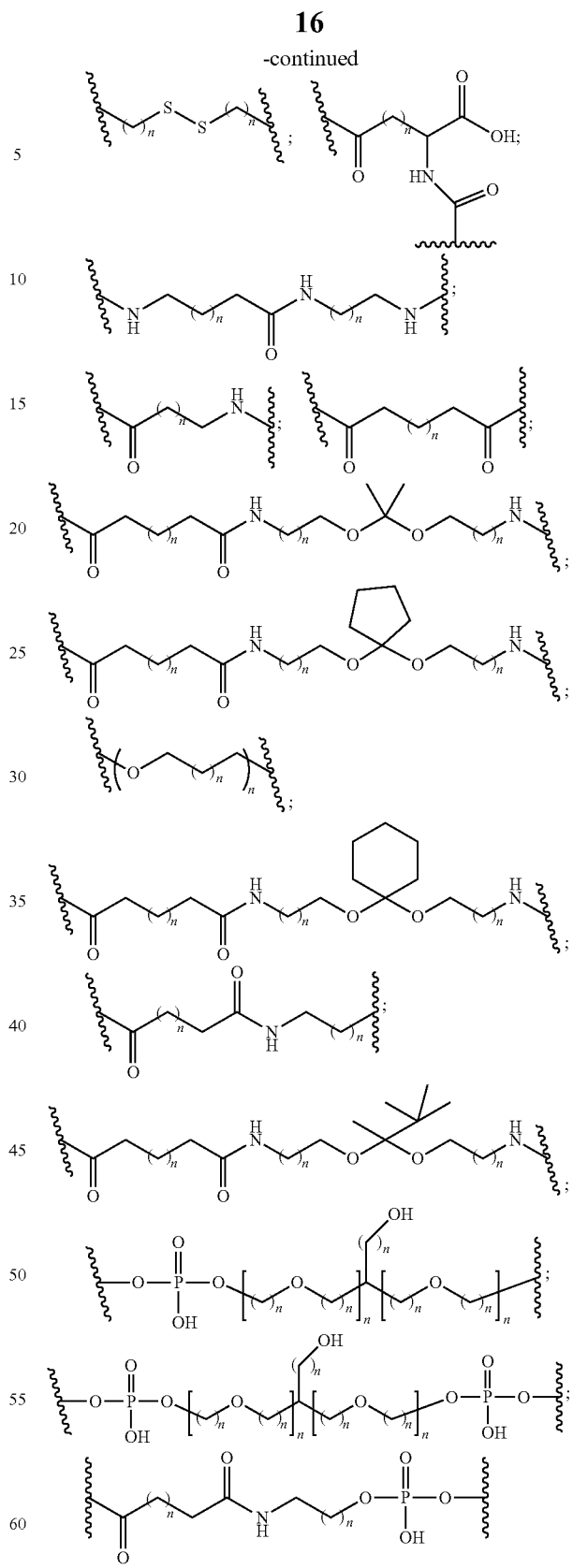

wherein, each n is a positive integer of 1 to 20, and each n is the same or different positive integer.

The linking chain D is one selected from the following structures:

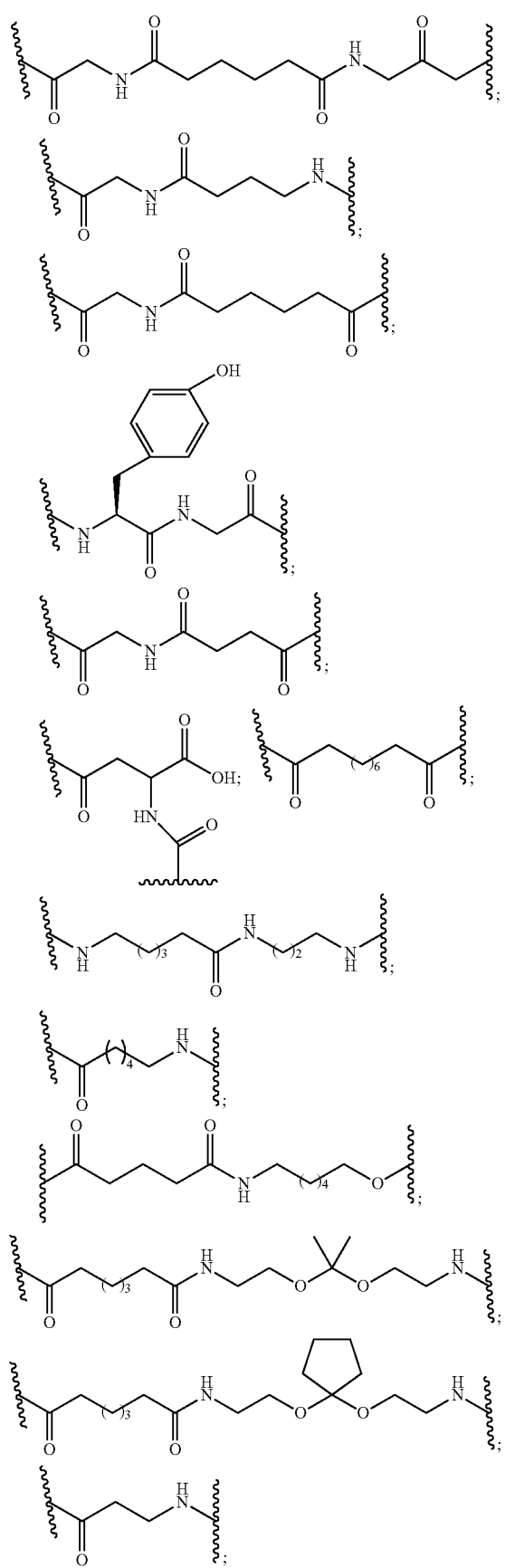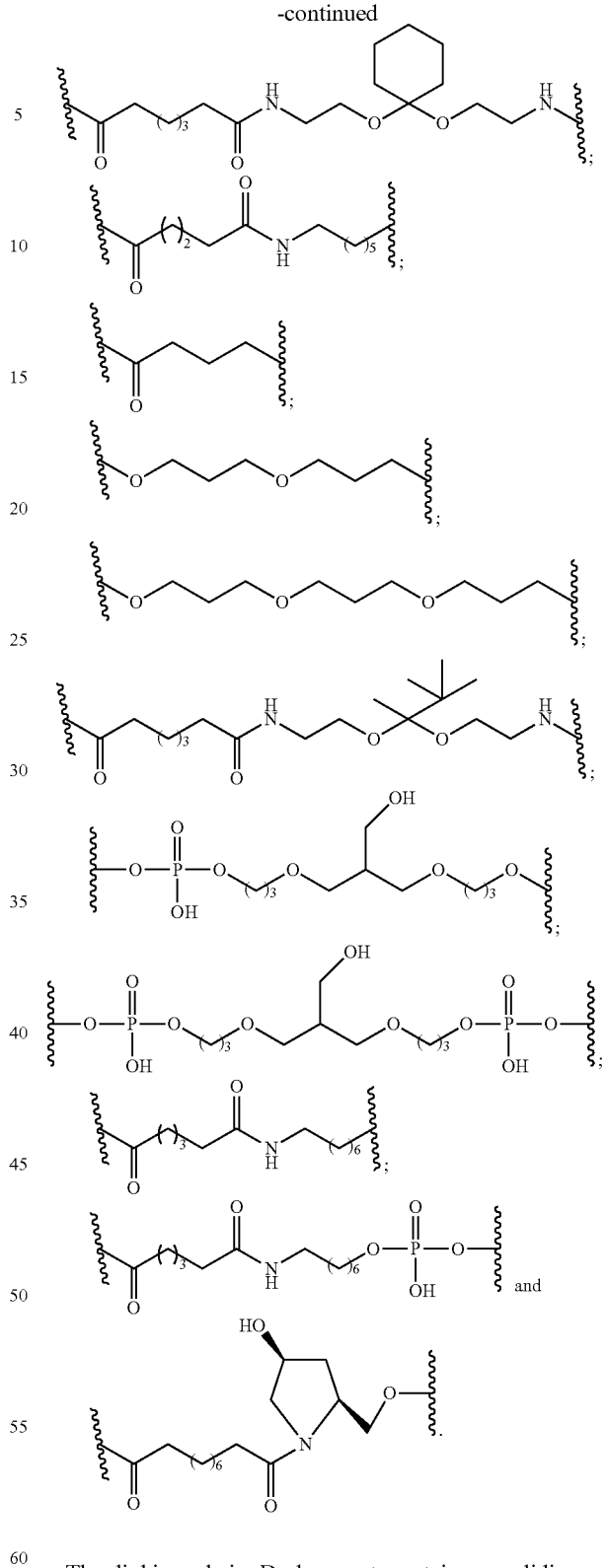
The linking chain D does not contain pyrrolidine or amide.
The linking chain D includes one of the following structures: pyrrolidine, PEG, amide, amine, disulfide bond and at least two amides.
The linking chain D is one selected from the following structures:

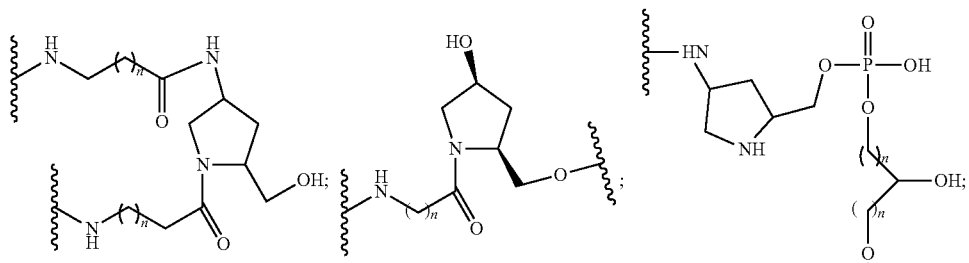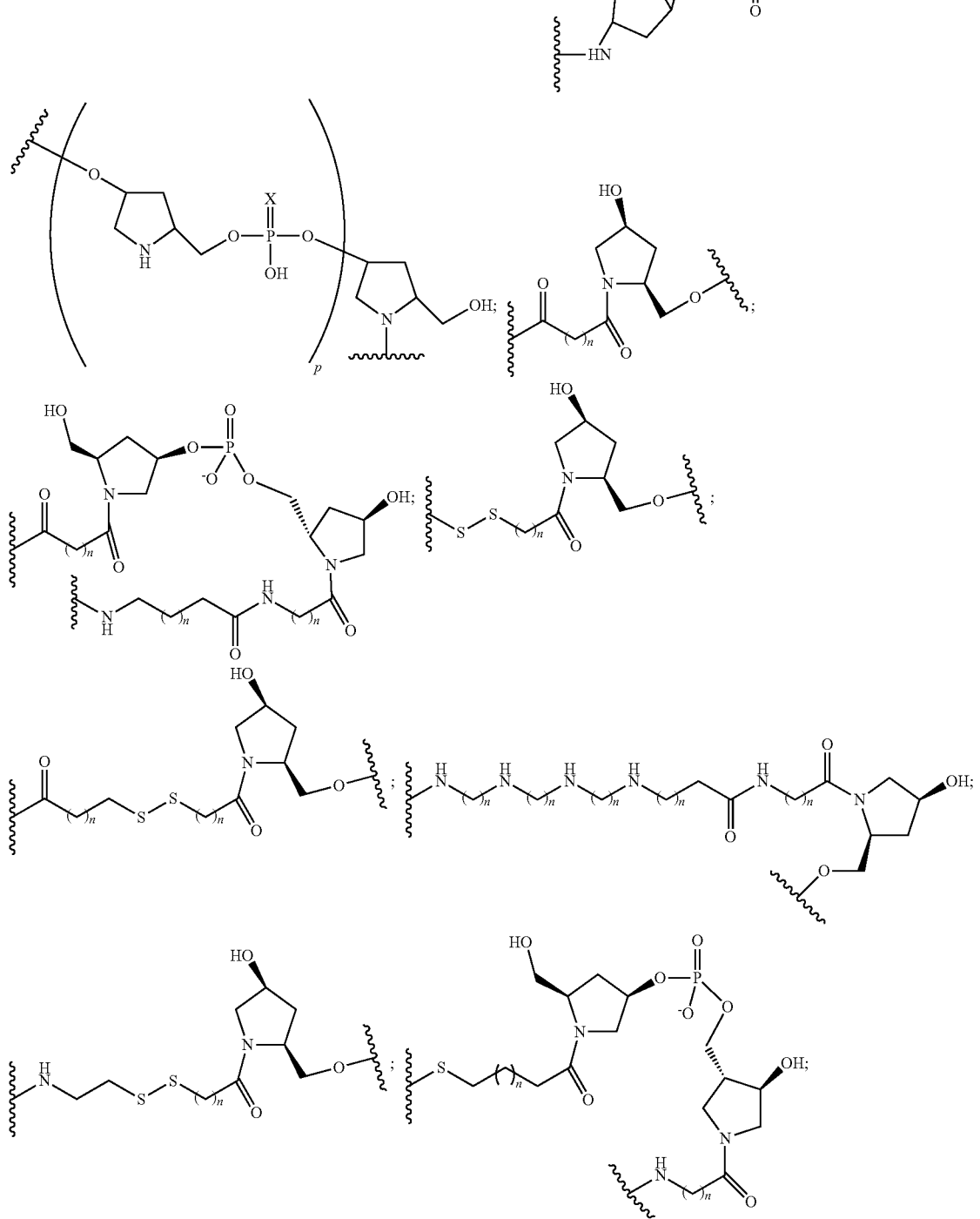

-continued
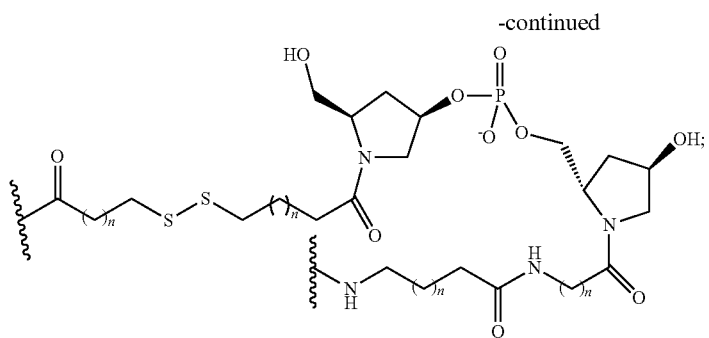
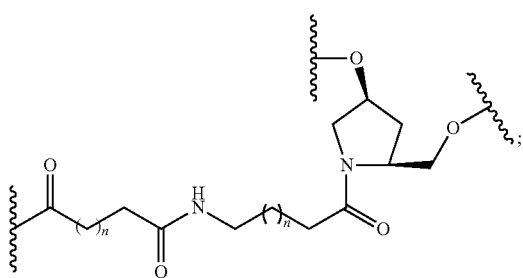
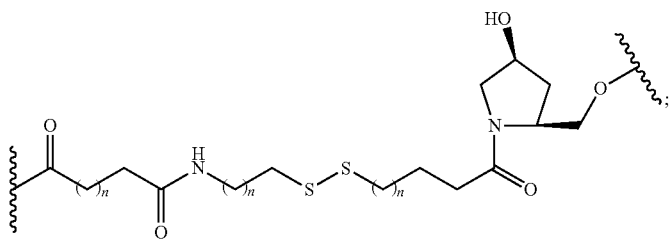
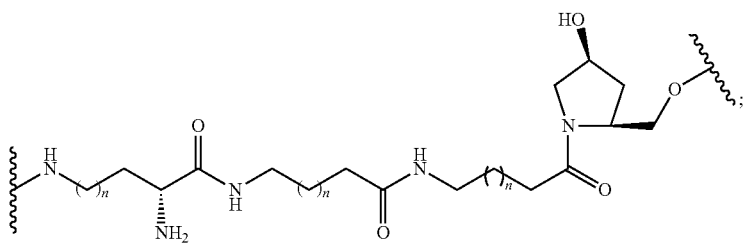
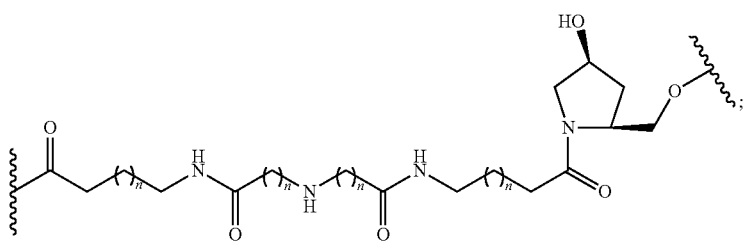
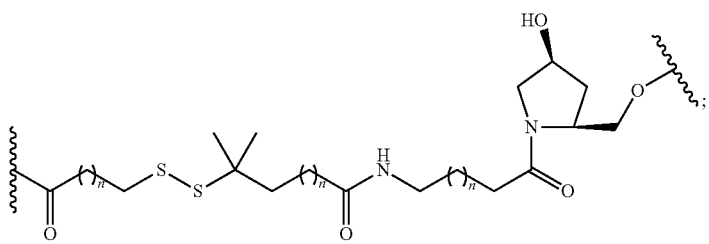

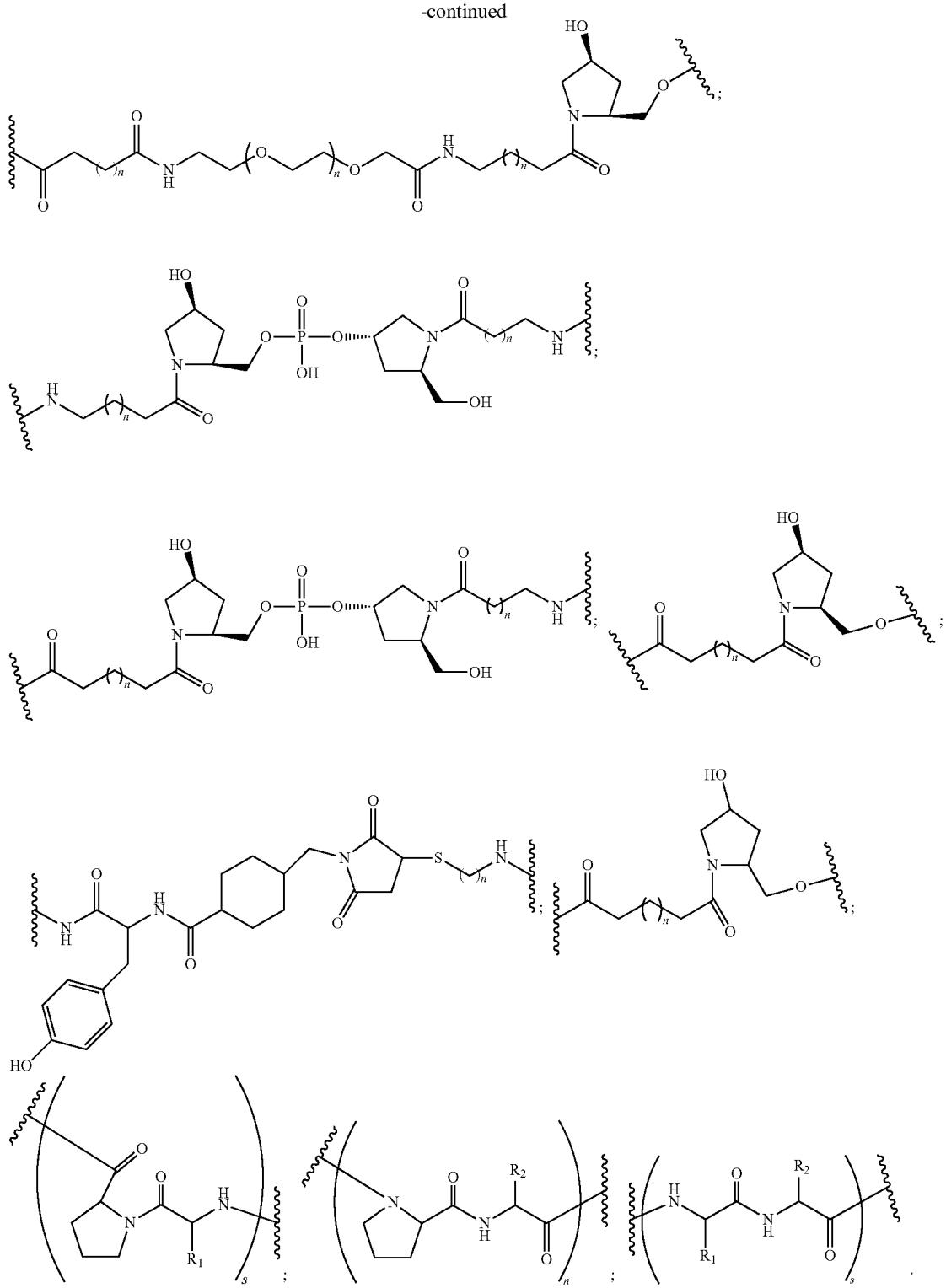

wherein, each n is a positive integer of 1 to 20, each n is the same or different positive integer, p is a positive integer of 1 to 6; s is a positive integer of 2 to 13; $R_1$ and $R_2$ may be the same or different substituent which may be one of the following structures: —H, —$CH_3$, —CH—$(CH_3)_2$, —$CH_2$—CH$(CH_3)_2$, —CH$(CH_3)$—$CH_2$—$CH_3$, —$CH_2$—$C_6H_5$, —$C_8NH_6$, —$CH_2$—$C_6H_4$—OH, —$CH_2$—COOH, —$CH_2$—$CONH_2$, —$(CH_2)_2$—COOH, —$(CH_2)_4$—$NH_2$, —$(CH_2)_2$—$CONH_2$, —$(CH_2)$—S—$CH_3$, —$CH_2$—OH, —CH$(CH_3)$—OH, —$CH_2$—SH, —$CH_2$—$C_3H_3N_2$, —$(CH_2)_3$NHC(NH)$NH_2$.

The linking chain D is one selected from the following structures:

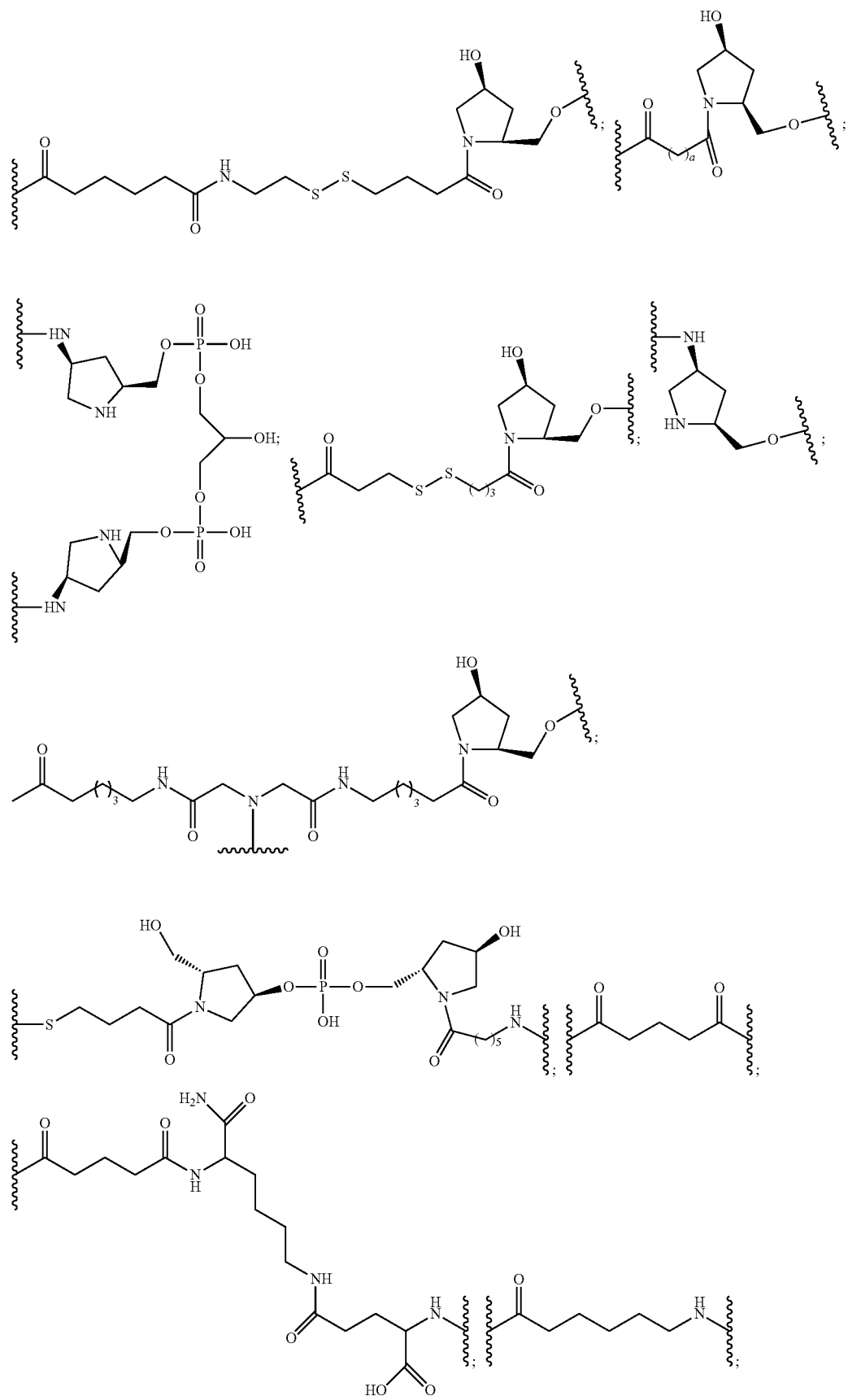

-continued
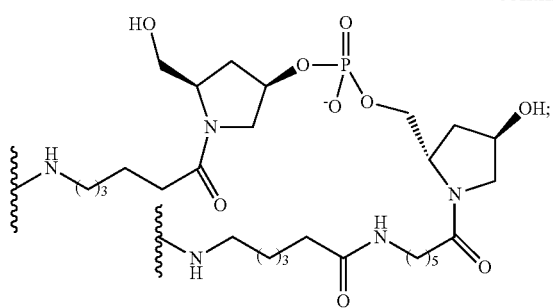
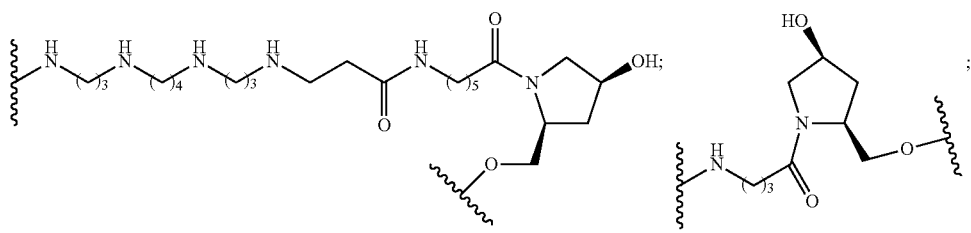
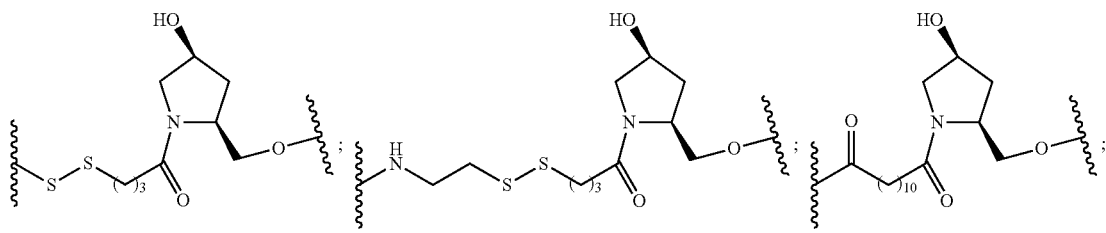
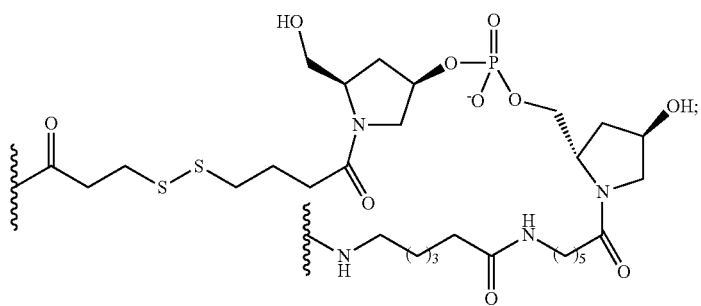
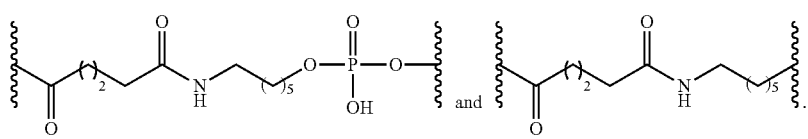

In the structure of the drug, the $(X-L)_n$-B group is one selected from the following structures, and has a right end connected to the left end of the linking chain D:
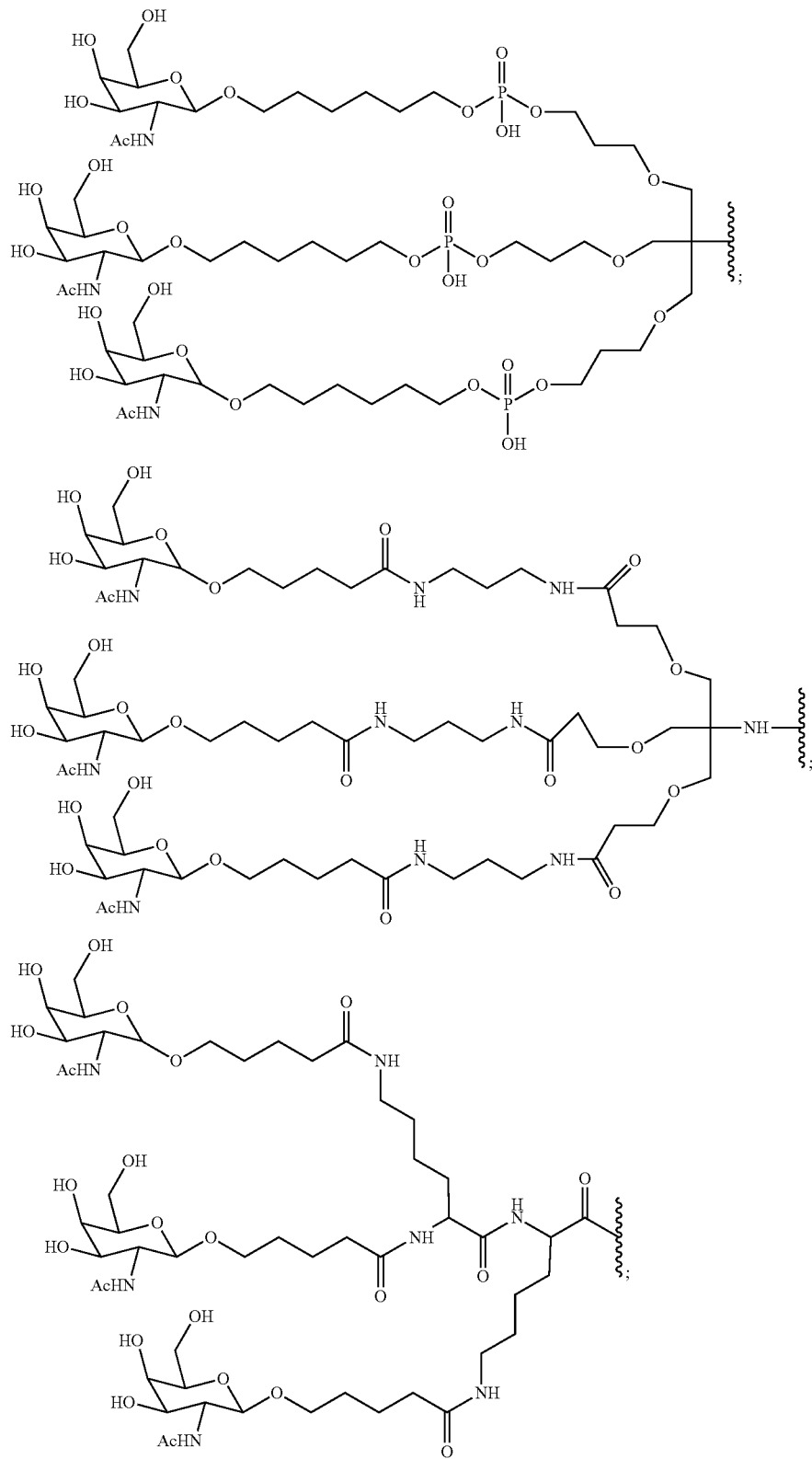

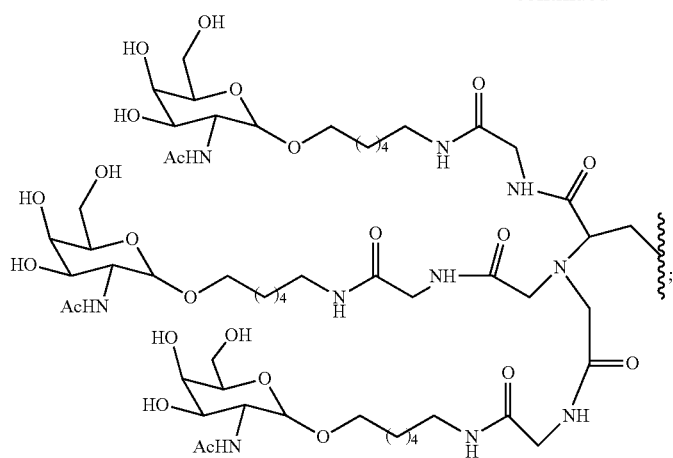
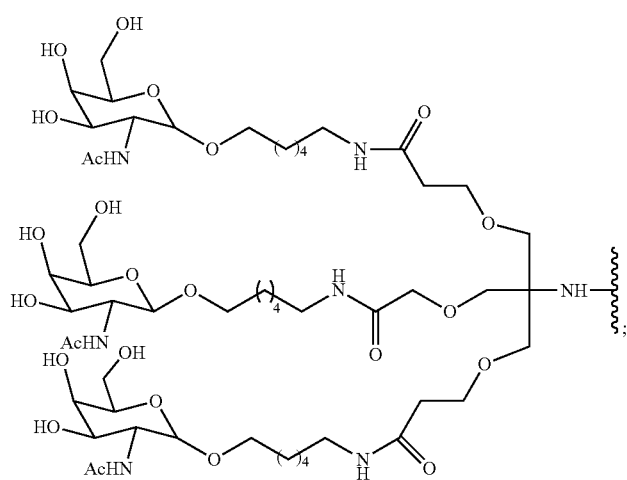
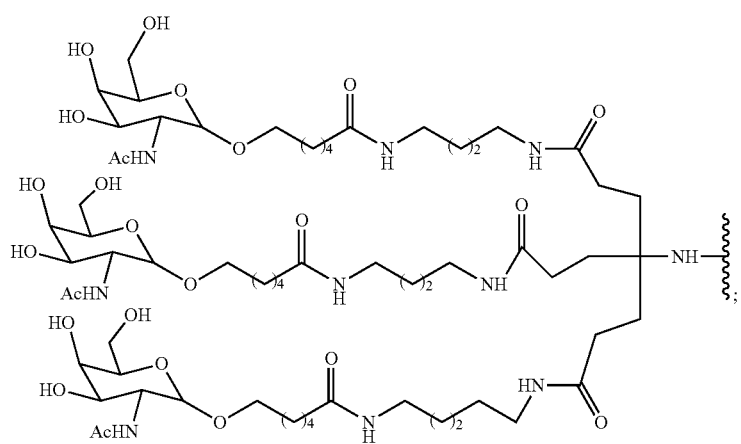

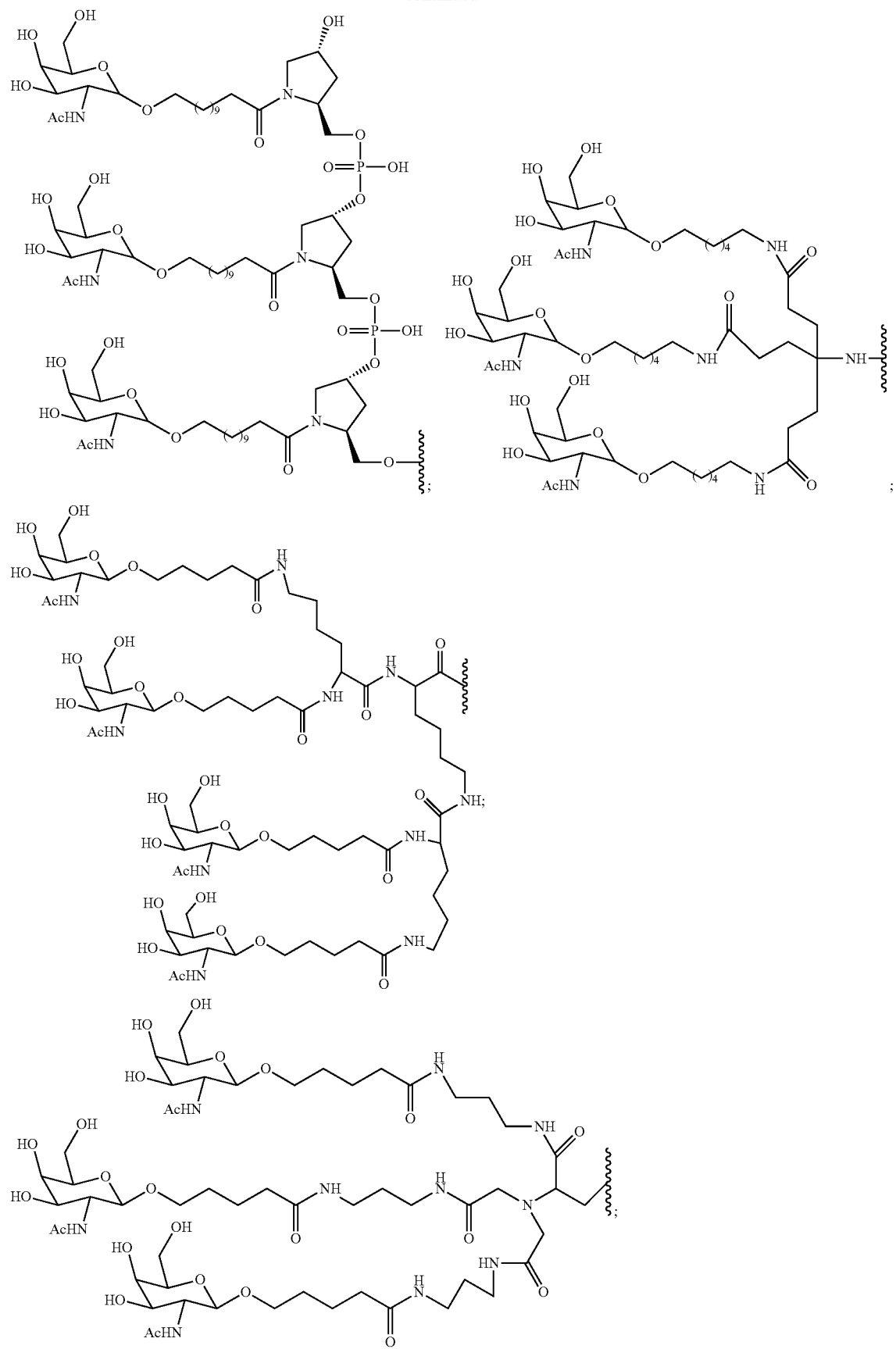

-continued
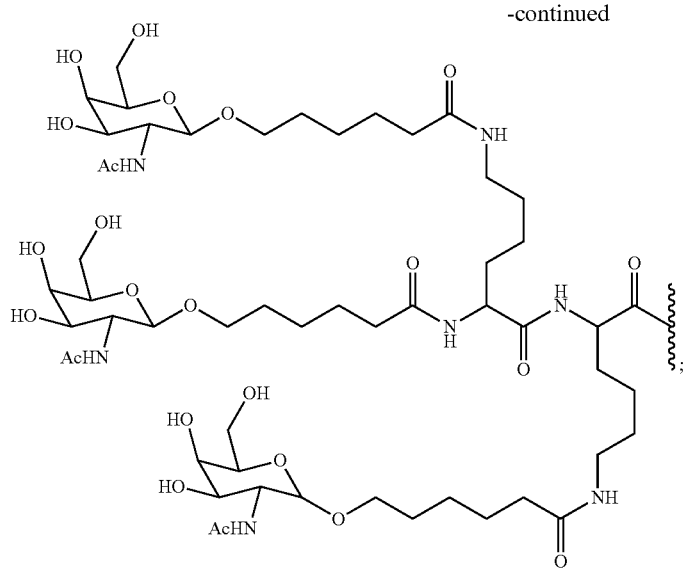
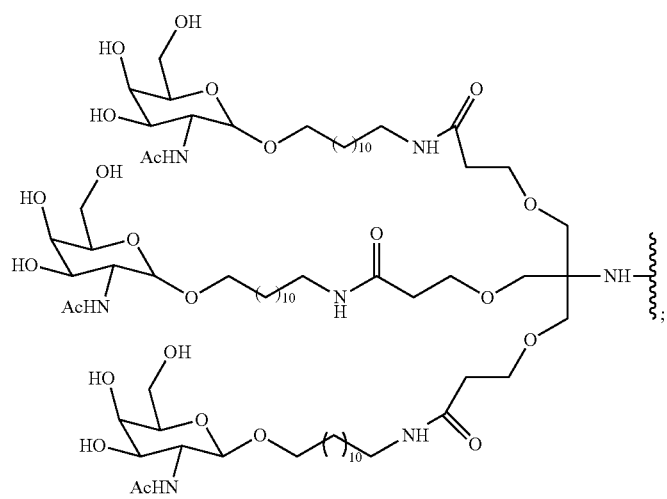
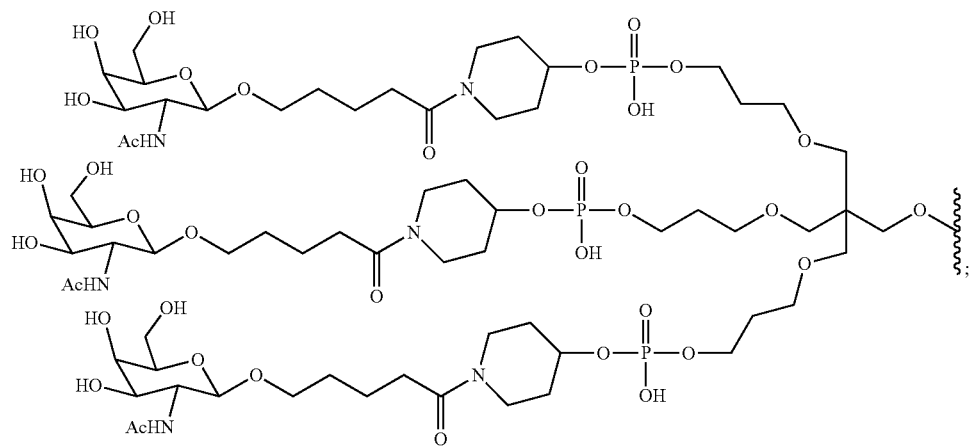

-continued
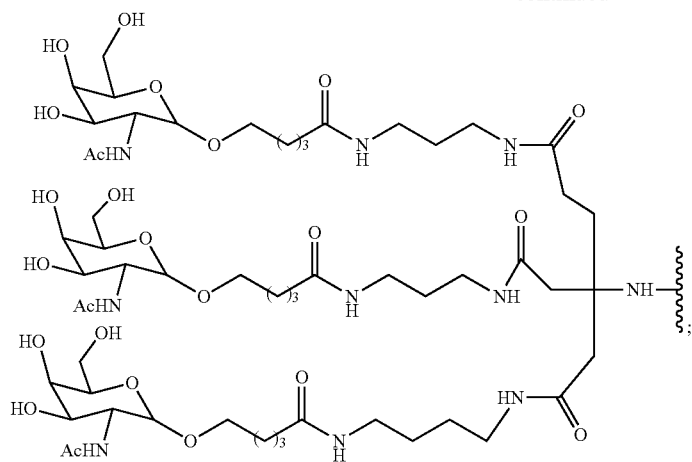
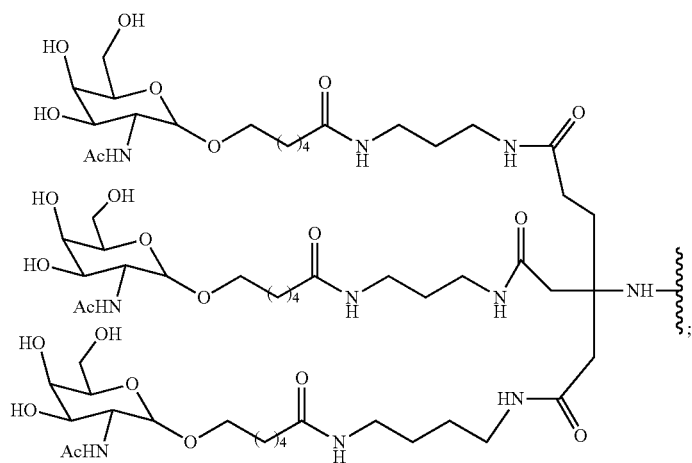

-continued
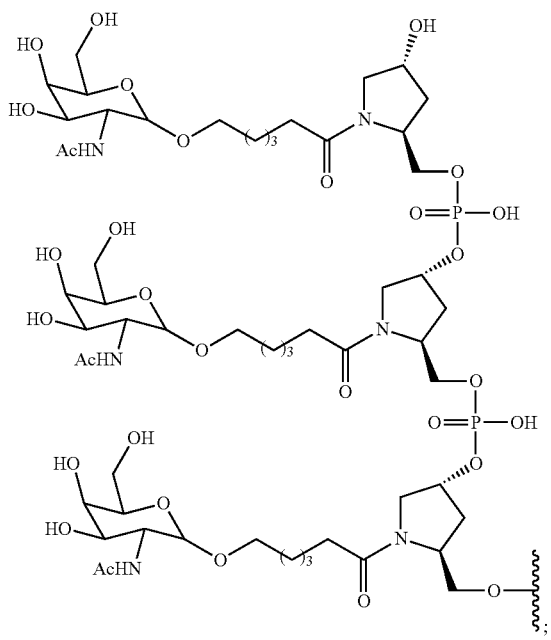
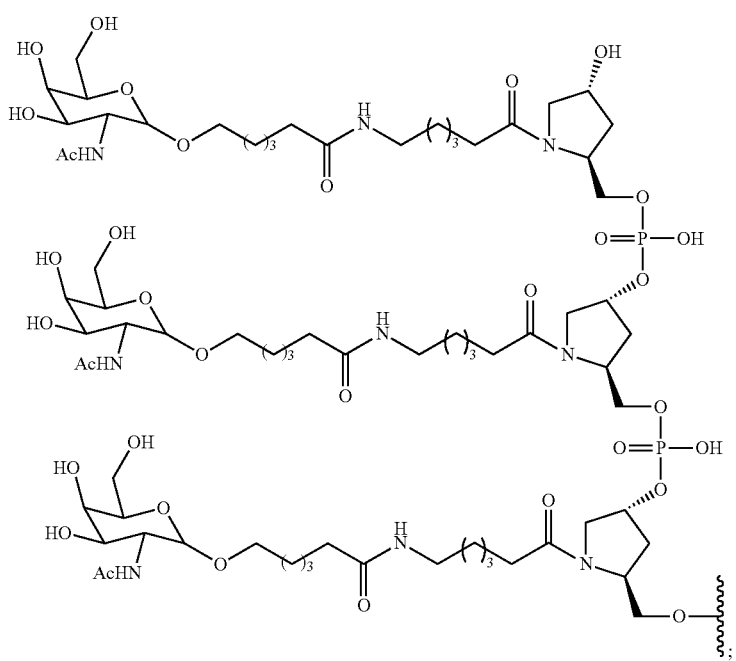

-continued
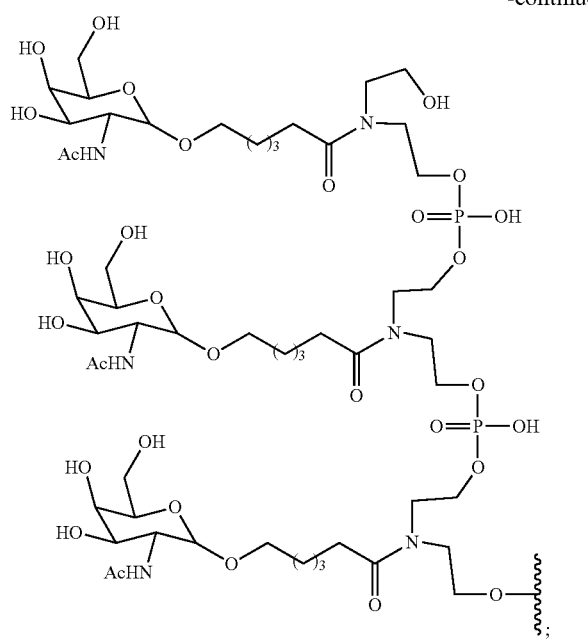
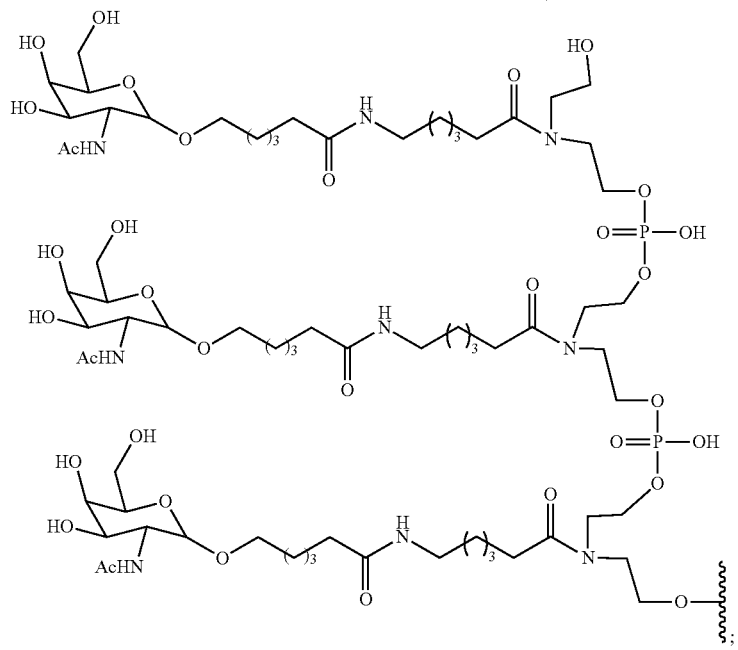
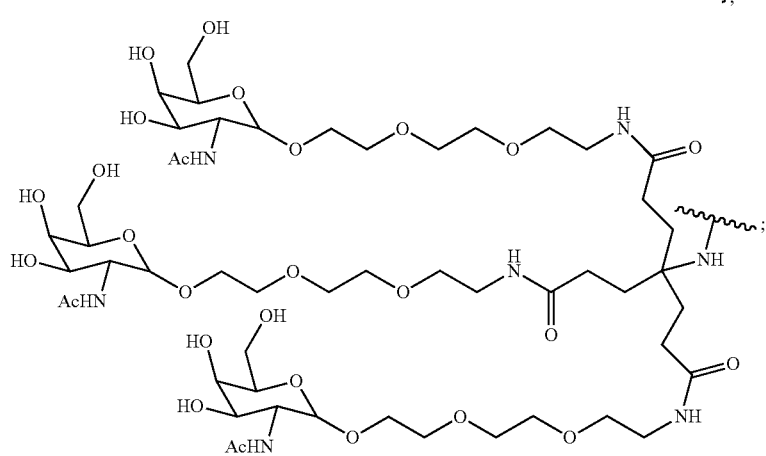

-continued
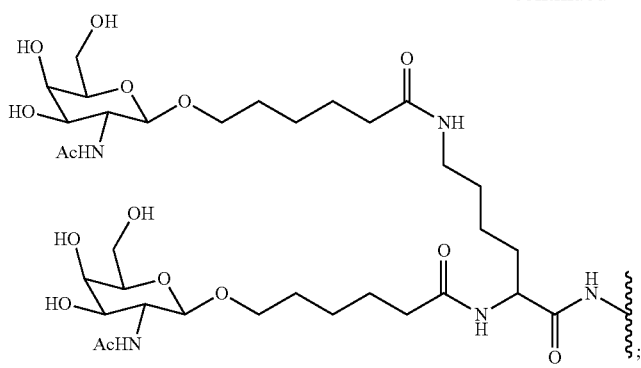
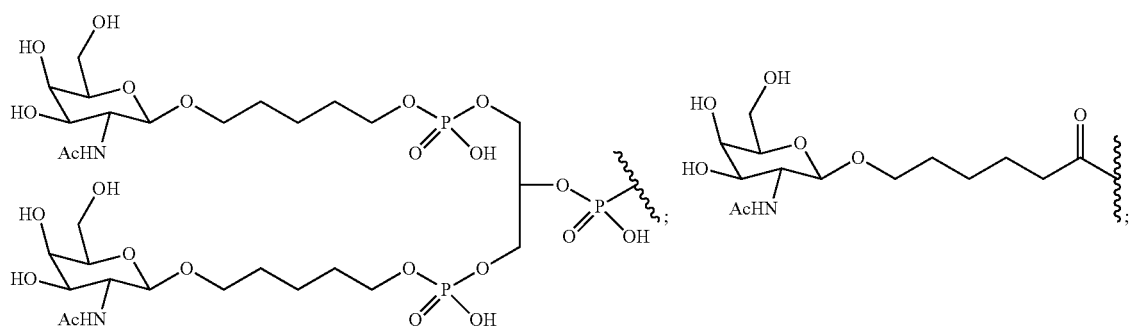
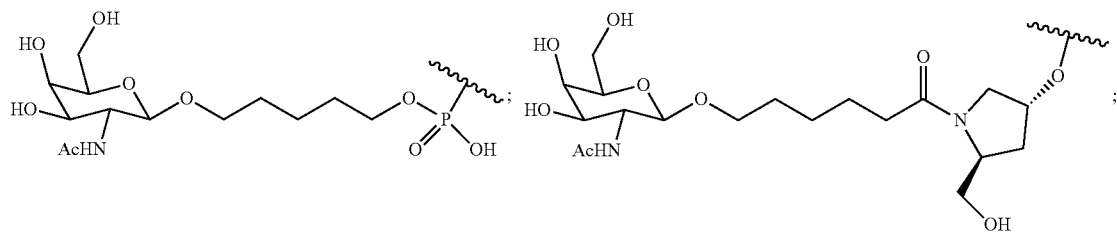
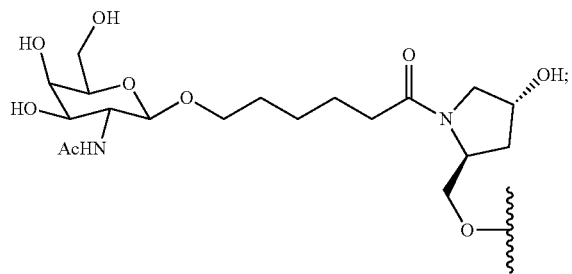
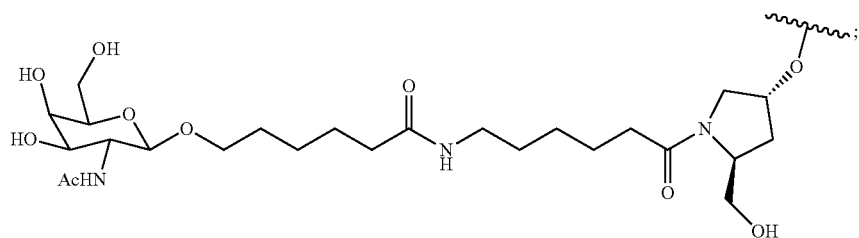

-continued
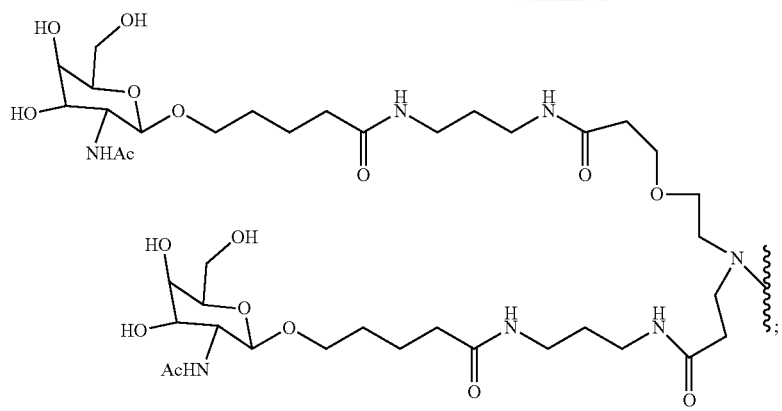
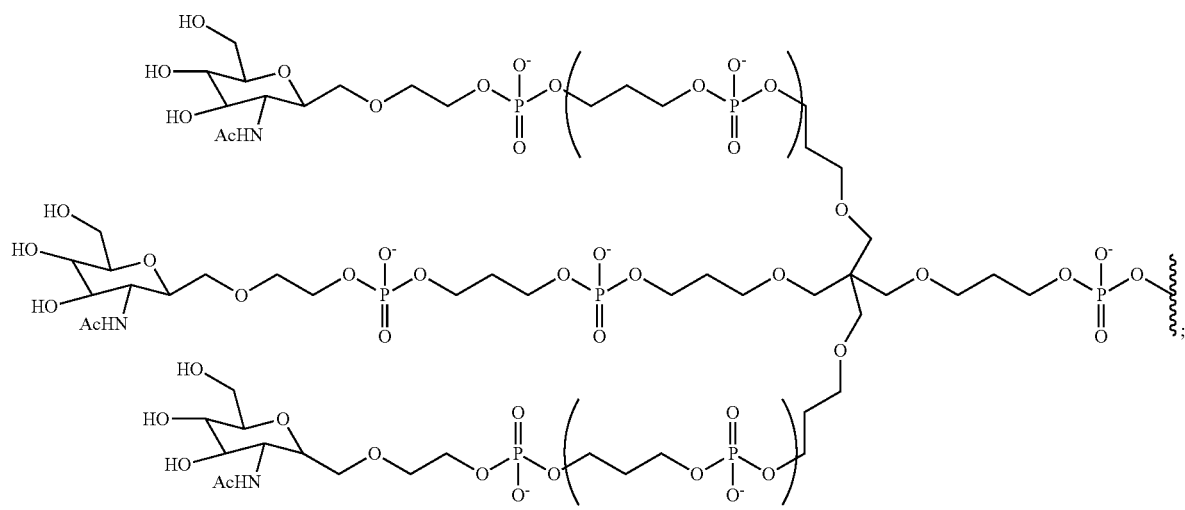
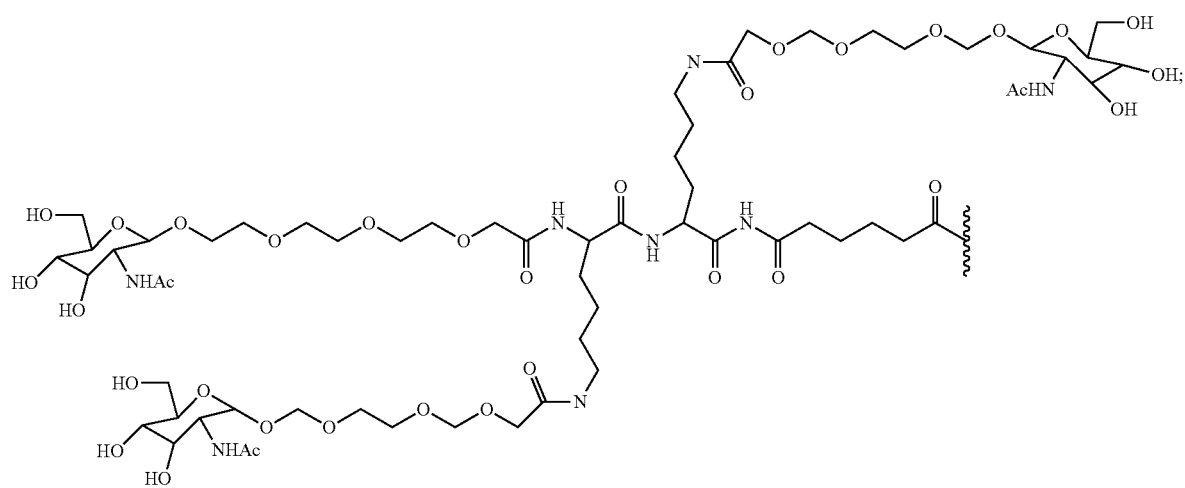

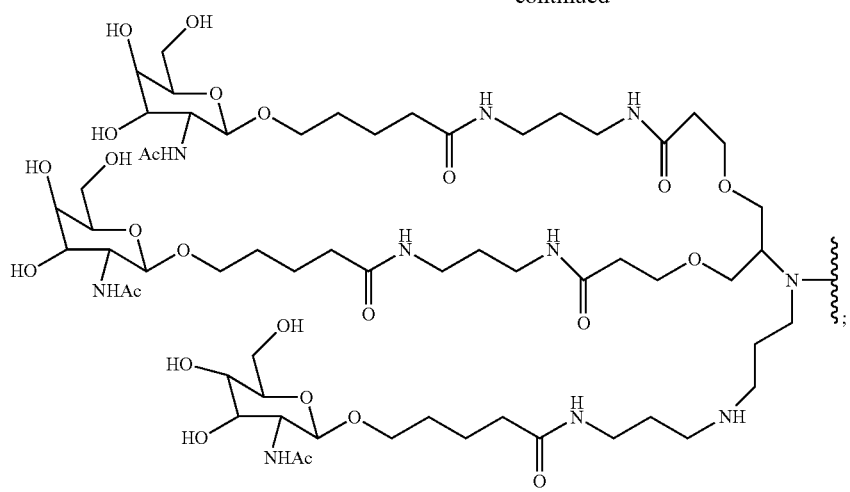
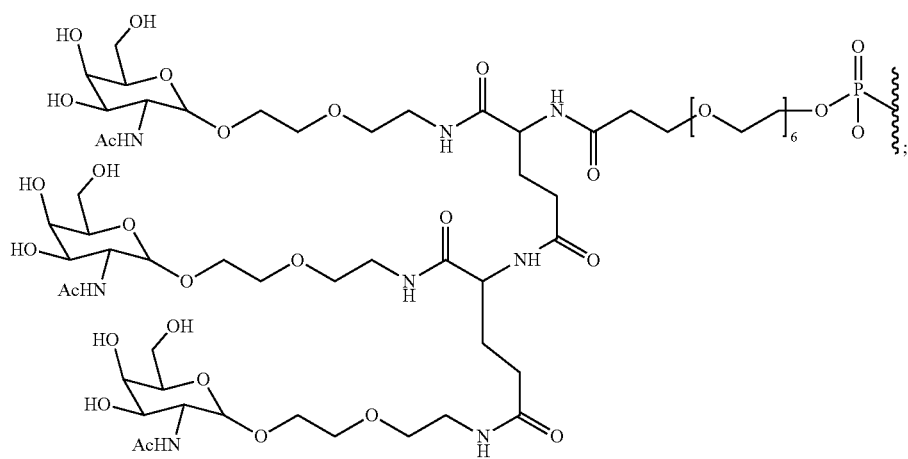
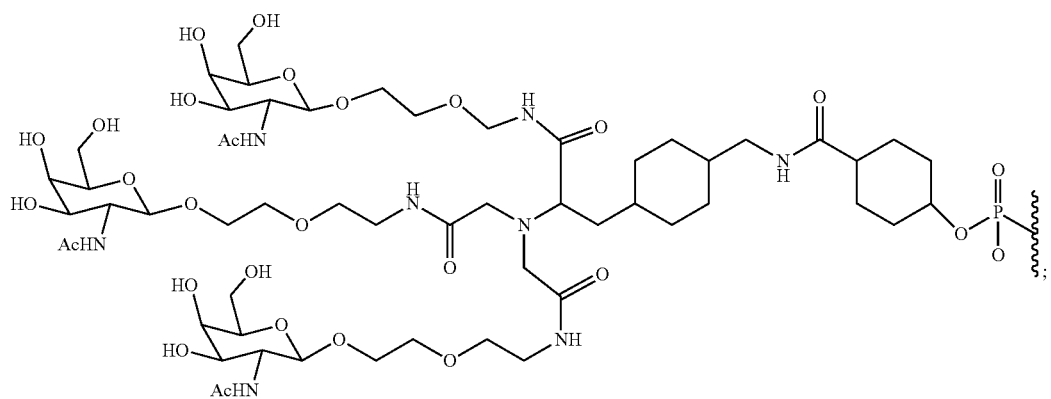

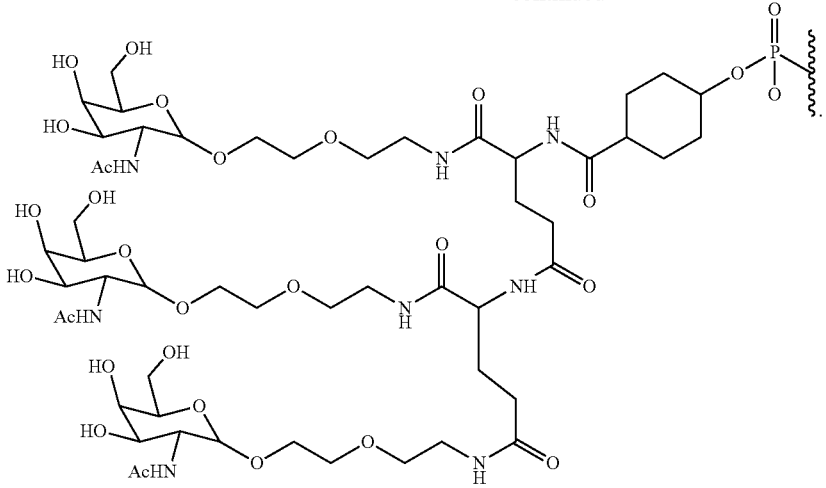

The thyroid hormone receptor agonist has the following structure:

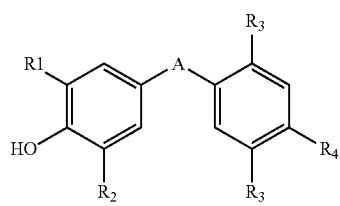

wherein A is oxygen, sulfur, carbonyl, methylene or amino; R1 is C1-C4 linear or branched alkyl, —CH$_2$(nitrogen heterocycle), —CH(OH)(halogenated benzene or aromatic hydrocarbon), —CH(OH)CH$_3$, halogen or hydrogen; R$_2$ is halogen, —CH$_3$ or hydrogen; R$_3$ is halogen, CH$_3$ or hydrogen; R$_4$ is —CH$_2$CH(NH)COOH, —OCH$_2$COOH, —NHC(O)COOH, —CH$_2$COOH, —NHC(O)CH$_2$COOH, —CH$_2$CH$_2$COOH, —OCH$_2$PO$_3{}^{2-}$, —NHC(O)CH$_2$COOH, OH, halogen or C1-C4 alkyl.

The thyroid hormone receptor agonist is thyroxine (T4) or triiodothyronine (T3) or metabolites thereof. The thyroid hormone receptor agonist has a structure which is one of the following structures:

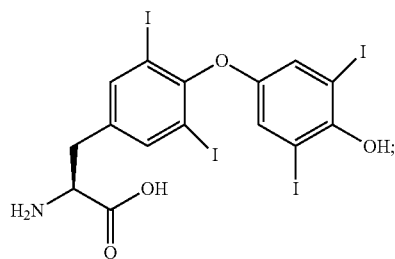

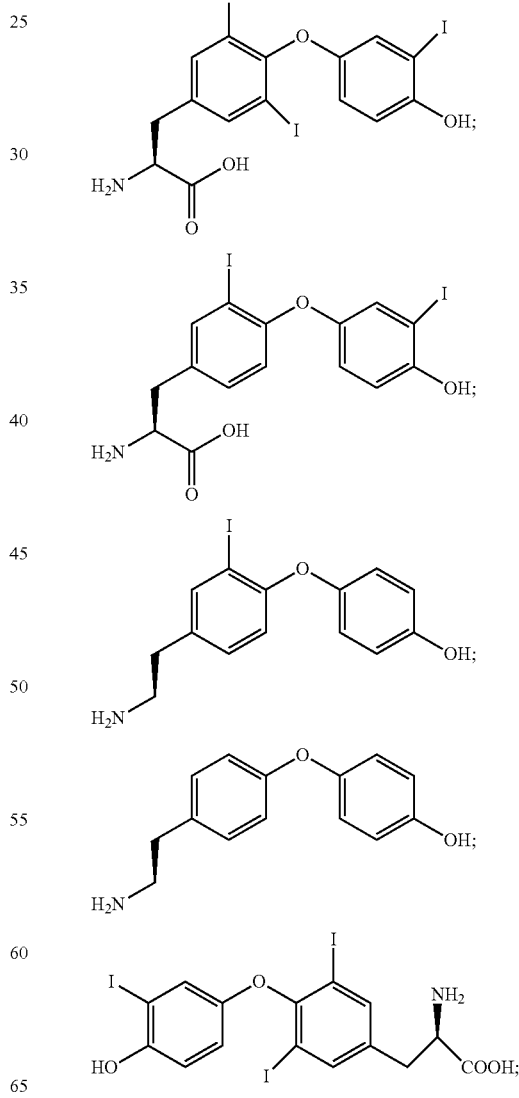

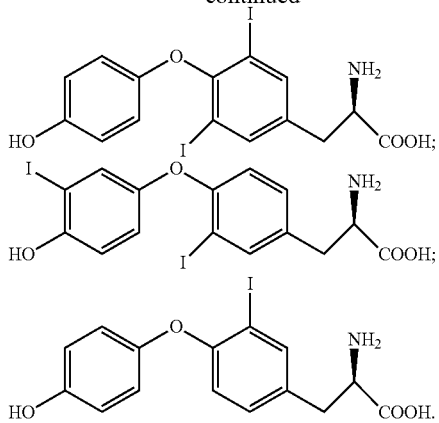

The thyroid hormone receptor agonist is one having the following characteristic structure:

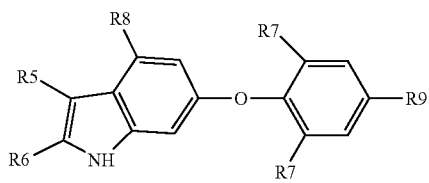

wherein R6 is C1-C4 linear or branched alkyl or hydrogen; R5 is C1-C8 alkyl; R7 is halogen, C1-C4 alkyl; R8 is C1-C4 linear or branched alkyl or hydrogen; R9 is —CH$_2$CH(NH)COOH, —OCH$_2$COOH, —NHC(O)COOH, —CH$_2$COOH, NHC(O)CH$_2$COOH, CH$_2$CH$_2$COOH, —OCH$_2$PO$_3^{2-}$, —NHC(O)CH$_2$COOH, OH, halogen or C1-C4 alkyl.

The thyroid hormone receptor agonist has a structure of:

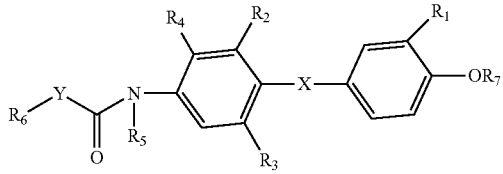

wherein X is oxygen, sulfur, carbonyl, methylene, or amino; Y is one of C1-C5 alkyl carbon chain and C≡C; R$_1$ is halogen, trifluoromethyl, C1-C6 alkyl, C3-C7 cycloalkyl; R$_2$ and R$_3$ are one or two of hydrogen, halogen, C1-C6 alkyl and C3-C7 cycloalkyl, and one of R$_2$ and R$_3$ must be hydrogen; R$_4$ is hydrogen or C1-C4 alkyl; R$_5$ is hydrogen or C1-C4 alkyl; R$_6$ is a carboxyl acid or an ester bond; R$_7$ is hydrogen, acyl or aroyl.

Specifically, the thyroid hormone receptor agonist has one of the following structures:

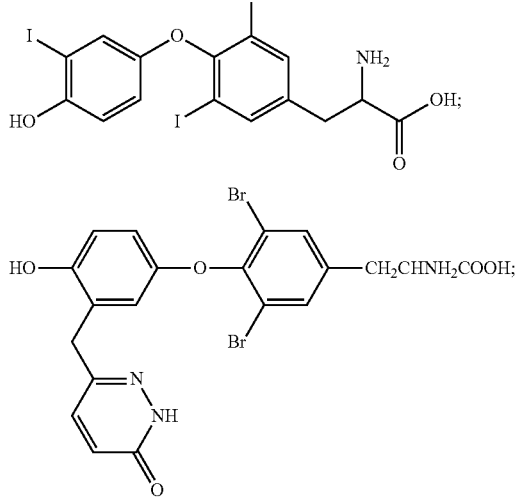

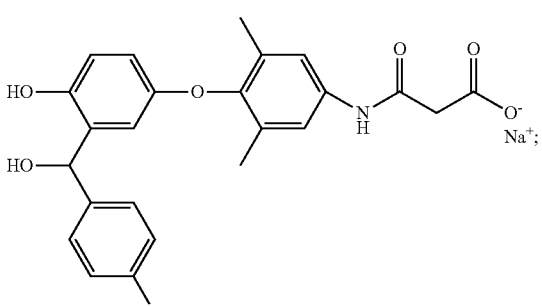

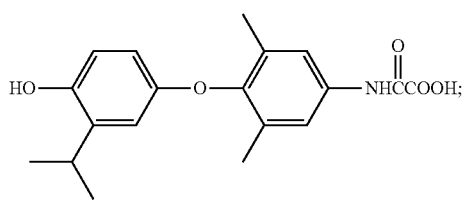

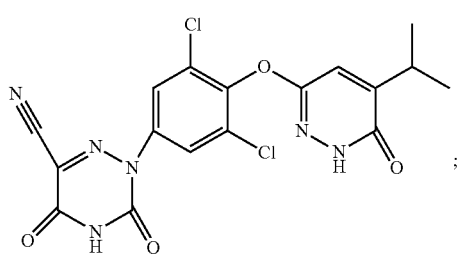

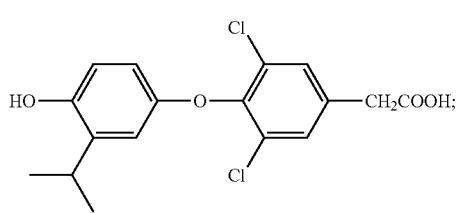

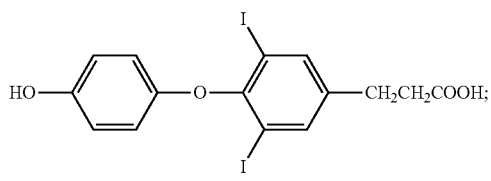

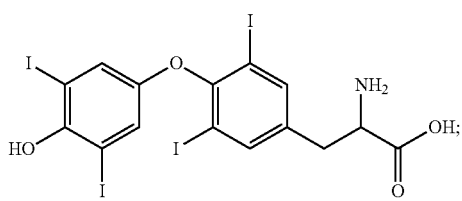

53
-continued
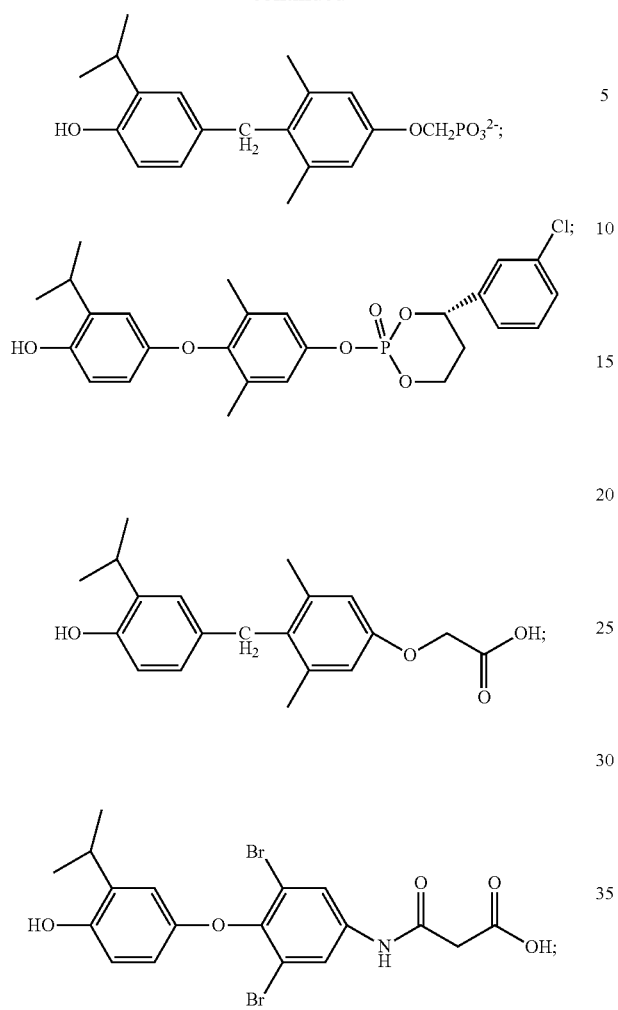
54
-continued
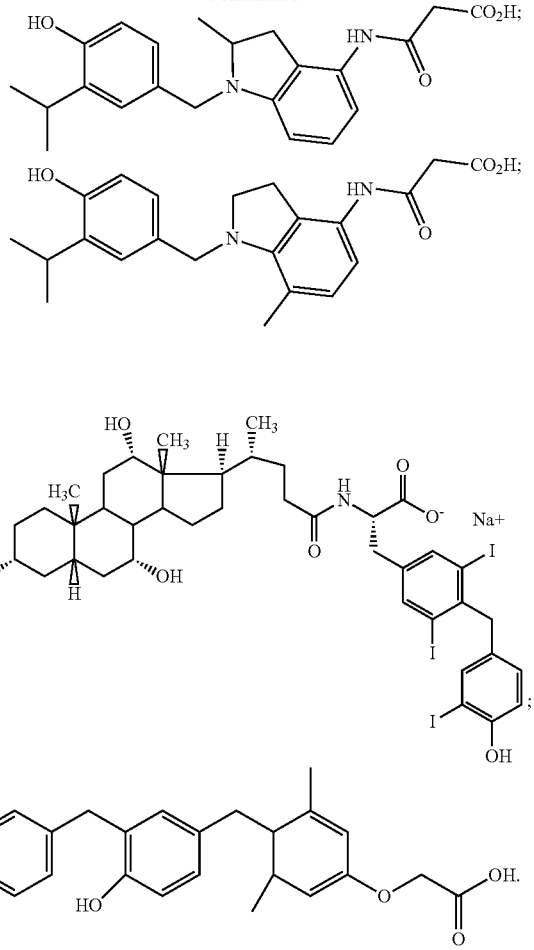
The drug (X-L)$_n$-B-D-T has one of the structures shown in Kylo-0101 to Kylo-0104:
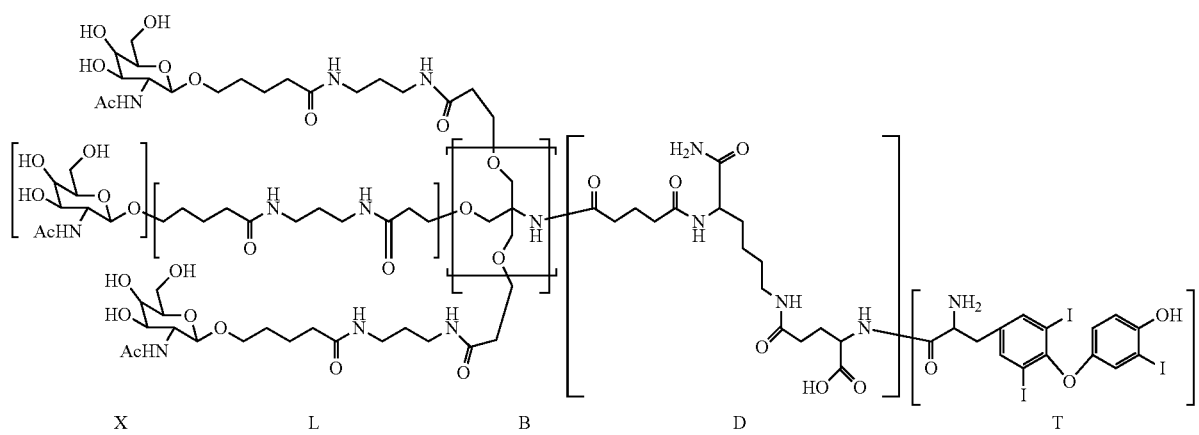
Kylo-0101

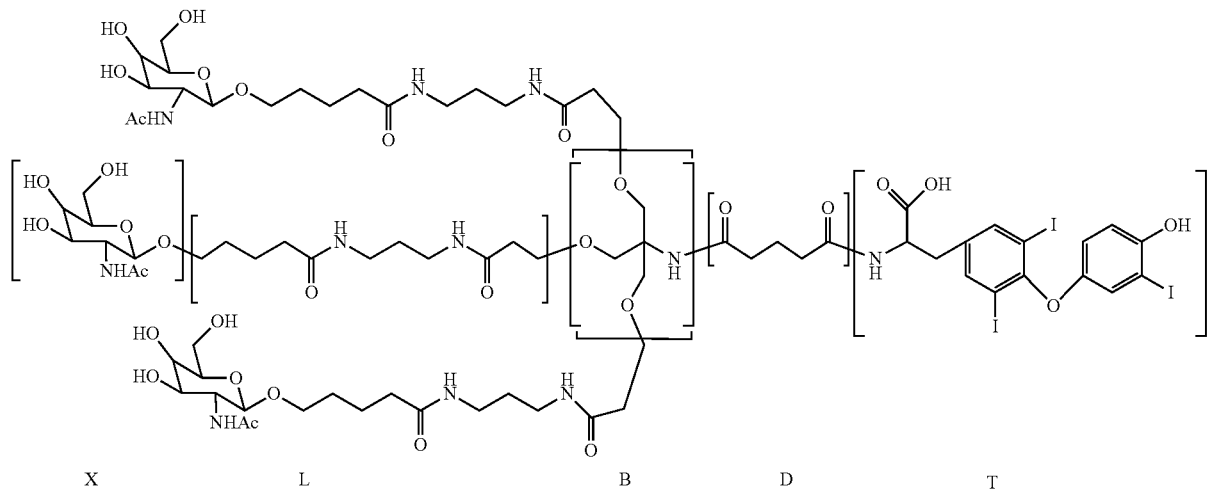
Kylo-0102
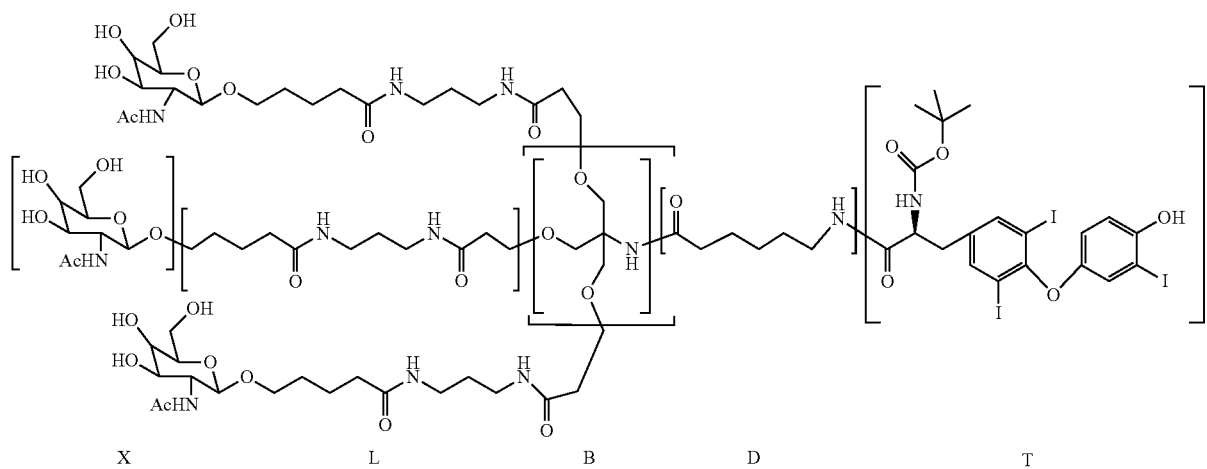
Kylo-0103
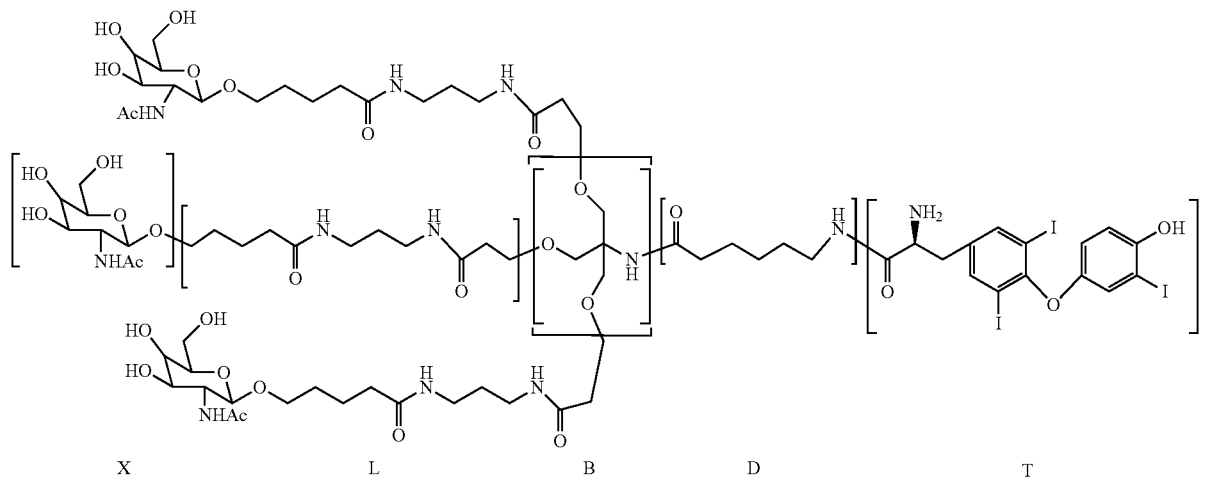
Kylo-0104

Also provided is use of the drug in preparation of a medicament that acts on a thyroid hormone receptor to treat a liver-derived disease.

The thyroid hormone receptor is an asialoglycoprotein receptor, and the liver-derived disease is non-alcoholic fatty liver or non-alcoholic steatohepatitis.

Compared with the prior art, the beneficial effects of the present invention are as follows.

(1) The invention treats lipid metabolism disorders and related complications and reverses non-alcoholic fatty liver, non-alcoholic steatohepatitis and liver fibrosis through specific liver targeting and activation of thyroid hormone receptors in liver cells.

(2) The invention provides a drug containing a liver targeting specific ligand for asialoglycoprotein receptor and a thyroid hormone receptor agonists in the structure, wherein the liver targeting specific ligand is connected to the thyroid hormone receptor agonist through a branched chain, a linker and a linking chain to form a new compound structure.

(3) Thyroid hormone receptors (TRs) are divided into two subtypes, TR-α and TR-β, wherein TR-β is mainly expressed in the liver, and TR-α is mainly expressed in the heart, nervous system, etc. The drug provided by the present invention has liver-targeting effect, can bring a thyroid hormone receptor agonist specifically into the liver, so that it does not enter the heart and other tissues, avoiding the side effects induced by the thyroid hormone receptor agonist on TR-α and maintaining the efficacy in treating lipid metabolism disorders and related complications.

(4) The branched chain L containing a structure for stabilizing steric hindrance, acts as a steric stabilizer in the new drug. With respect to a drug without the steric hindrance structure, the branched chain L can prevent or inhibit the intermolecular or intramolecular interaction of the drug to which it is bound. It can also prevent the drug to which it is bound from participating in electrostatic interaction. The electrostatic interaction is the non-covalent bonding between two or more substances due to the attractive force between positive and negative charges. In the drug of the present invention, the branched chain L can inhibit the interaction between the drug and blood components, such as phagocytosis, so as to increase the circulation time of the molecule to which it is bound.

DESCRIPTION OF THE DRAWINGS

The present invention provides the following description of the drawings to make the objectives, technical solutions and beneficial effects of the present invention clearer.

BEST MODE FOR THE INVENTION

Figure 1:
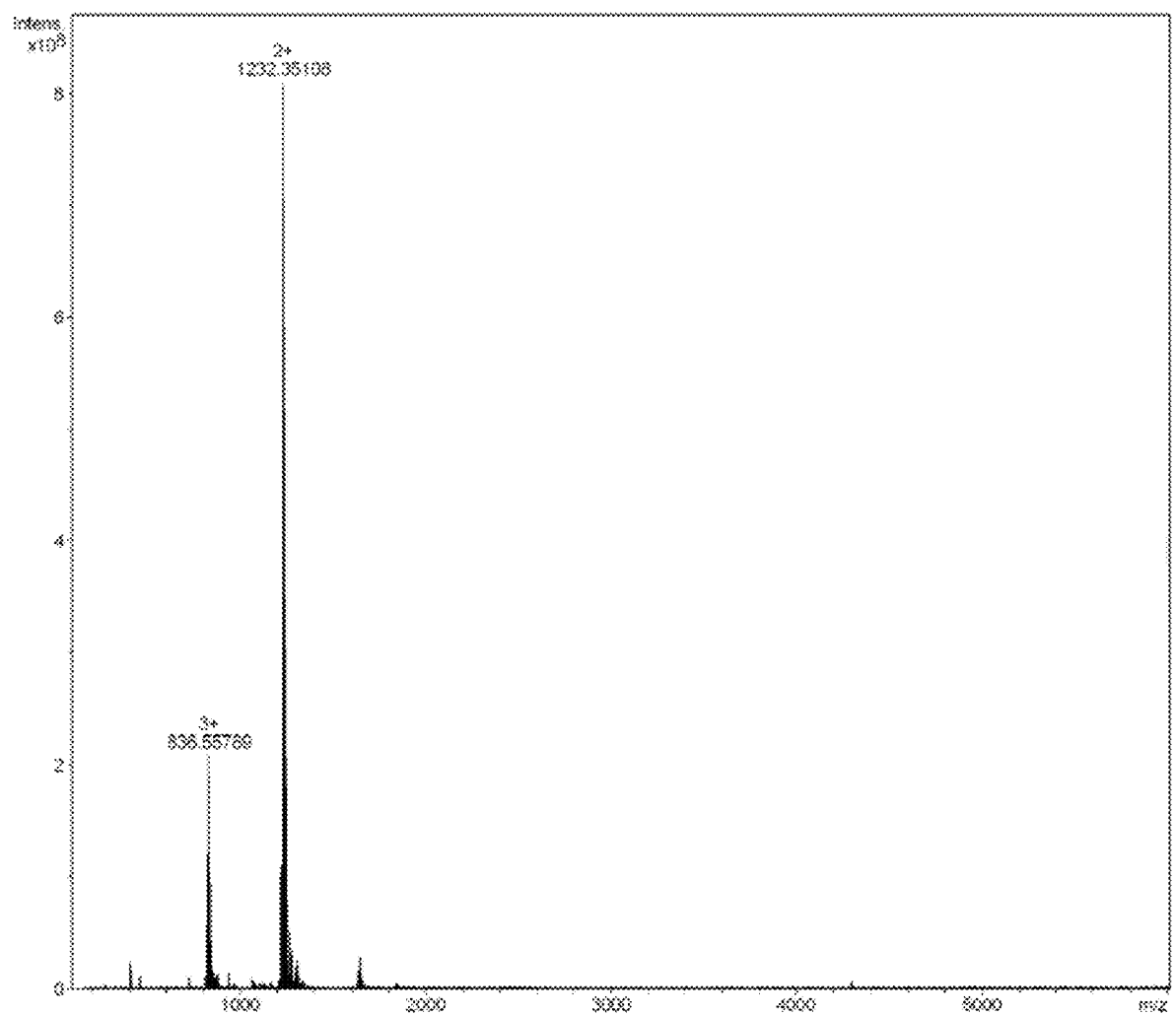
FIG. 1 is a high-resolution mass spectrum of Kylo-0101.

The following examples illustrate some embodiments disclosed in the present invention, but are not limited thereto. In addition, when providing specific embodiments, the inventors anticipated application of some specific embodiments, for example, compounds with specifically same or similar chemical structures for treatment of different liver-derived diseases.

Explanations pip refers to piperidine:

DMF refers to N,N-dimethylformamide;

Dde-Lys(Fmoc)-OH refers to N-1-(4,4-dimethyl-2,6-dioxocyclohexylidene)ethyl-N'-fluorenylmethoxycarbonyl-L-Lysine;

HBTU refers to O-benzotriazole-tetramethylurea hexafluorophosphate.

DIPEA (DIEA) refers to N,N-diisopropylethylamine;

Fmoc-Glu-OtBu refers to fluorenylmethoxycarbonyl-L-glutamic acid 1-tert-butyl ester;

TBTU refers to O-benzotriazole-N,N,N',N'-tetramethylurea tetrafluoroborate;

ACN refers to acetonitrile;

MTBE refers to methyl tert-butyl ether;

 refers to a solid phase carrier, such as a resin;

Unless otherwise specified, the ratio of two substances involved in this application refers to volume ratio;

Unless otherwise specified, the content involved in this application refers to volume percentage concentration.

Example 1: Preparation of Drug 1 (Kylo-0101)

(1) Compound 1-1 undergoes the following chemical reaction to produce Compound 1-2:

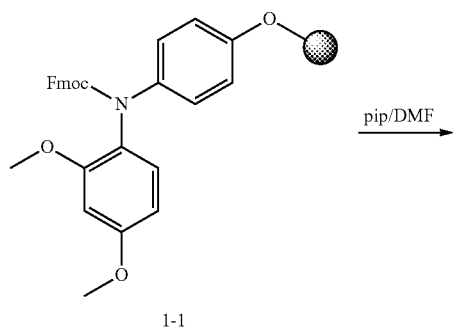

1-1

-continued

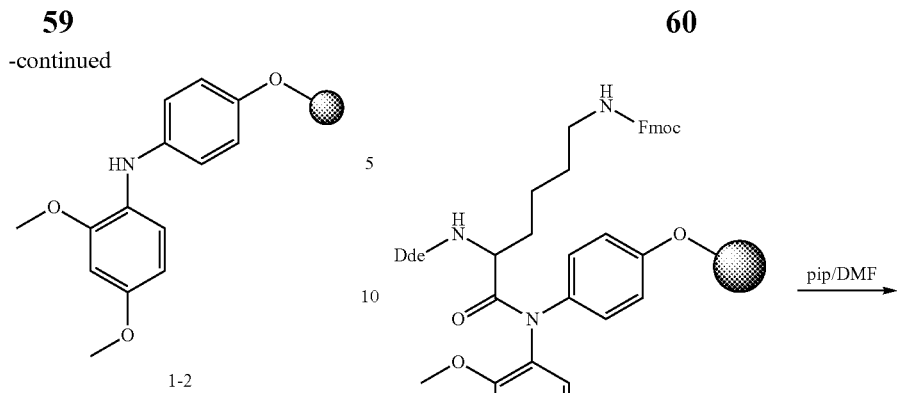

1-2

Compound 1-1 (0.31 g, 0.1 mmol) was weighed into a syntheisi tube, added with pip/DMF (2 ml/8 ml), bubbled with nitrogen for 30-40 min, and vacuumed out. Then Compound 1-2 was washed with DMF 3 times, 10 ml each time, to wash away pip and impurities produced by the reaction.

(2) Compound 1-2 undergoes the following chemical reaction to produce Compound 1-3:

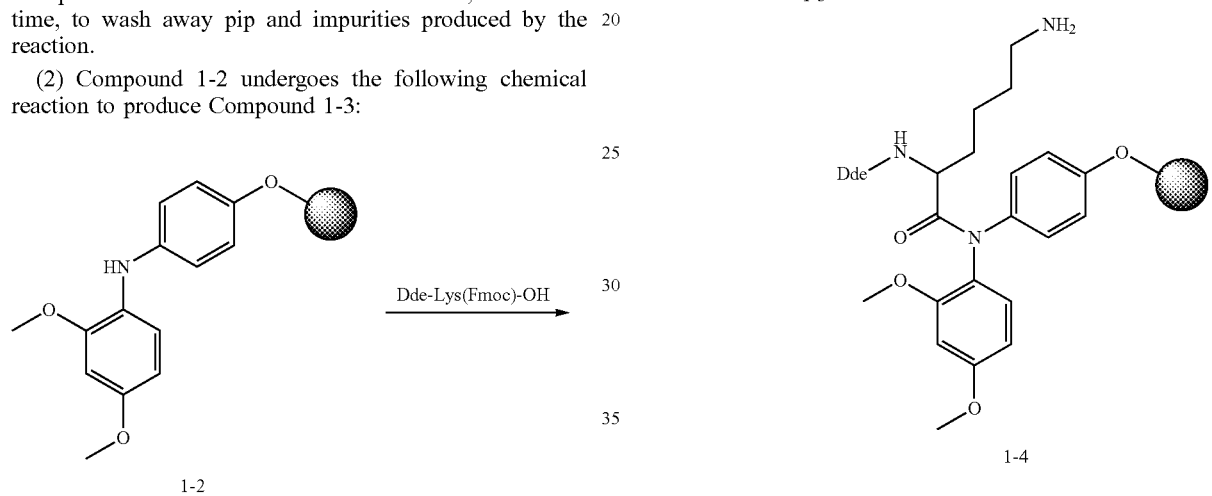

Dde-Lys(Fmoc)-OH (0.16 g, 0.3 mmol) and HBTU (0.114 g, 0.3 mmol) were weighed into a synthesis tube, added with DMF (10 mL) to dissolve the above solids, added with DIPEA (55 μL) and bubbled with nitrogen for 30-60 min. After removing the reaction liquid, the remaining solid compound 1-3 was washed with DMF 3 times, 10 ml each time, to remove HBTU, DIPEA and impurities produced by the reaction.

(3) Compound 1-3 undergoes the following chemical reaction to produce Compound 1-4:

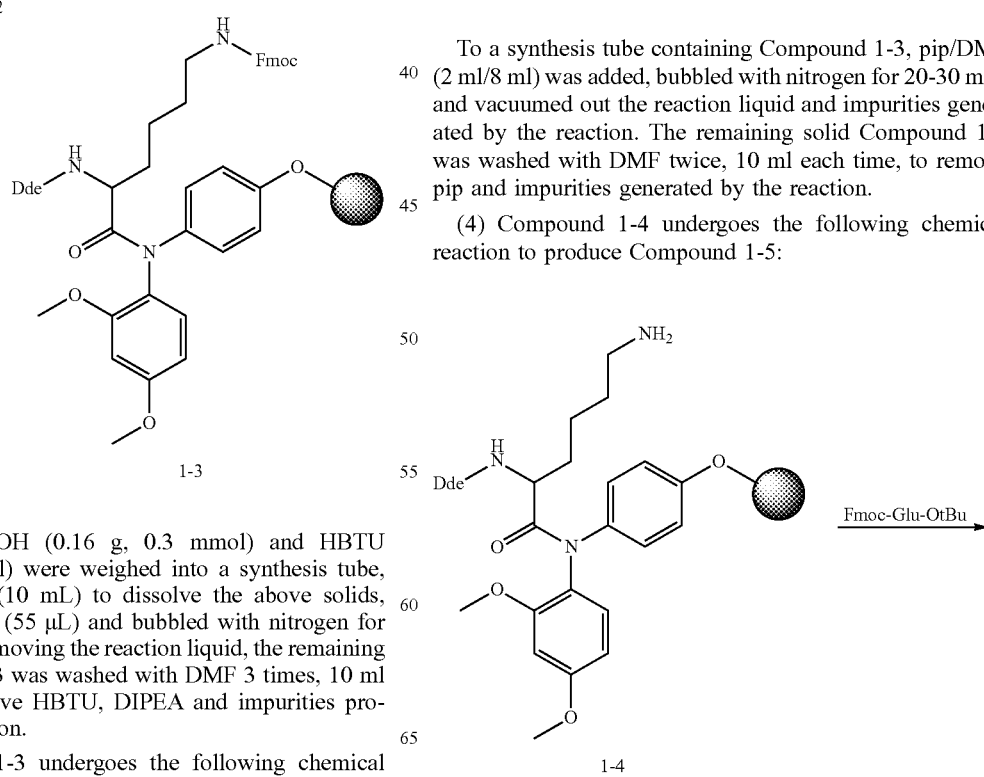

To a synthesis tube containing Compound 1-3, pip/DMF (2 ml/8 ml) was added, bubbled with nitrogen for 20-30 min, and vacuumed out the reaction liquid and impurities generated by the reaction. The remaining solid Compound 1-4 was washed with DMF twice, 10 ml each time, to remove pip and impurities generated by the reaction.

(4) Compound 1-4 undergoes the following chemical reaction to produce Compound 1-5:

-continued

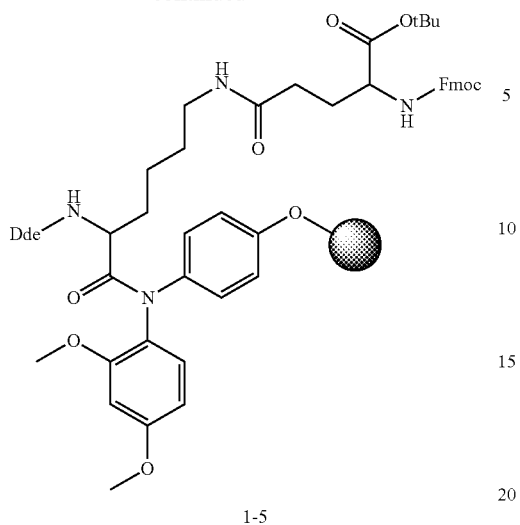

1-5

Fmoc-Glu-OtBu (0.13 g, 0.3 mmol) and HBTU (0.114 g, 0.3 mmol) were weighed into Compound 1-4 (0.1 mmol), added with DMF (10 mL) to dissolve the above solids, added with DIPEA (55 μL) and then bubbled with nitrogen for 15-30 min. After removing the reaction liquid, the remaining solid compound 1-5 was washed with DMF 3 times, 10 ml each time, to remove HBTU, DIPEA and impurities produced by the reaction.

(5) Compound 1-5 undergoes the following chemical reaction to produce Compound 1-6:

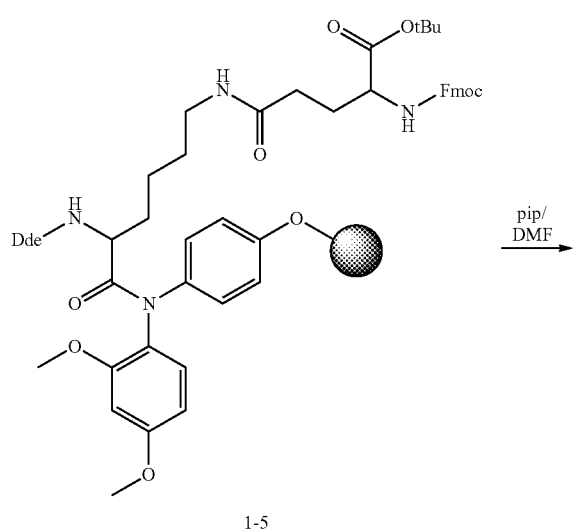

1-5

-continued

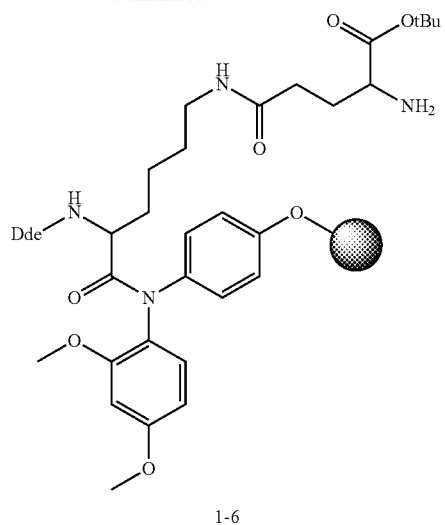

1-6

To Compound 1-5 (0.1 mmol), pip/DMF (2 ml/8 ml) was added, bubbled with nitrogen for 15-30 min, and vacuumed out the reaction liquid and impurities generated by the reaction. The remaining solid Compound 1-6 was washed with DMF 6 times, 10 ml each time, to remove pip and impurities generated by the reaction.

(6) Triiodothyronine undergoes the following chemical reaction to produce Compounds 1-7:

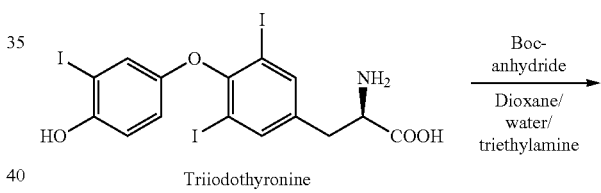

Triiodothyronine 1-7

0.5 g of triiodothyronine was weighed and put into an eggplant-shaped bottle, added with 4 ml of dioxane. 1 ml of purified water, 0.3 ml of triethylamine and 232 mg of Boc-anhydride, stirred for 2 h at room temperature protected from light, added with 4 ml of water and 10 ml of dichloromethane, adjusted pH to 4 by dropwise addition of hydrochloric acid, stood still to separate the layers. The water layer was added with 10 ml of dichloromethane to extract again. The combined organic layer was dried over 5 g of anhydrous sodium sulfate and filtered. The filtrate was concentrated to dryness with a rotary evaporator. The concentrate was added with 20 ml of petroleum ether, slurried and filtered. The filter cake was washed with 40 ml of petroleum ether and dried under reduced pressure to obtain 630 mg of Compound 1-7 (a white solid).

(7) Compound 1-6 undergoes the following chemical reaction to produce Compound 1-8:

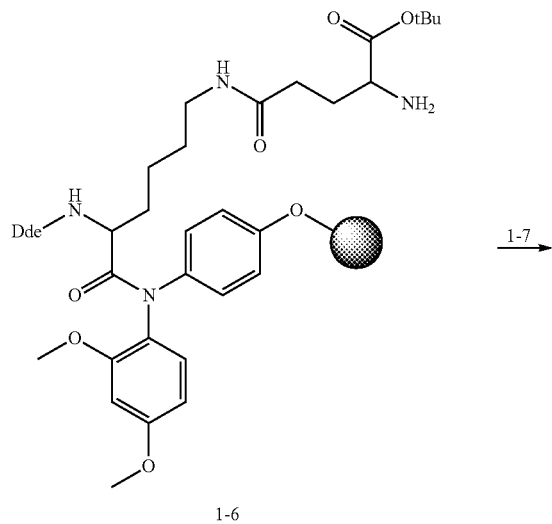

1-6

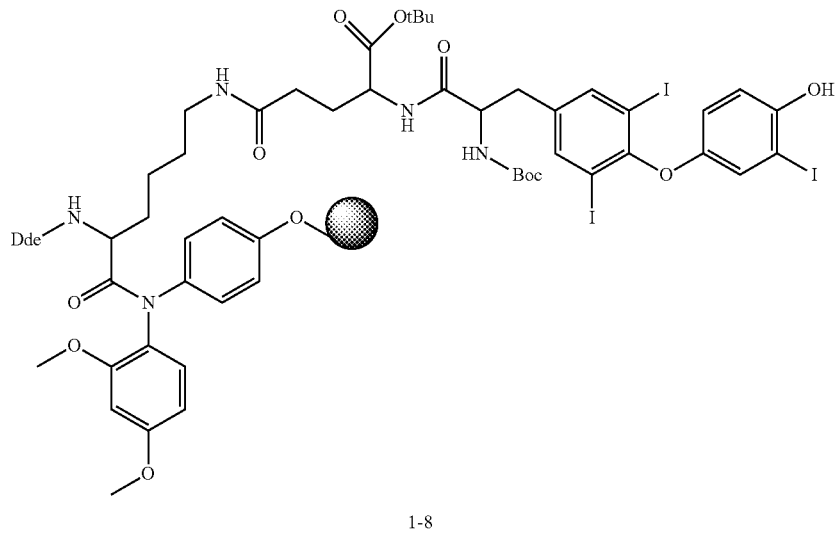

1-8

Compound 1-7 (0.23 g, 0.3 mmol) and HBTU (0.114 g, 0.3 mmol) were weighted and put into a synthesis tube containing 0.1 mmol of Compound 1-6, added with DMF (10 mL) to dissolve the above solids and then added with DIPEA (55 μL), and bubbled with nitrogen for 10-20 min. After removing the reaction liquid, the remaining compound 1-8 was washed with DMF 3 times, 10 ml each time, to remove HBTU, DIPEA and active esters produced by the reaction.

(8) Compound 1-8 undergoes the following chemical reaction to produce Compound 1-9:

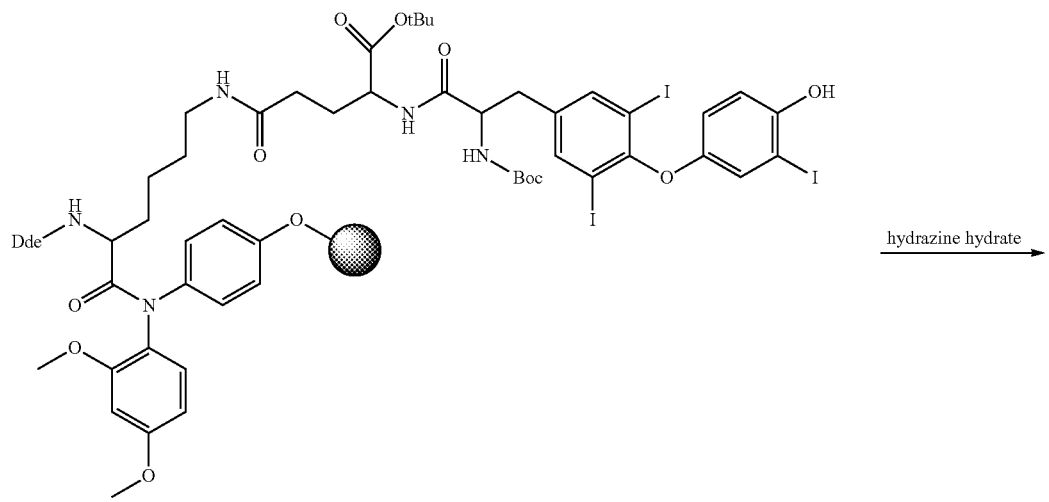

1-8

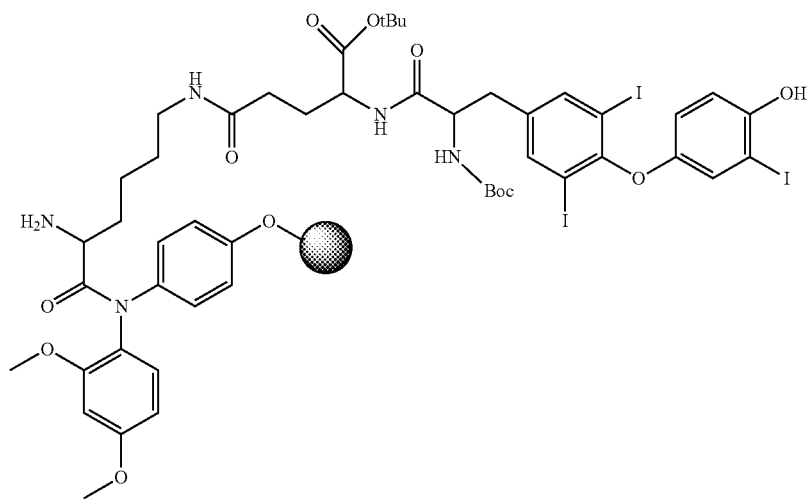

1-9

A solution of hydrazine hydrate/DMF (0.2 ml/9.8 ml) was added to Compound 1-8 (0.1 mmol), and bubbled with nitrogen for 10 min. The DMF solution of hydrazine hydrate was removed under vacuum, and Compound 1-9 was washed with DMF 6 times, 10 ml each time, to remove hydrazine hydrate and impurities produced by the reaction.

(9) Preparation of compound 1-10:
Step One:

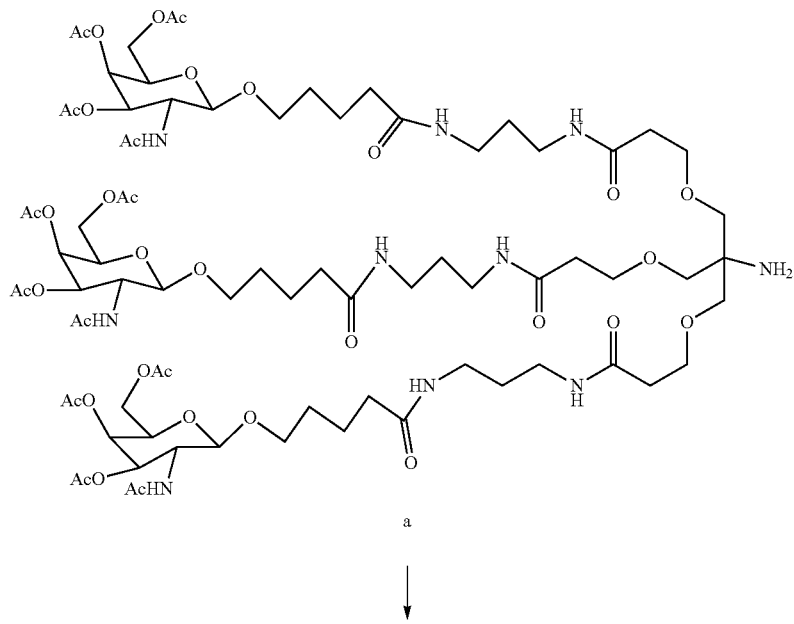

a

↓

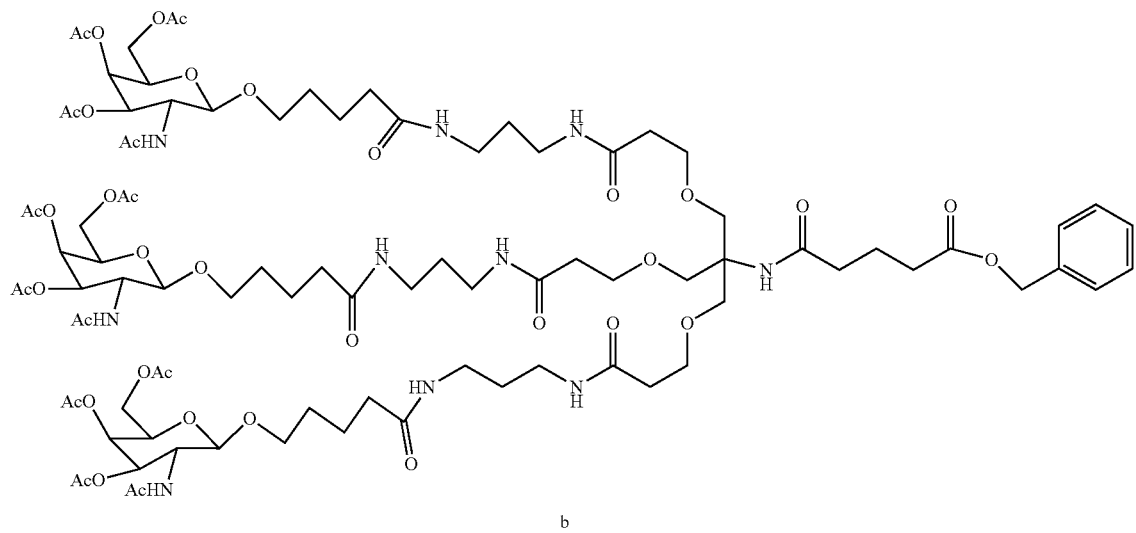

b 0.21 g of 1,5-glutaric acid monobenzyl ester was weighed and dissolved in 2 ml of DMF, added with 0.36 g of TBTU and 0.4 ml of DIEA, and stirred and reacted for 5 min. 1.09 g of Compound a was dissolved in 10 ml of DMF, and slowly added into the above reaction solution. The reaction solution was stirred overnight at room temperature, evaporated to dryness under reduced pressure, added with 40 ml of dichloromethane and 20 ml of water, stirred for 15 min and layered. The organic layer was dried over 10 g of anhydrous sodium sulfate, and passed through a chromatography column (eluent: dichloromethane:methanol=1%-10%). The target compound b to be collected was identified by thin Layer chromatography (the developing solvent contains dichloromethane and methanol in a volume ratio of 10:1). The eluent containing the pure Compound b was collected and evaporated off the solvent under reduced pressure to obtain 0.85 g of Compound b as a white product.

Step Two:

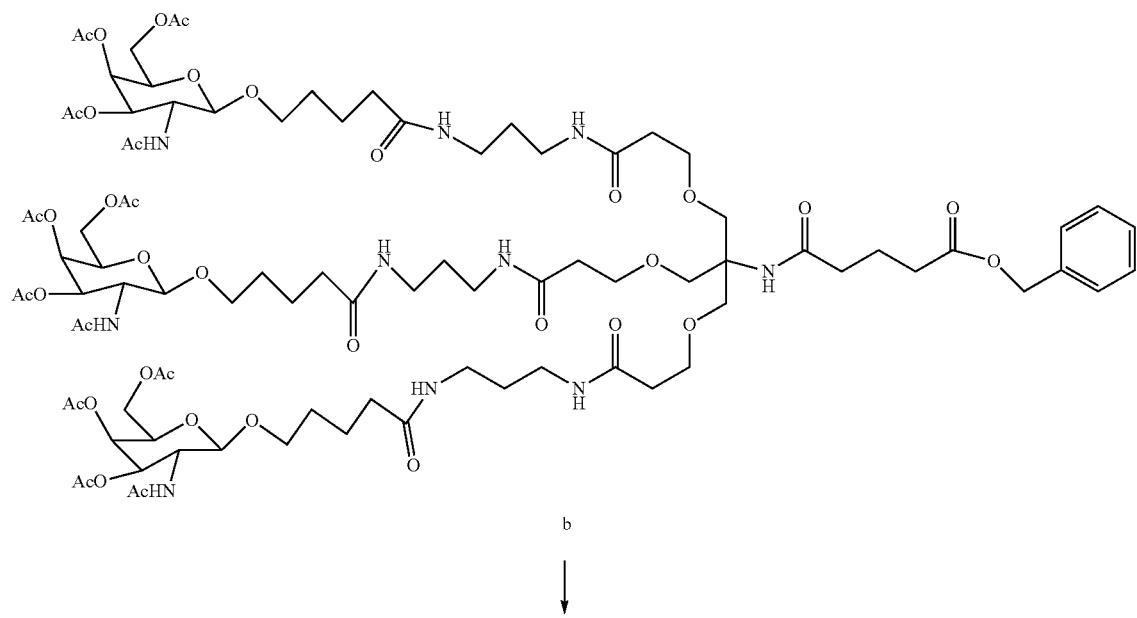

b

↓

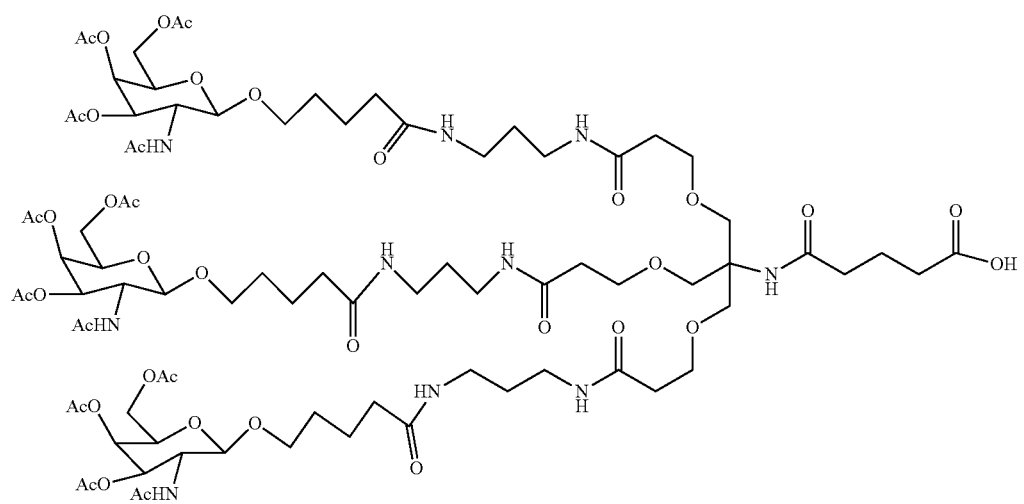

1-10

0.85 g of Compound b was put into a 100 ml single-necked flask, added with 127 mg of palladium-carbon, cammed with a water pump and supplemented with hydrogen, repeating for three times, and then pressed with hydrogen and reacted overnight. On the second day, TLC of the reaction mixture showed no compound b. The reaction mixture was filtered (aided with 12 g of diatomite), and the filtrate was evaporated under reduced pressure to obtain 90.76 g of Compound 1-10.

(10) Compound 1-9 and Compound 1-10 undergo the following chemical reaction to produce Compound 1-11:

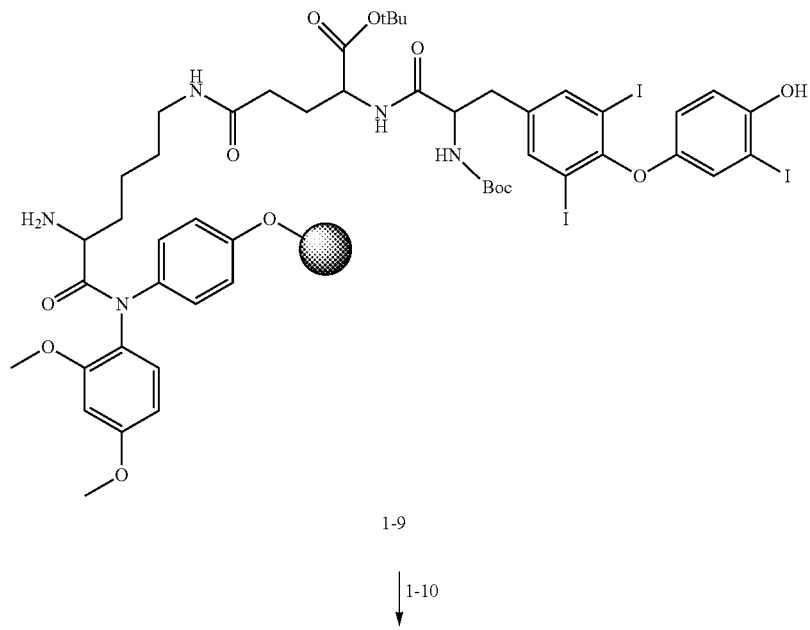

1-9

↓ 1-10

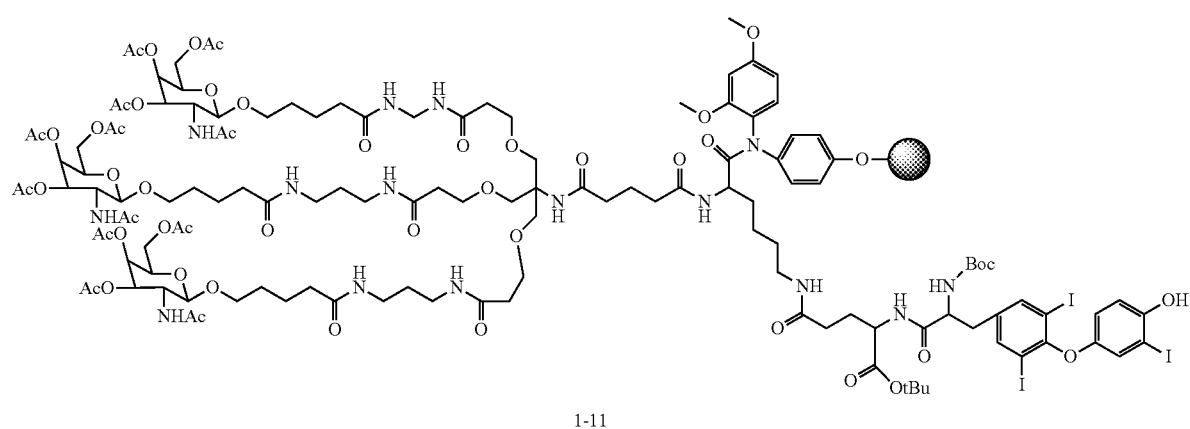

1-11

Compound 1-10 (0.57 g, 0.3 mmol) and HBTU (0.114 g, 0.3 mmol) were weighed and put into a synthesis tube containing Compound 1-9 (0.1 mmol), added with DMF (10 mL) to dissolve the above solids, added with DIPEA (55 μL) and bubbled with nitrogen for 10-20 min. The reaction liquid was removed and the remaining Compound 1-11 was washed with DMF, 10 ml each time.

(11) Compound 1-11 undergoes the following chemical reaction to produce Compound 1-12:

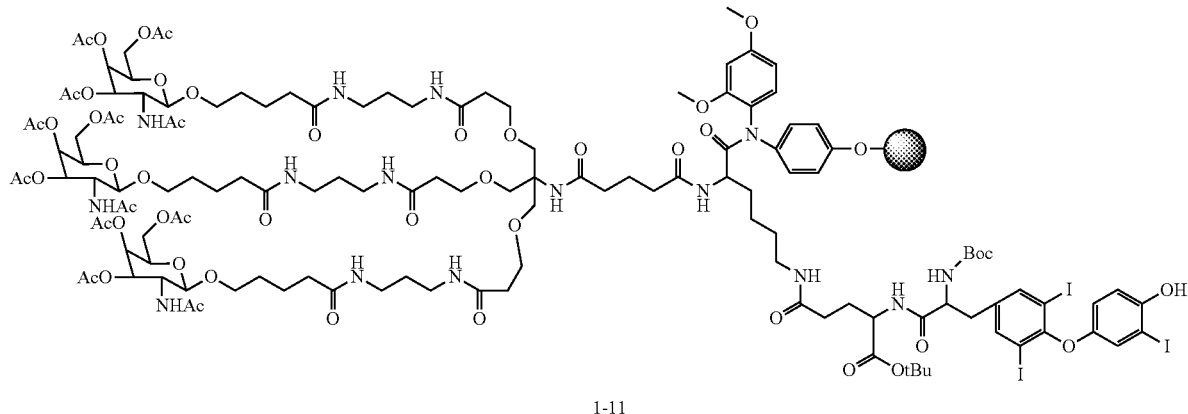

1-11

↓ F solution

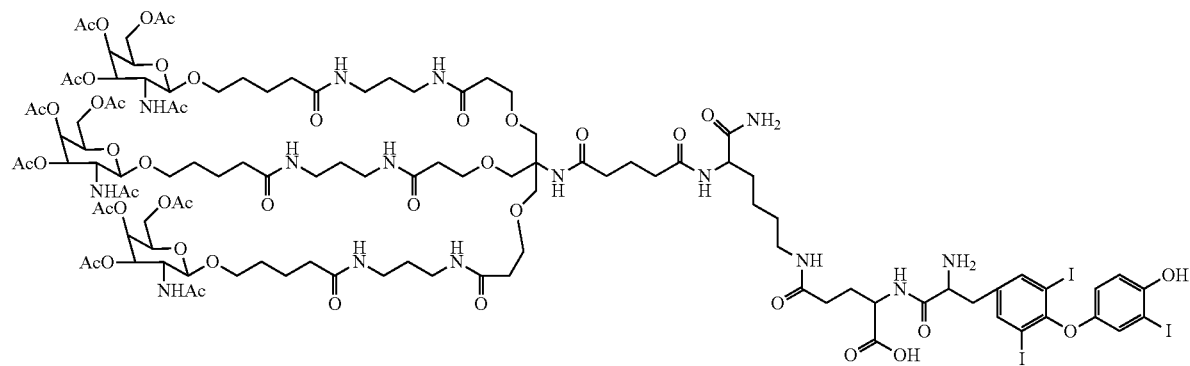

1-12

F solution (6 ml, trifluoroacetic acid:triisopropylsilane:water=90:3.5:5.5) was slowly poured into a centrifuge tube containing Compound 1-11 (0.3 g, 0.05 mmol), took out after cutting for 1 hour while controlling temperature at 30-35° C. and rotation speed at 200 r/min, and filtered to remove the solid. The filtrate (5 ml) was slowly poured into MTBE (20 ml), and the suspension was centrifuged with a centrifuge at 3000 r/min. The solid was dispersed again with MTBE (20 ml), and the suspension was centrifuged again. The solid was collected and vacuum dried for 1 hour to obtain 46 mg of a white powder with a yield of 34% calculated based on Compound 1-11.

The resultant white powder was dissolved in 2 ml of ACN/water (0.2 ml/1.8 ml) and loaded on a column using a filler with a trade name of GE Resource 15RPC (50 ml) and a mobile phase being a mixture of water and acetonitrile (acetonitrile content is 10% to 90%) to carry out gradient elution. All products were collected and lyophilized to obtain 12 mg of the pure compound 1-12.

(12) Compound 1-12 undergoes the following chemical reaction to produce the drug 1 (Kylo-0101):

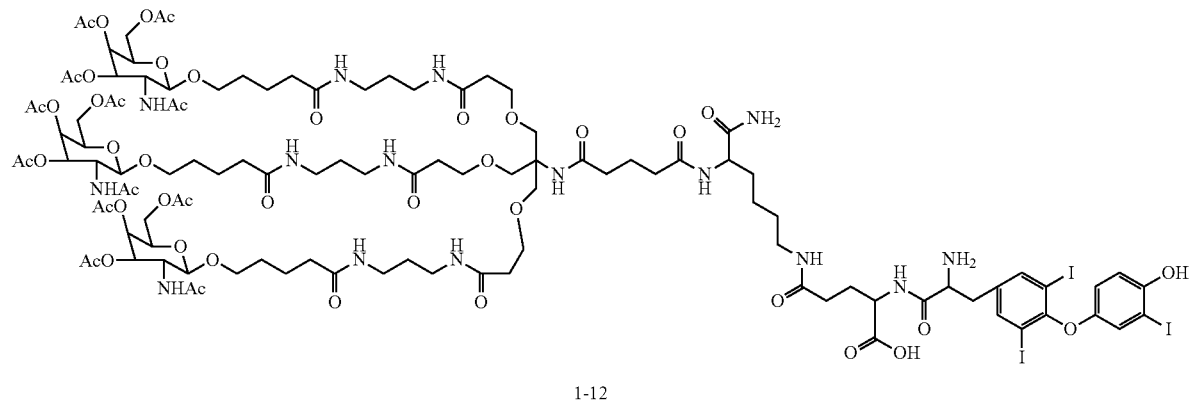

1-12

↓ CH₂ONa

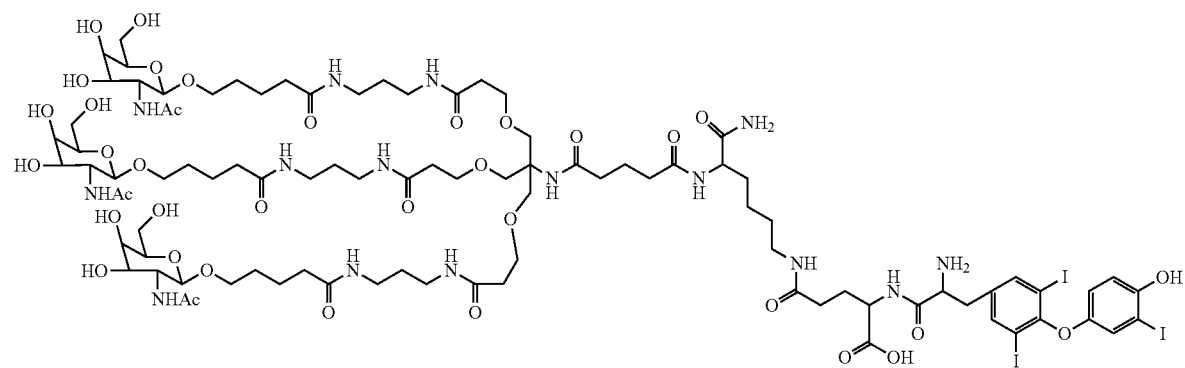

1

A solution of sodium methoxide/methanol (20 mg/ml) was added into the lyophilized compound 1-12 (12 mg, 0.0043 mmol), shook for 20 min while setting shaker temperature at 30-35° C. and rotation speed at 200 r/min, adjusted pH to 7 fay addition of 1 mol/L HCl (5-7 drops), and rotary evaporated to remove the solvent with a water bath at a temperature of 40-45° C. The residue was dissolved in 2 ml of ACN/water (0.2 ml/1.8 ml), and loaded on a column using a filler with a trade name of GE Resource 15RPC (10 ml) and a mobile phase being a mixture of water and acetonitrile (acetonitrile content is 10% to 90%) to carry out purification. All eluted products were collected and lyophilized to obtain 7 mg of the pure drug 1 (Kylo-0101) with a yield of 67.3%. As shown in FIG. 1, the target peak is 1232.35108(2+) when the mass-to-charge ratio is 2 in mass spectrometry of Kylo-0101.

Example 2: Preparation of Drug 2 (Kylo-0102)

Compound 2-1 undergoes the following chemical reaction to produce Drug 2 (Kylo-0102):

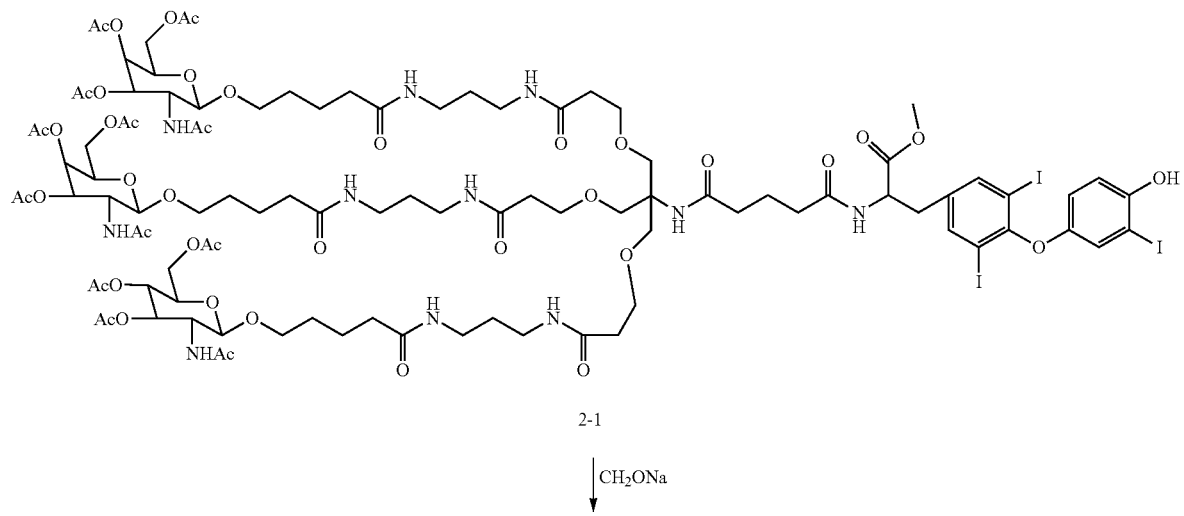

2-1

↓ CH₂ONa

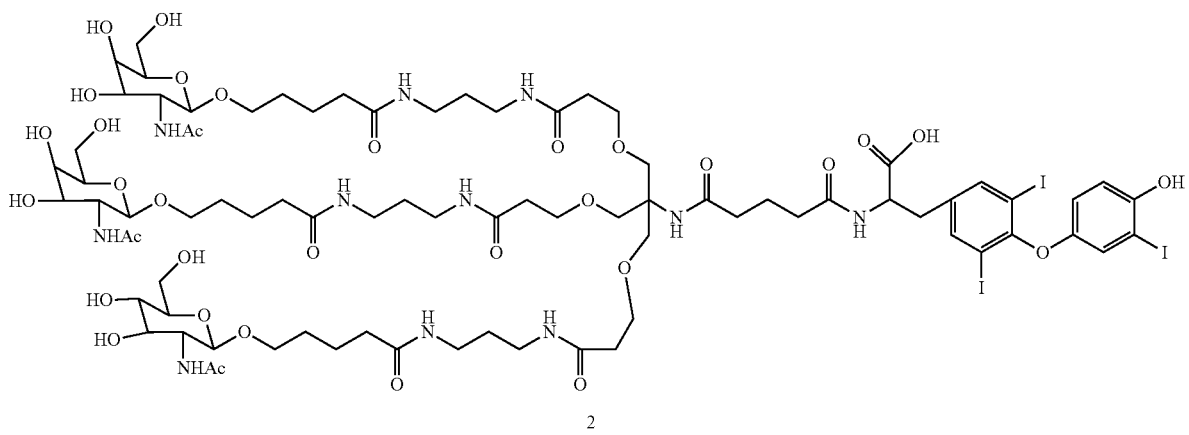

2

Figure 2:
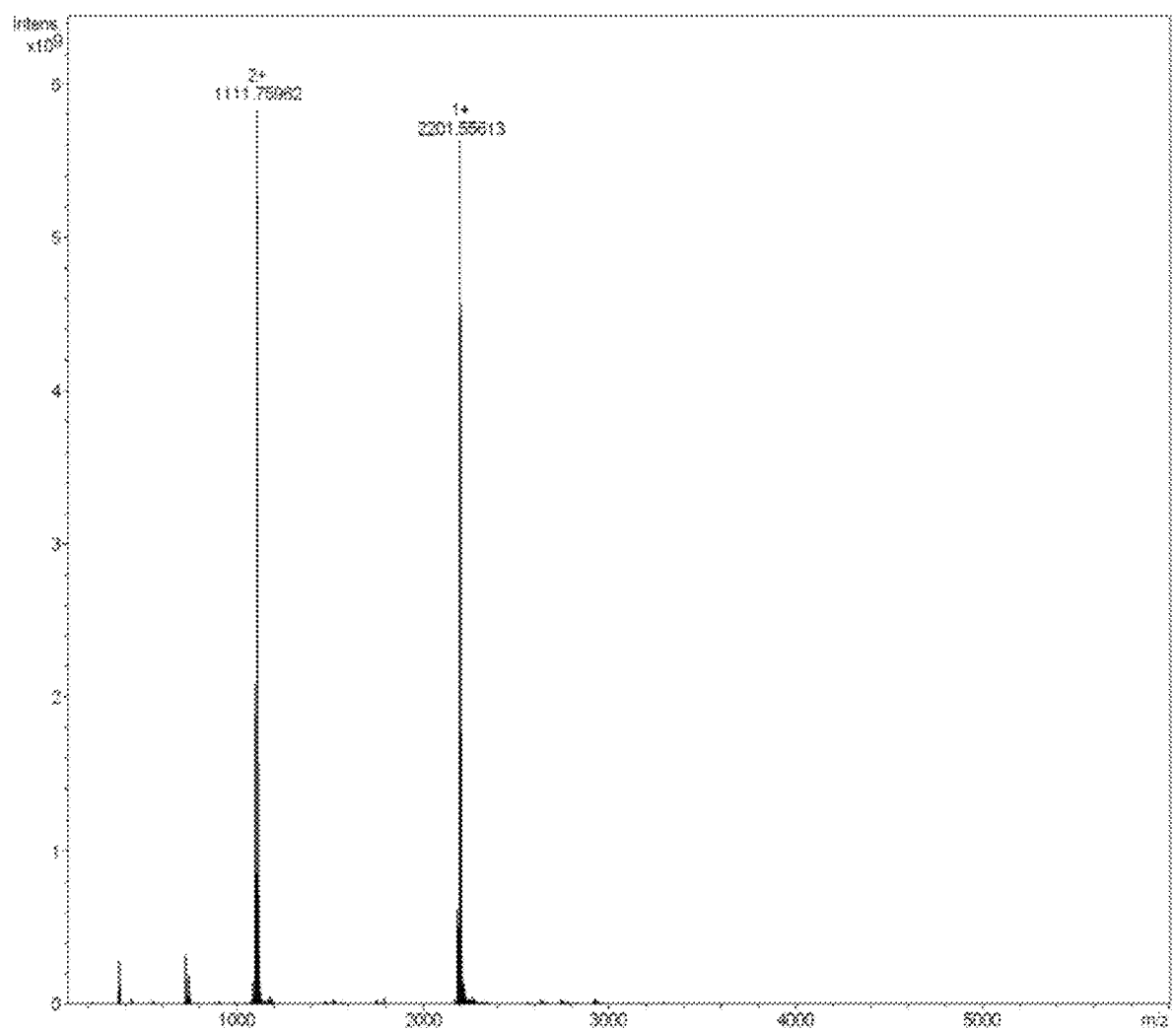
FIG. 2 is a high-resolution mass spectrum of Kylo-0102.

A solution of sodium methoxide/methanol (20 mg/5 ml) was added into Compound 2-1 (20 mg, 0.0078 mmol), shook for 30 min while setting shaker temperature at 30-35° C. and rotation speed at 200 r/min. adjusted pH to 7 by addition of 1 mol/L HCl (5-7 drops), and rotary evaporated to remove the solvent with a water bath at a temperature of 40-45° C. The residue was dissolved in ACN/water (0.2 ml/1.8 ml), and loaded on a column using a filler with a trade name of GE Resource 15RPC (10 ml) and a mobile phase being a mixture of water and acetonitrile (acetonitrile content is 10% to 90%) to carry out purification. All eluted products were collected and lyophilized to obtain 12 mg of the pure drug 2 (Kylo-0102) with a yield of 71.1%. As shown in FIG. 2, the target product is 2201.55613(1+) when the mass-to-charge ratio is 1, and 1111.75962(2+) when the mass-to-charge ratio is 2 in mass spectrometry of Kylo-0102.

Example 3: Preparation Method of Drug 3 (Kylo-0103)

Compound 3-1 undergoes the following chemical reaction to produce Drug 3 (Kylo-0103):

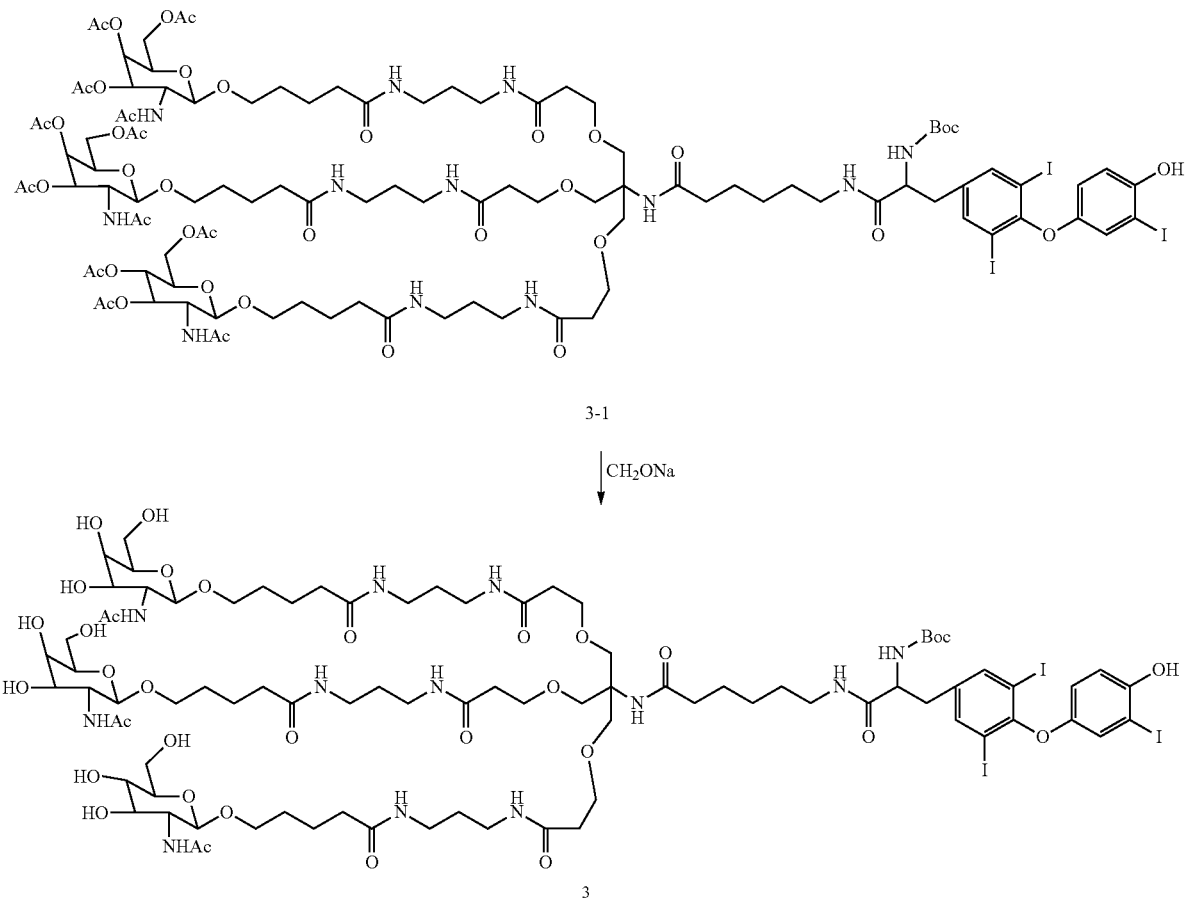

3

Figure 3:
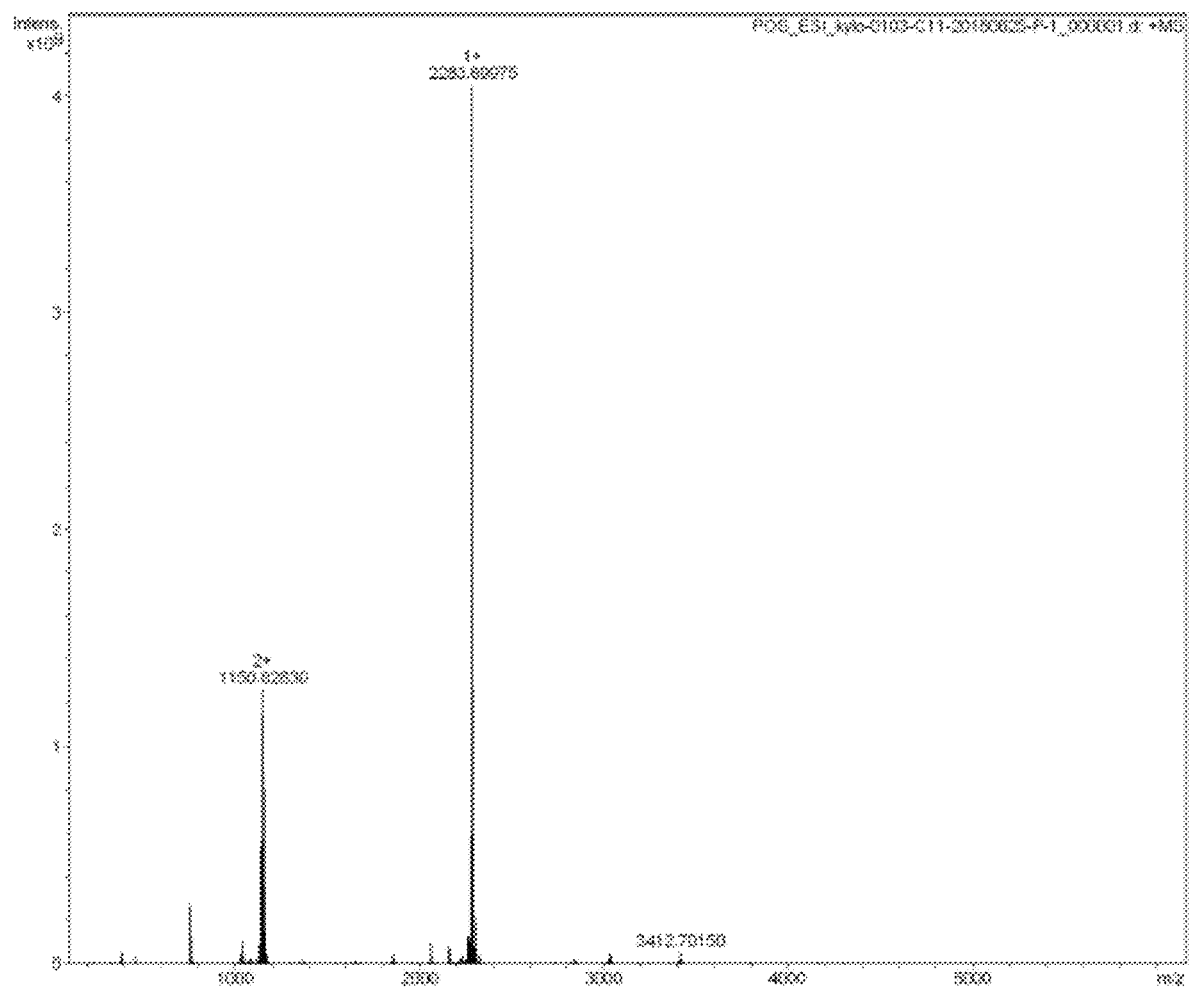
FIG. 3 is a high-resolution mass spectrum of Kylo-0103.

A solution of sodium methoxide/methanol (20 mg/5 ml) was added into Compound 3-1 (20 mg, 0.0076 mmol), shook for 30 min while setting shaker temperature at 30-35° C. and rotation speed at 200 r/min, adjusted pH to 7 by addition of 1 mol/L HCl (5-7 drops), and rotary evaporated to remove the solvent with a water bath at a temperature of 40-45° C. The residue was dissolved in ACN/water (0.2 ml/1.8 ml), and loaded on a column using a filler with a trade name of GE Resource 15RPC (10 ml) and a mobile phase being a mixture of water and acetonitrile (acetonitrile content is 10% to 90%) to carry out purification. All eluted products were collected and lyophilized to obtain 12.5 mg of the pure drug 3 (Kylo-0103) with a yield of 72.7%. As shown in FIG. 3, the target product is 2283.69975(1+) when the mass-to-charge ratio is 1 in mass spectrometry of Kylo-0102.

Example 4: Animal Experiment 1

Materials: 30 genetically obese model mice (db/db mice) (6 weeks old, male, SPF level, provided by Nanjing University-Nanjing Institute of Biomedicine with a production license NO. SCXK (SU) 2015-0001, an animal certificate NO. 201820469 and a use license NO. SCXK(SU)2018-0027) were selected as the administration group. The mice needed to adapt to the environment before the experiment, and healthy mice were selected as test animals, and reared in IVC cages at a density of 5 animals/cage with the litter being changed twice a week. Requirements on Laboratory animal room: room temperature 22 to 24° C., relative humidity 40 to 70%, automatic lighting, 12 h alternating light and dark (lights were tinned on at 08:00, and turned off at 20:00), the standard of laboratory animal room meets the national standard of the People's Republic of China GB14925-2010.

Experimental Drugs: see Table 1.

TABLE 1

| Experimental drug | Lot number | Source |
|---|---|---|
| Kylo-0101 | 20180607 | Kylonova (Xiamen) |
| Kylo-0102 | 20180622 | Biopharma Co., Ltd. |
| Kylo-0103 | 20180626 | |
| Kylo-0100 | 20180612 | |
| Storage precautions: frozen storage (−20° C.) | | |

Remarks: Kylo-0100 is T3 as a positive control drug, the experimental drugs were dissolved in saline.

Preparation of anesthetic of xylazine combined with ketamine: the concentrations of xylazine and ketamine in the mixed solution were 10 mg/ml and 0.5 mg/ml respectively.

The grouping and dosing schedule are shown in Table 2.

TABLE 2

| Mouse type | Number | Experimental drug | Administration manner | Dose |
|---|---|---|---|---|
| Control group | 6 | Saline | Subcutaneous injection | 150 μL/mouse |

TABLE 2-continued

| Mouse type | Number | Experimental drug | Administration manner | Dose |
|---|---|---|---|---|
| Adminis- | 6 | Kylo-0100 | The injection | 13.5 μg/kg |
| tration | 6 | Kylo-0101 | volume is | 48.4 μg/kg |
| group | 6 | Kylo-0102 | 150 μL/ | 43.3 μg/kg |
|  | 6 | Kylo-0103 | mouse/day | 43.3 μg/kg |

The body weight was weighed twice a week, and the administration was carried out continuously for 21 days. After the last administration, the mice were fasted overnight for 15-16 hours, sacrificed by $CO_2$ anesthesia. The blood was collected by cardiac puncture, left to stand at room temperature for 2 hours, and centrifuged on a low temperature centrifuge at 3000 RPM for 10 minutes to collect serum, which was then stored in a −80° C. refrigerator for later use. The contents of total cholesterol (TC), low-density lipoprotein (LDL) and triglyceride (TG) in the serum were measured on a blood biochemical analyzer.

On the 18th day of the administration, the mice were intraperitoneally injected with the anesthetic (xylazine combined with ketamine, 10 ml/Kg, IP), and the bone mineral density and body fat ratio of the mice were measured on a bone density meter.

Figure 4:
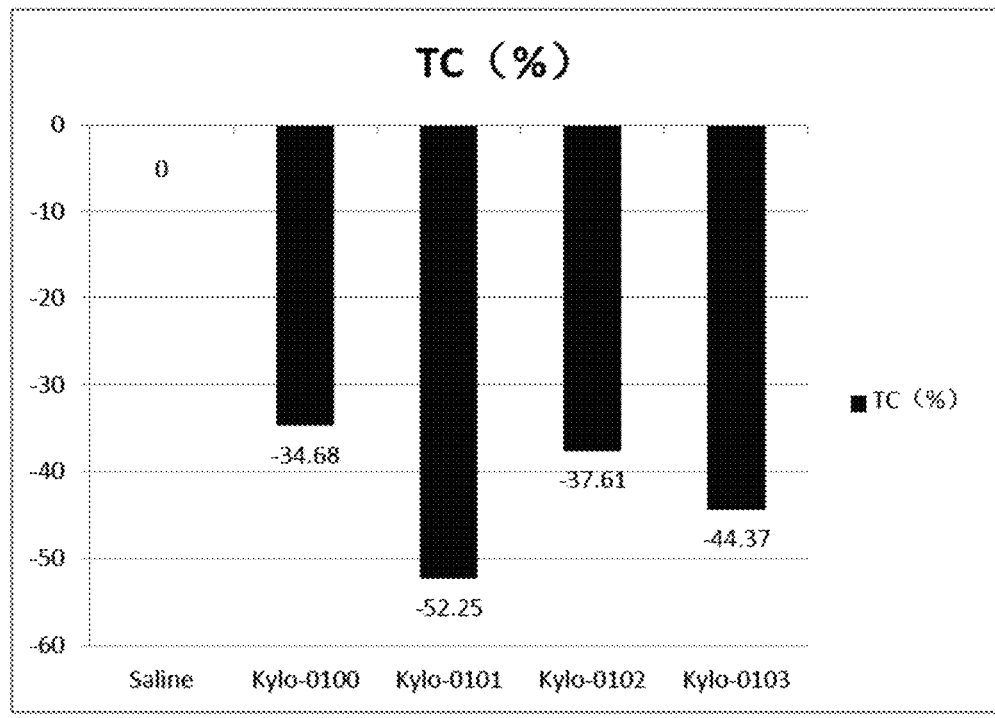
FIG. 4 shows detection results of total cholesterol (TC) content in the serum of db/db mice in Example 4.

The experimental data in FIG. 4 shows that the serum TC levels of the mice in the Kylo-0100 to Kylo-0103 administration groups were significantly lower than that of the saline control group, and the reduction rates reached 34.68%, 52.25%, 37.61% and 44.37%, respectively.

Figure 5:
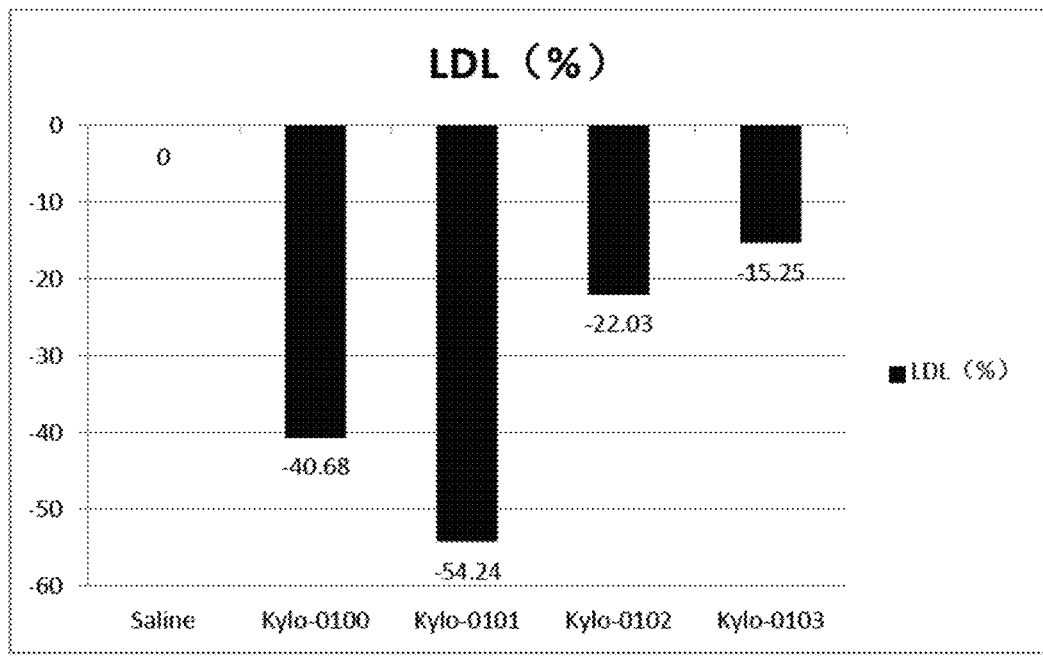
FIG. 5 shows detection results of low-density lipoprotein (LDL) content in the serum of db/db mice in Example 4.

The experimental data in FIG. 5 shows that the serum LDL levels of the mice in the Kylo-0100 to Kylo-0103 administration groups were significantly lower than that of the saline control group, and the reduction rates reached 40.68%, 54.24%, 22.03% and 15.25%, respectively.

Figure 6:
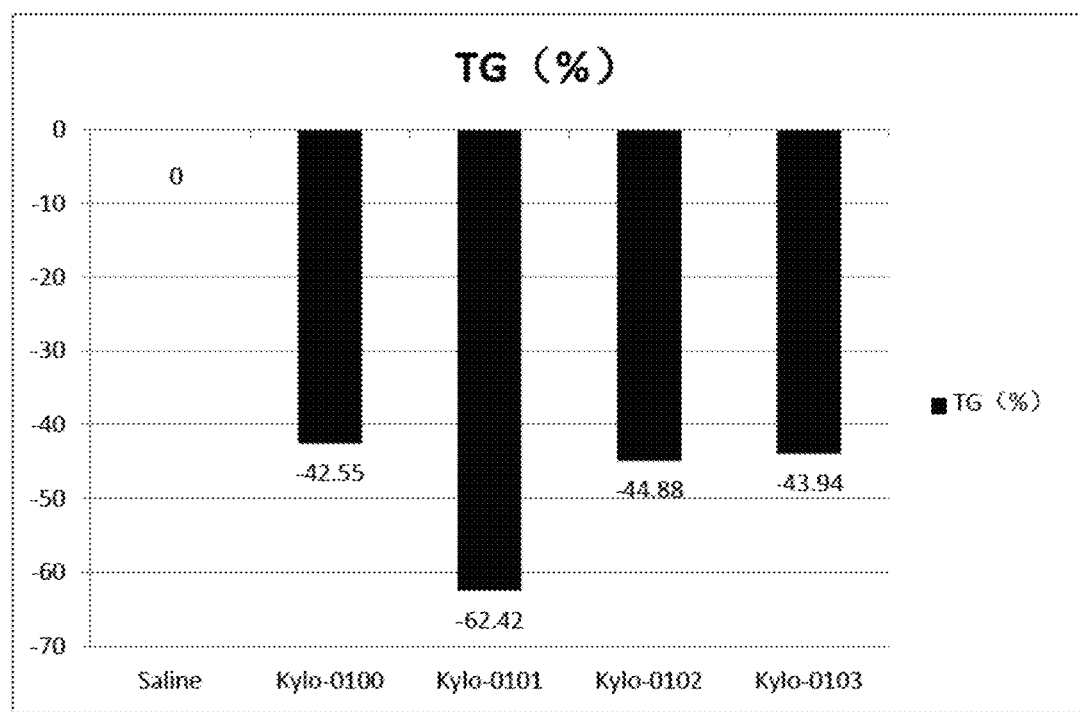
FIG. 6 shows detection results of triglyceride (TG) content in the serum of db/db mice in Example 4.

The experimental data in FIG. 6 shows that the serum TG levels of the mice in the Kylo-0100 to Kylo-0103 administration groups were significantly lower than that of the saline control group, and the reduction rates reached 42.55%, 62.42%, 44.88% and 43.94%, respectively.

Figure 7:
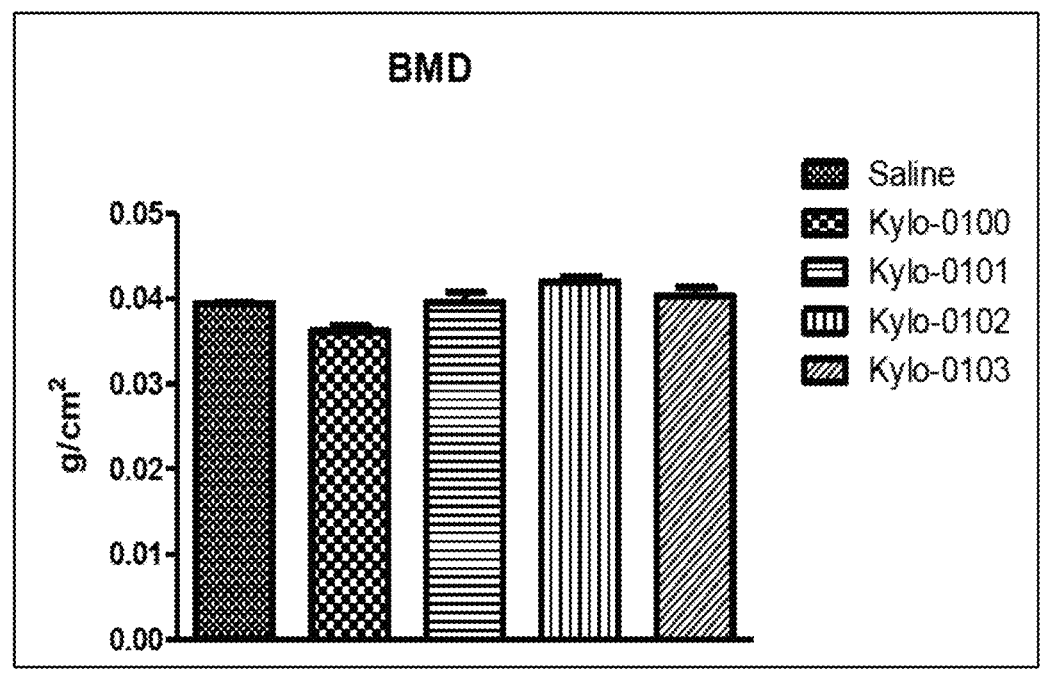
FIG. 7 shows detection results of bone mineral density (BMD) in db/db mice in Example 4.

The experimental data in FIG. 7 shows that the bone mineral density (BMD) of the mice in the Kylo-0100 administration group was significantly lower than that of the saline control group; and the bone mineral density of the mice in the Kylo-0101 administration group was basically no change compared to the saline control group.

Figure 8:
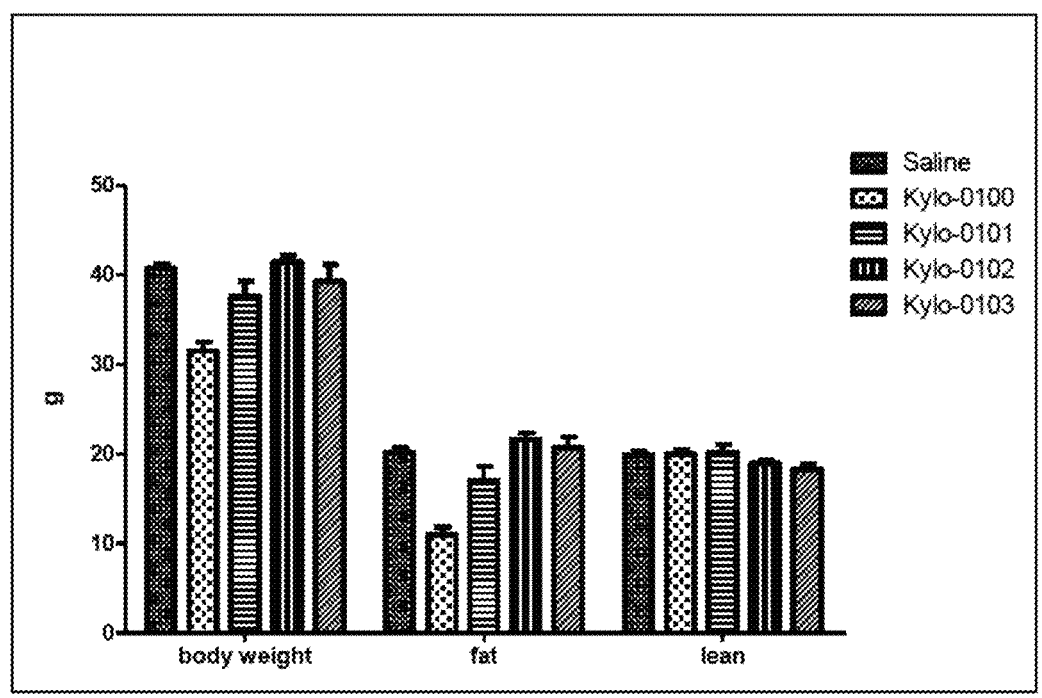
FIG. 8 shows effects of experimental drugs on body weight, hit mass and lean mass of db/db mice in Example 4.

The experimental data in FIG. 8 shows that Kylo-0100 has a significant effect on the body weight of mice, and Kylo-0101 has no obvious effect on the body weight of mice, indicating that Kylo-0101 mainly acts in the liver and does not produce adverse effects on mice as a whole.

Example 5: Animal Experiment 2

Animals and feeding: 36 male 6-week-old genetically obese mouse models (db/db mice) and 5 wild type littermates (provided by Nanjing University-Nanjing Institute of Biomedicine with a production license NO. SCXK (SU) 2015-0001, an animal certificate NO. 201826897 and a use license NO. SCXK(SU)2018-0027) were selected as the administration group.

The mice needed to adapt to the environment before the experiment, and healthy mice were selected as test animals, and reared in IVC cages at a density of 5 animals/cage with the litter being changed twice a week. Requirements on Laboratory animal room: room temperature 22 to 24° C., relative humidity 40 to 70%, automatic lighting, 12 h alternating light and dark (lights were turned on at 08:00, and turned off at 20:00), the standard of laboratory animal room meets the national standard of the People's Republic of China GB14925-2010.

The experimental drugs are shown in Table 3.

TABLE 3

| No. | experimental drug | Lot number | Source |
|---|---|---|---|
| 1 | Kylo-0101 | 20180828 | Kylonova (Xiamen) |
| 2 | Kylo-0100 | 20180612 | Biopharma Co.,Ltd. |

Preparation of anesthetic of xylazine combined with ketamine: the concentrations of xylazine and ketamine in the mixed solution were 10 mg/ml and 0.5 mg/ml respectively.

The grouping and dosing schedule are shown in Table 4.

TABLE 4

| Group | Number | Group No. | Dose of experimental drug (μg/kg) | Administration volume (ml/kg) | Intervention method |
|---|---|---|---|---|---|
| Wild type control group | 5 | Group 1 (G1) | saline | 5 | Subcutaneous injection once a day |
| Model control group | 6 | Group 2 (G2) | saline | 5 |  |
| Kylo-0100 Administration group | 6 | Group 3 (G3) | 65 | 5 |  |
| Kylo-0101 Administration group | 6 | Group 4 (G4) | 1 | 5 |  |
|  | 6 | Group 5 (G5) | 3 | 5 |  |
|  | 6 | Group 6 (G6) | 10 | 5 |  |
|  | 6 | Group 7 (G7) | 30 | 5 |  |

Remarks: the administrated drug was dissolved in saline.

Experimental design: Before starting the experiments, the mice were weighed and randomly grouped according to body weight. The mice were weighed every Monday and Thursday. On the 18th day of administration, the mice were anesthetized by intraperitoneal injection of the anesthetic (xylazine combined with ketamine, 10 ml/kg, IP), and the bone mineral density and body hit ratio of the mice were measured. The administration was carried out continuously for 21 days.

After the last administration, the mice were fasted overnight for 15-16 hours, sacrificed by $CO_2$ anesthesia. The whole blood was collected by cardiac puncture, and left to stand at room temperature for 2 hours to collect serum. The serum is divided into three parts. One part (100 μl) was used for detecting blood glucose, triglycerides (TG), total cholesterol (TC), low-density lipoprotein (LDL) and high-density lipoprotein (HDL-C), alanine aminotransferase (ALT), aspartate aminotransferase (AST) and phosphatase (AP) levels in the serum. The remaining two parts were divided equally for detecting contents of triiodothyronine (bonded and free T3), thyroxine (bonded and free T4), and TSH (thyroid stimulating hormone).

The weights of the liver and the heart were weighted. The liver is divided into three parts. One part is frozen in liquid nitrogen, one part is fixed with 10% neutral formaldehyde, and the other part is frozen and embedded in OCT (a water-soluble mixture of polyethylene glycol and polyvinyl alcohol).

Tissue analysis and pathological examination: the liver tissue was homogenized with isopropanol at a mass-to-volume ratio of 1:9, left to stand overnight, and centrifuged to collect the supernatant. The contents of TC and TG in the supernatant were detected by blood biochemistry. The liver tissue immersed in 10% neutral formaldehyde is routinely embedded in paraffin, sectioned (3 μm) and stained with hematoxylin-eosin (HE), and then dehydrated and sealed to observe the liver lesions and perform whole slide imaging. The liver tissue immersed in OCT was frozen and sectioned (5 μm), stained with oil red, stained nucleus with hematoxylin, dehydrated and sealed to observe the lipid deposition of liver tissue and take pictures. The liver frit accumulations of the administration group and the model control group were compared.

Statistical analysis: The quantitative indexes were expressed by Mean±sem, and the differences between the model control group and the rest of the groups were compared by T test (TTest2.3). All the statistical analyses were completed in Excel table.

Figure 9:
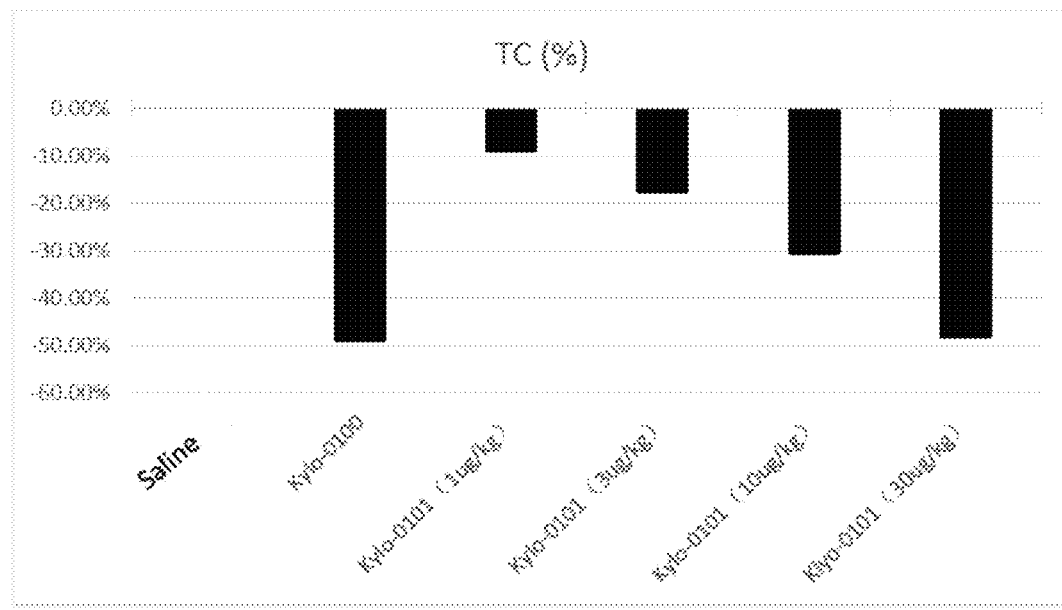
FIG. 9 shows effects of Kylo-0101 at different doses on TC level in the serum of db/db mice in Example 5.

The experimental data in FIG. 9 shows that the TC levels in the serum of the mice in the respective Kylo-0101 dose groups were reduced, and there was a significant dose-effect relationship. At a dose of 30 μg/kg, the TC level in the serum was reduced by to 48%.

Figure 10:
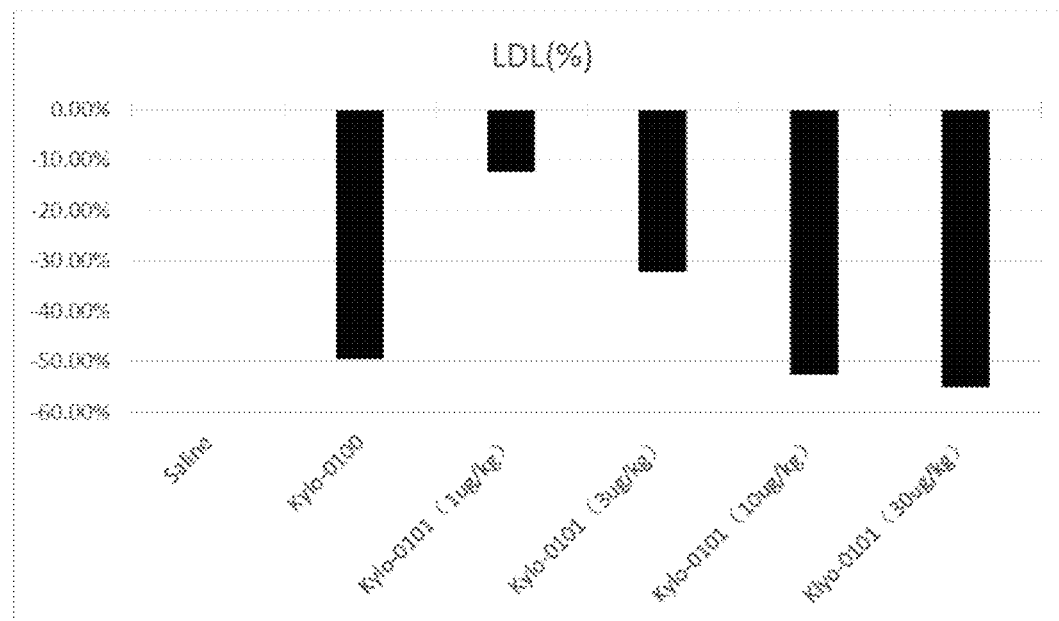
FIG. 10 shows effects of Kylo-0101 at different doses on LDL level in the serum of db/db mice in Example 5.

The experimental data in FIG. 10 shows that the LDL levels in the serum of the mice in the respective Kylo-0101 dose groups were reduced, and there was a significant dose-effect relationship. At a dose of 30 μg/kg, the LDL level in the serum was reduced by up to 58%.

Figure 11:
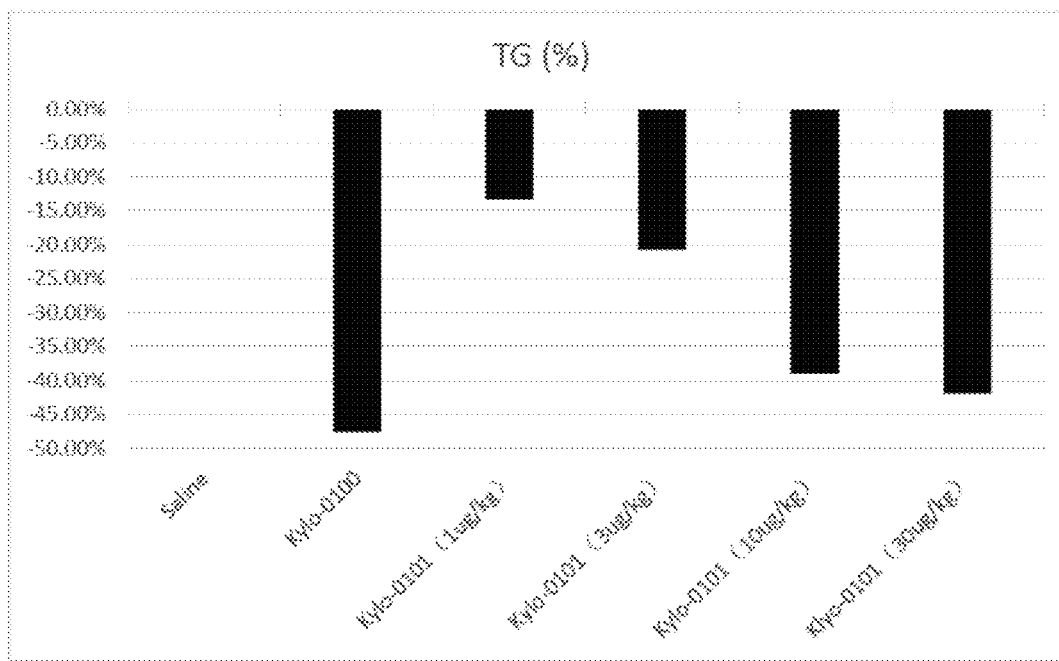
FIG. 11 shows effects of Kylo-0101 at different doses on TG level in the serum of db/db mice in Example 5.

The experimental data in FIG. 11 shows that the TG levels in the serum of the mice in the respective Kylo-0101 dose groups were reduced, and there was a significant dose-effect relationship. At a dose of 30 μg/kg, the TG level in the serum was reduced by up to 41.8%.

Figure 12:
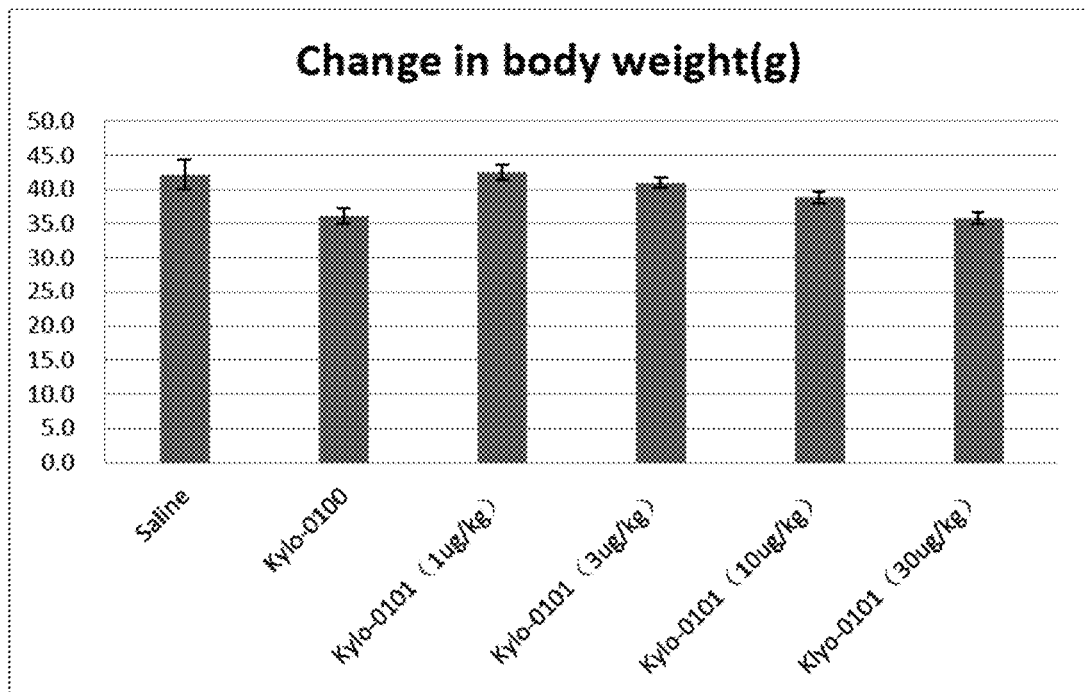
FIG. 12 shows effects of Kylo-0101 at different doses on body weight of db/db mice in Example 5.

The experimental data in FIG. 12 shows that the body weights of the mice in the respective Kylo-0101 dose groups were decreased, but not significantly.

Figure 13:
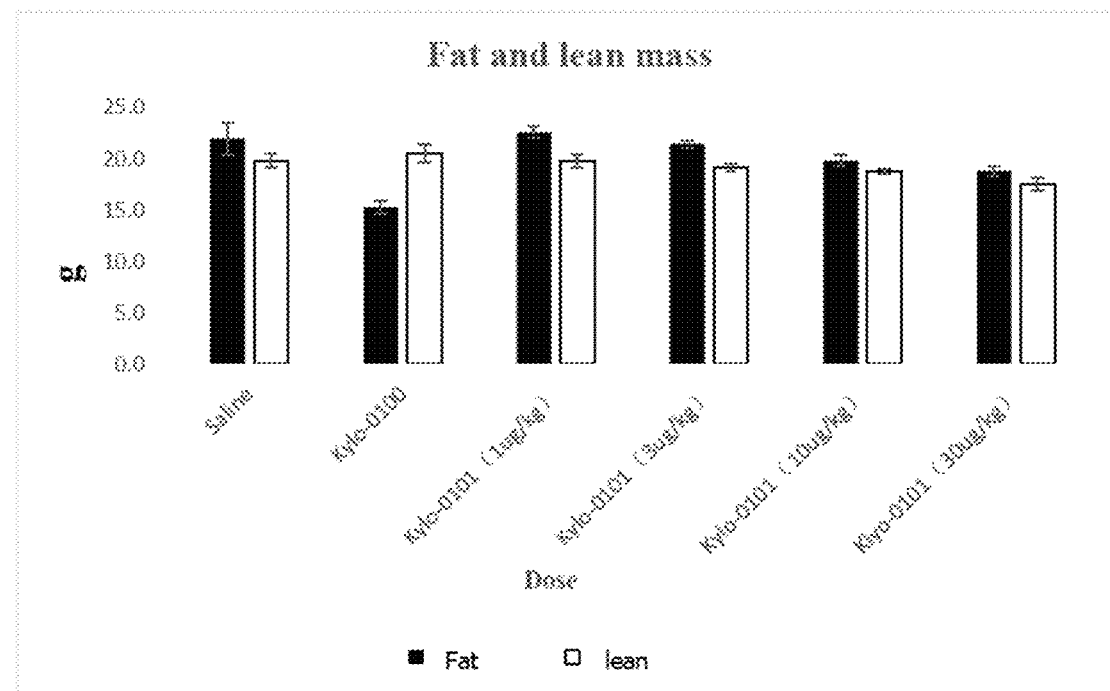
FIG. 13 shows effects of Kylo-0101 at different doses on fat and lean mass in db/db mice in Example 5.

The experimental data in FIG. 13 shows that each dose of Kylo-0101 did not significantly reduce the fat and lean mass in the body.

Figure 14:
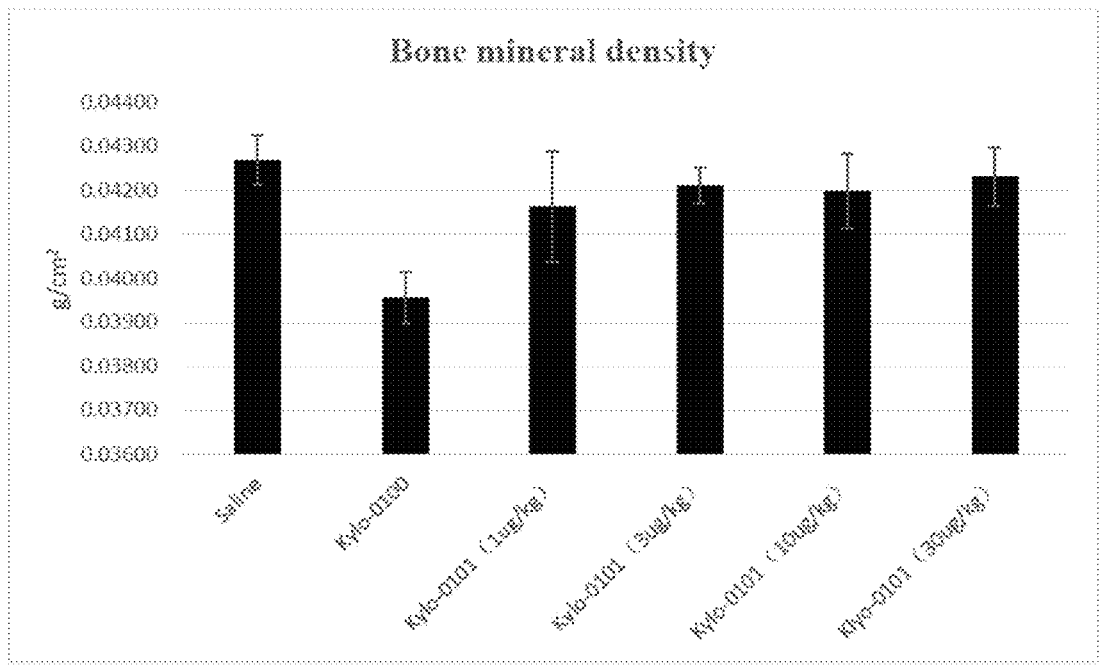
FIG. 14 shows effects of Kylo-0101 at different doses on bone mineral density of db/db mice in Example 5.

The experimental data in FIG. 14 shows that the bone mineral densities of the mice in the respective Kylo-0101 dose groups were basically unchanged compared with the model control group.

Figure 15:
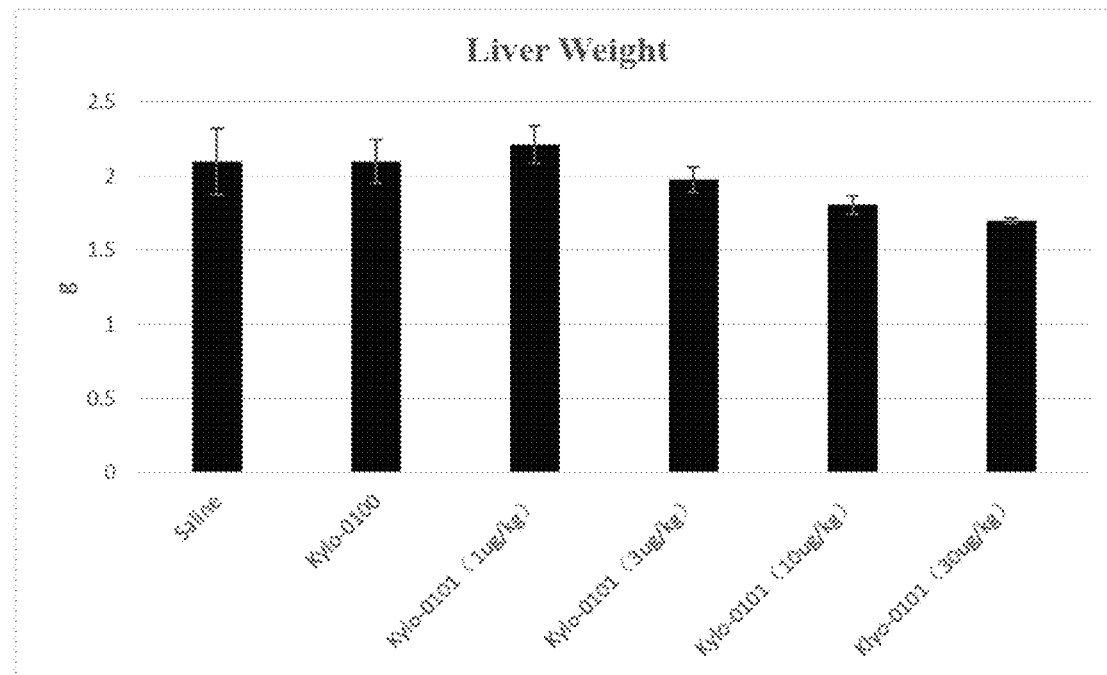
FIG. 15 shows effects of Kylo-0101 at different doses on liver weight of db/db mice in Example 5.

The experimental data in FIG. 15 shows that there was an obvious dose-effect relationship between the increase in the dose of Kylo-0101 and the decrease in the liver weight.

Figure 16:
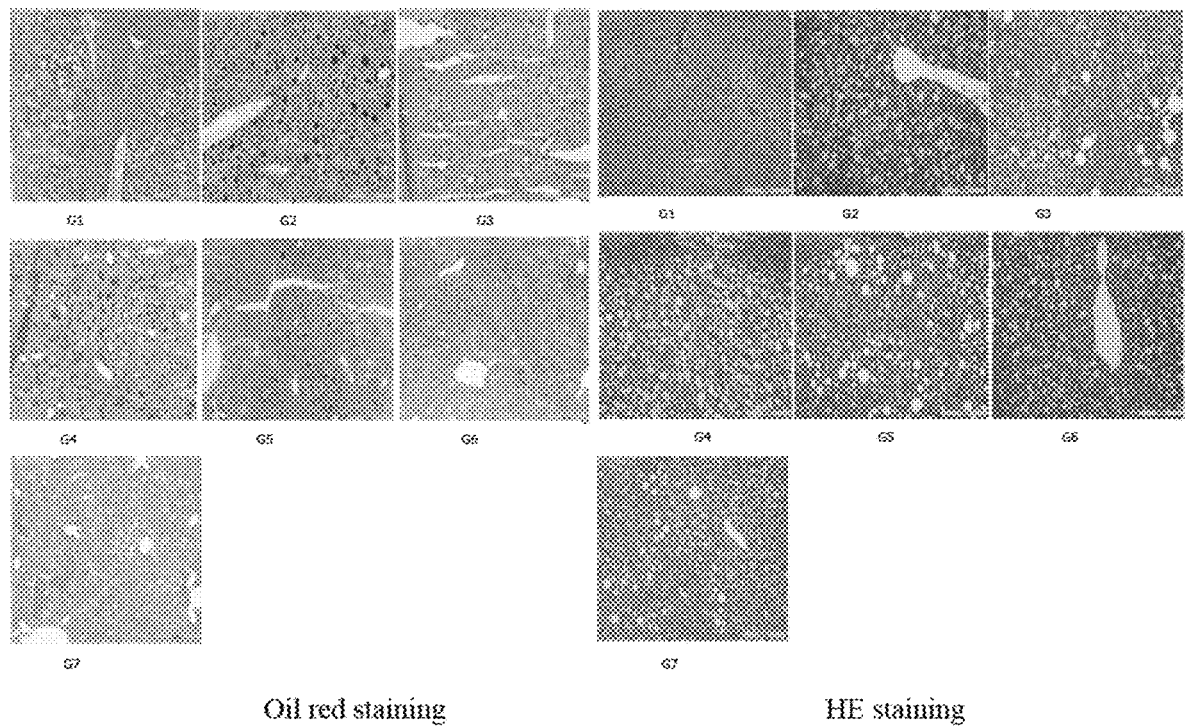
FIG. 16 shows histopathological pictures of oil red and HE stained liver slices in Example 5.

Oil red staining is mainly the specific staining of intracellular lipid droplets. The stained lipid droplets are shown as the dark spots in FIG. 16. The histopathological examination results of oil red staining show that, compared with the model control group, the four dose groups of Kylo-0101 showed significantly reduced positive staining degree of lipid droplets, significantly reduced number of lipid droplets, and a significant dose-effect response. Central fatty degeneration in liver lobules will form fatty vacuoles of varying sizes in the liver cells, of which small vacuoles are the main ones, and form light spots as shown in FIG. 16 after HE staining. In FIG. 16, the histopathological examination results of HE stained sections show that the four dose groups of Kylo-0101 showed hepatocyte steatosis degrees significantly lower than that of the model control group, significant reduced hepatocyte vacuoles caused by steatosis in the liver sections, and a significant dose-effect response.

Figure 17:
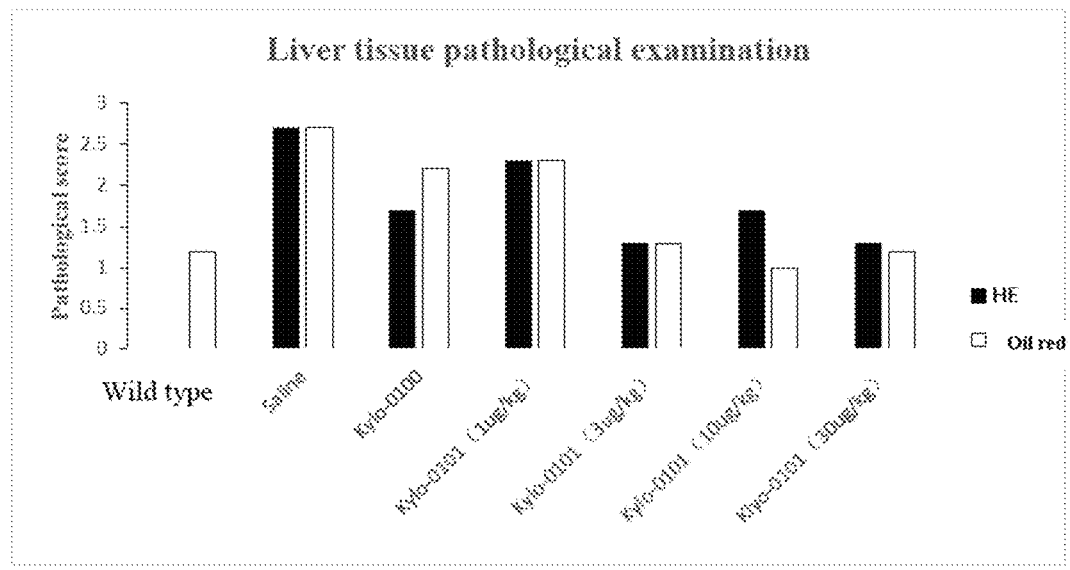
FIG. 17 shows average quantitative results of pathological examination of liver tissue by staining in Example 5.

The average quantitative results of the staining of liver pathological examination in FIG. 17 show that HE staining and oil red staining had a higher consistency, and when the dose of Kylo-0101 was 30 μg/kg, the fat content of the liver dropped to be almost close to that of normal (wild type) mice. It is generally considered that the normal average quantization value is less than 1 as normal.

Figure 18:
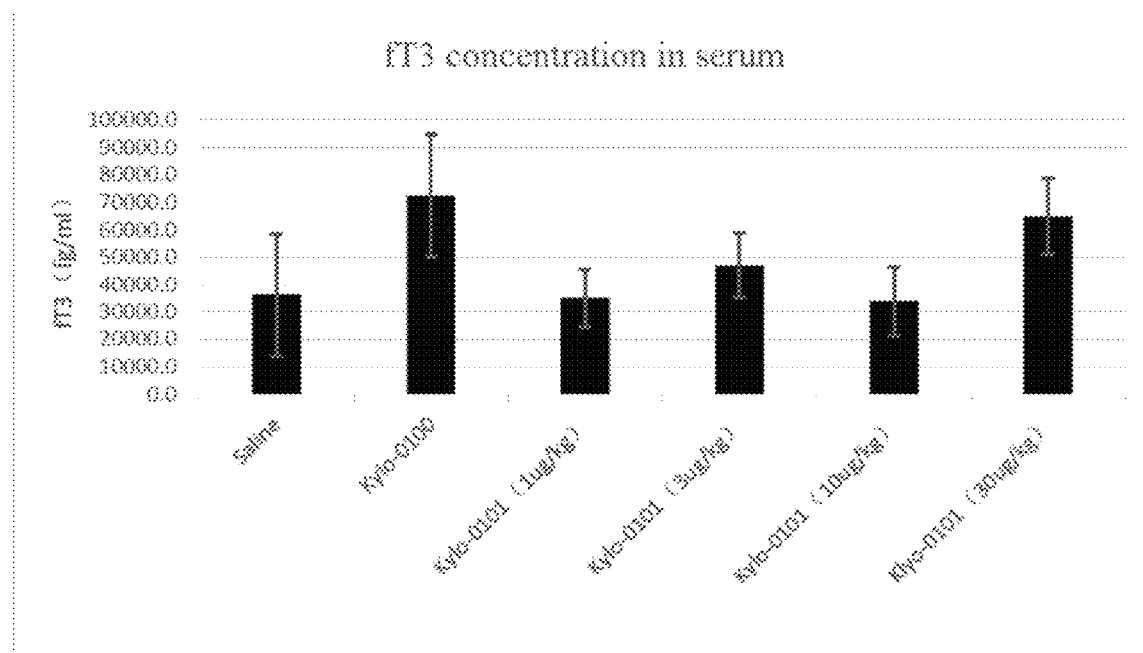
FIG. 18 shows effects of Kylo-0101 at different doses on fT3 concentration in the serum of db/db mice in Example 5.

The detection results in FIG. 18 show that at each dose of Kylo-0101, the fT3 concentration in the serum of mice was increased slightly, but there was no significant difference.

Figure 19:
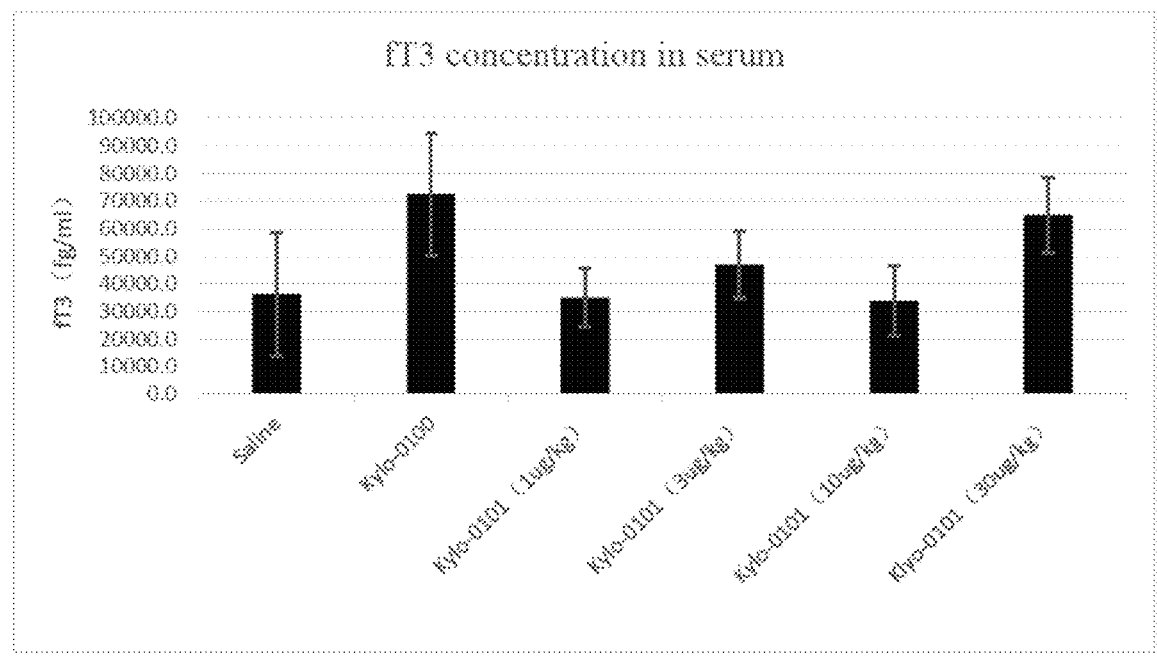
FIG. 19 shows effects of Kylo-0101 at different doses on TSH in the serum of db/db mice in Example 5.

The detection results in FIG. 19 show that each dose of Kylo-0101 had no effect on the TSH concentration in the serum of mice.

Example 6: Effect of the Targeting Specific Ligand X on the Binding Rate of the Drag with ASGPR, Heart Rate and Bone Mineral Density

TABLE 5

| No. | X | L | B |
|---|---|---|---|
| Kylo-0101 | [GalNAc sugar structure with NHAc] | [diamide linker with hexyl chain] | [pentaerythritol-like branching with NH] |
| Kylo-0105 | [sugar structure with NH, OH] | [diamide linker with hexyl chain] | [pentaerythritol-like branching with NH] |
| Kylo-0106 | [sugar structure with OH] | [diamide linker with hexyl chain] | [pentaerythritol-like branching with NH] |
| Kylo-0107 | [disaccharide structure with multiple OH] | [diamide linker with hexyl chain] | [pentaerythritol-like branching with NH] |

TABLE 5-continued
| No. | D | T | Binding rate with ASGPR | Heart rate | Bone mineral density |
|---|---|---|---|---|---|
| Kylo-0101 | 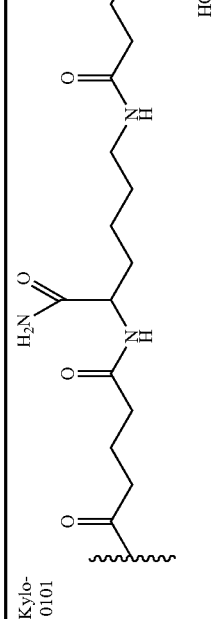 | 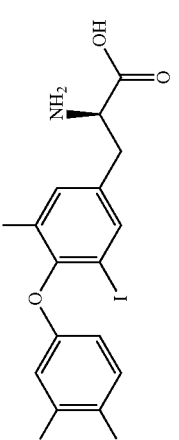 | 6 | 1 | 1 |
| Kylo-0105 | 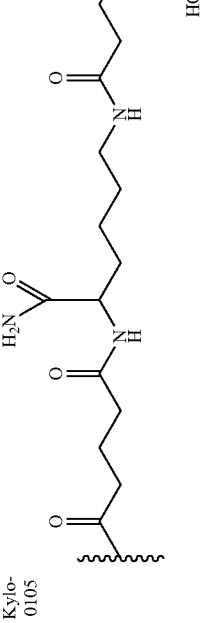 | 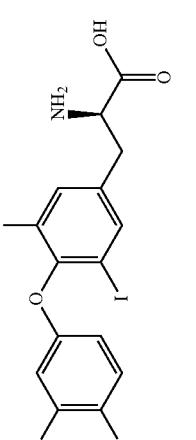 | 4 | 4 | 4 |
| Kylo-0106 | 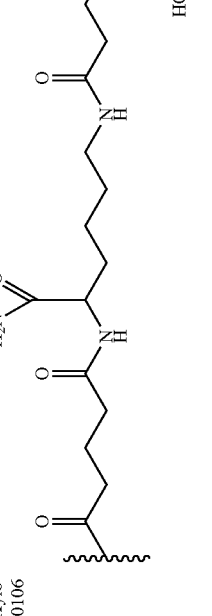 | 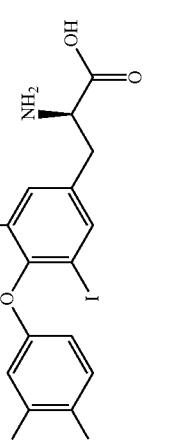 | 5 | 3 | 3 |
| Kylo-0107 | 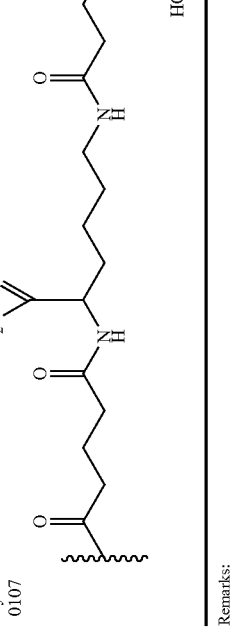 | 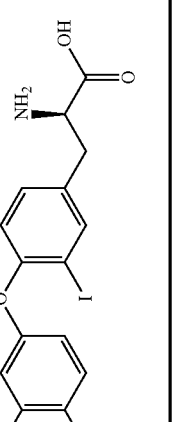 | 3 | 6 | 6 |
Remarks:
The numbers of 6 to 1 indicate that the binding rate of the drug formed by the combination with the asialoglycoprotein receptor ASGPR is from high to low; and the effect on cardiotoxicity and bone mineral density is from high to low.

The drags Kylo-0101 and Kylo-0105 to Kylo-0107 in Table 5 are only different in structure of X. The experimental data in the table shows that, in the case that the structures of L, B. D and T are the same respectively, the change in the structure of X would impart on the binding rate of the drag with ASGPR, heart rate and bone mineral density, wherein the drag Kylo-0101 has the best effect, it has a high binding rate to ASGPR and the least impact on heart rate and bone mineral density. This indicates that, in the composition prepared by the present invention, although the liver targeting specific ligand X is used to bind with ASGPR, it also has a certain impacted the whole therapeutic efficacy of the drug.

Example 7: Influence of the Branched Chain L Containing a Structure for Stabilizing Steric Hindrance on Drug Stability TABLE 6
| No. | X | L | B |
|---|---|---|---|
| Kylo-0101 | 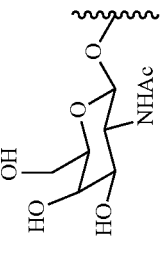 | 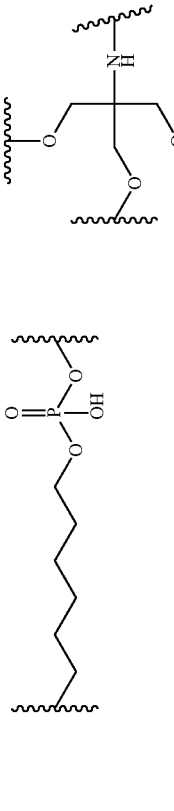 | 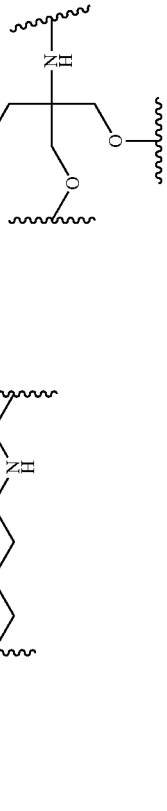 |
| Kylo-0108 | 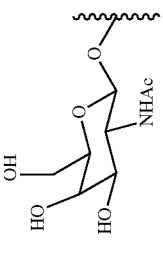 | 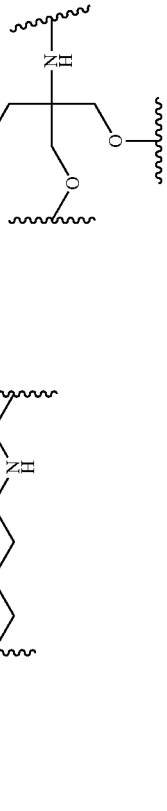 | 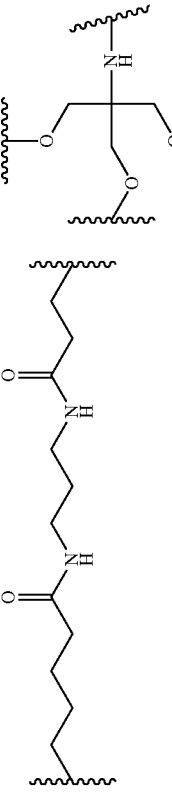 |
| Kylo-0109 | 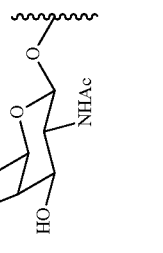 | 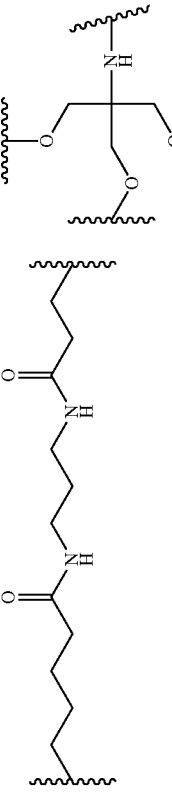 | 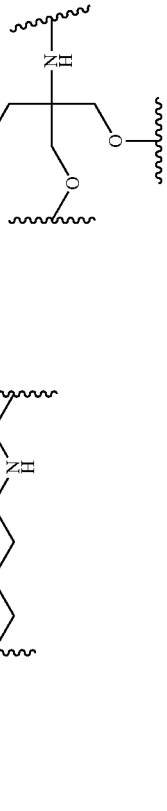 |
| Kylo-0110 | 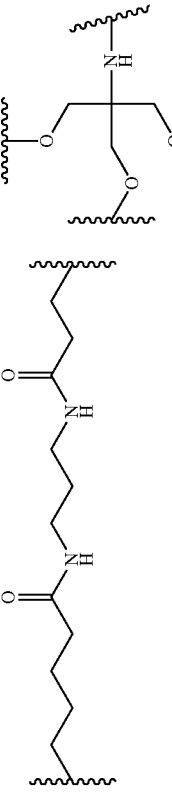 | 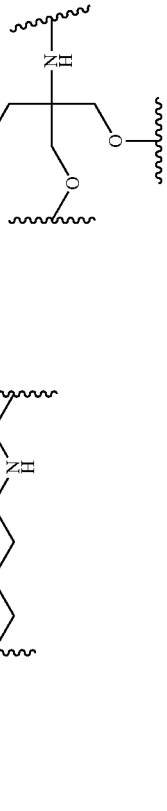 | 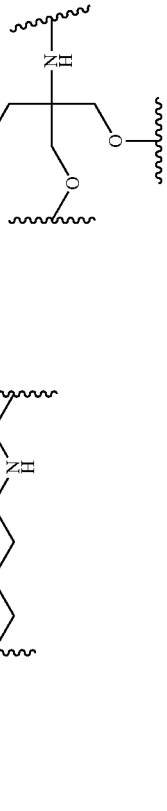 |

TABLE 6-continued
| Kylo-0115 | 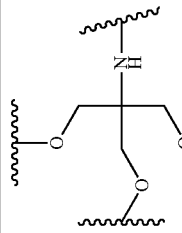 | 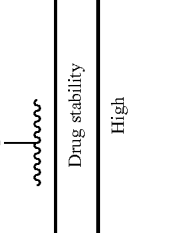 | 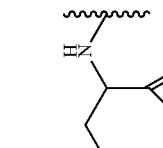 Drug stability |
|---|---|---|---|
| No. | D | T | Drug stability |
| Kylo-0101 | 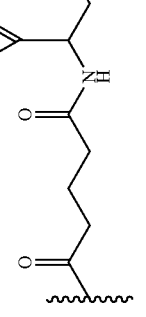 | 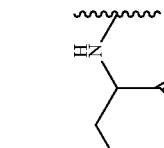 | High |
| Kylo-0108 | 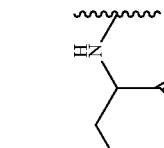 | 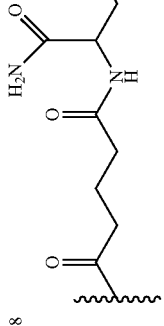 | Meddle |
| Kylo-0109 | 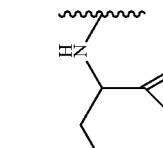 | 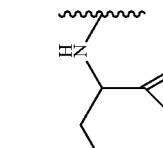 | Meddle |

TABLE 6-continued

| | | | |
|---|---|---|---|
| Kylo-0110 | [structure] | [T4-like structure] | High |
| Kylo-0115 | [structure] | [T4-like structure] | High |

The drugs Kylo-0101, Kylo-0108 to Kylo-0110, and Kylo-0115 in Table 6 at only different in structure of L. The experimental data in the table shows that, in the case that the tinctures of X, B, D and T are the same reflectively, the change in the structure of L would impact on the stability of the drug. When the L structures of Kylo-0101, Kylo-0110 and Kylo-0115 were selected, highly stable drugs could be obtained.

Example 8: Effect of the Linker B on the Binding Rate of the Drag with ASGPR, Heart Rate and Bone Mineral Density

TABLE 7

| No. | X | L | B |
|---|---|---|---|
| Kylo-0111 | | | |
| Kylo-0112 | | | |

TABLE 7-continued
| No. | D | T | Binding rate with ASGPR | Heart rate | Bone mineral density |
|---|---|---|---|---|---|
| Kylo-0113 | 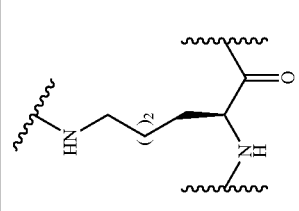 | 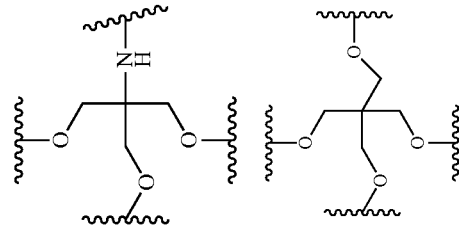 | 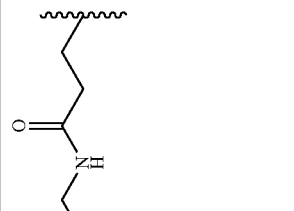 | | |
| Kylo-0101 | 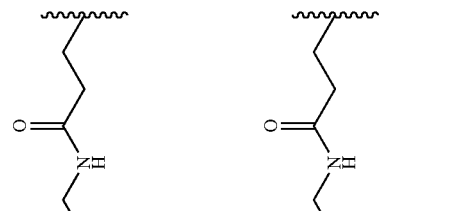 | 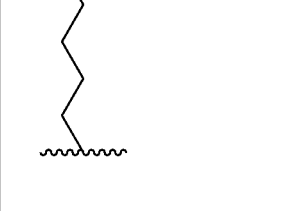 | 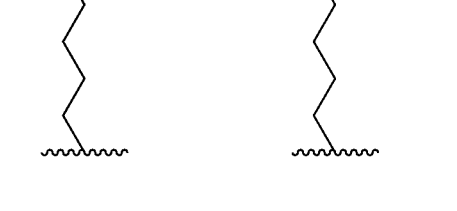 | 3 | 5 | 5 |
| Kylo-0116 | 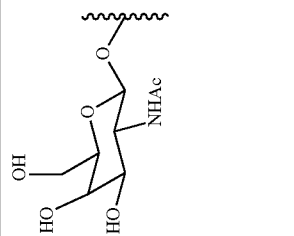 | 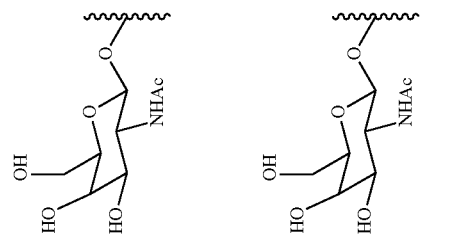 | | | |
| Kylo-0111 | | | | | |

TABLE 7-continued

| Compound | Structure | | | |
|---|---|---|---|---|
| Kylo-0112 | (structure) | 6 | 1 | 1 |
| Kylo-0113 | (structure) | 4 | 3 | 3 |
| Kylo-0101 | (structure) | 6 | 1 | 1 |
| Kylo-0116 | (structure) | 5 | 2 | 1 |

Remarks:
The numbers of 6 to 1 indicate that the binding rate of the drug formed by the combination with the asialoglycoprotein receptor ASGPR is from high to low; and the effect of cardiotoxicity and bone mineral density is from high to low.

The drugs Kylo-0101 and Kylo-0111 to Kylo-0113 in Table 7 are only different in fracture of B. The experimental data in the table shows that, in the case that the structures of X, L, D and T are the same respectively, the change in the structure of B would impact on the binding rate of the drug with ASGPR, heart rate and bone mineral density. When the B structures in Kylo-0101 and Kylo-0112 were selected, a good receptor binding rate and small side effects to heart and bone mineral density could be obtained.

Example 9: Effect of the Linking Chain D on the Hypolipidemic Ability of the Drug

TABLE 8

| No. | X | L | B |
|---|---|---|---|
| Kylo-0101 | (GalNAc sugar) | (diamide linker) | (tri-branched pentaerythritol-type) |
| Kylo-0102 | (GalNAc sugar) | (diamide linker) | (tri-branched pentaerythritol-type) |
| Kylo-0114 | (GalNAc sugar) | (diamide linker) | (tri-branched pentaerythritol-type) |

| No. | D | T | TC | LDL | TG |
|---|---|---|---|---|---|
| Kylo-0101 | (lysine-glutamic acid conjugate) | (thyroxine) | 6 | 6 | 6 |

TABLE 8-continued
| | | | | |
|---|---|---|---|---|
| Kylo-0102 | 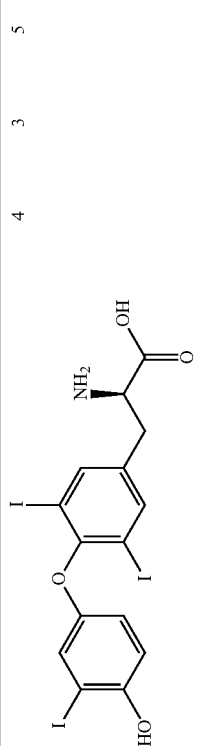 | 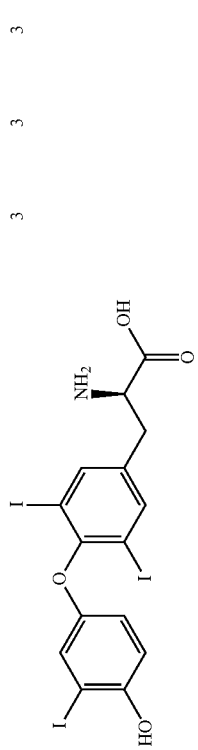 | 4 3 | 5 |
| Kylo-0114 | | | 3 3 | 3 |
Remarks:
The numbers under TC, LDL and TG represent the strength of the composition's ability to reduce TC, LDL and TG, respectively. The numbers of 6 to 1 indicate that the ability is from strong to weak.

The drugs Kylo-0101, Kylo-0102 and Kylo-0114 in Table 8 are only different in the structure of D. D alone as a linking structure does not have the hypolipidemic ability. However, the experimental data in the table indicates that, in the case that the structures of X, L, B, and T are the same respectively, the change m the structure of D would impact on the effects of lowing TC, TO and LDL of the drugs. Under the experimental conditions of the present invention, the D in the structure of the drag Kylo-0101 could achieve the best TC, TO and LDL lowering effect.

The invention claimed is:

1. A compound containing a liver targeting specific ligand and a thyroid hormone receptor agonist in the structure, wherein the liver targeting specific ligand X is connected to the thyroid hormone receptor agonist T sequentially through a branched chain L containing a structure for stabilizing steric hindrance, a linker B and a linking chain D, and the compound is represented by Formula (I) of

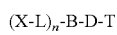

wherein n is 3, Formula (I) has a structure as shown below:

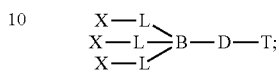

the compound has one of the structures shown in Kylo-0101 to Kylo-0103:

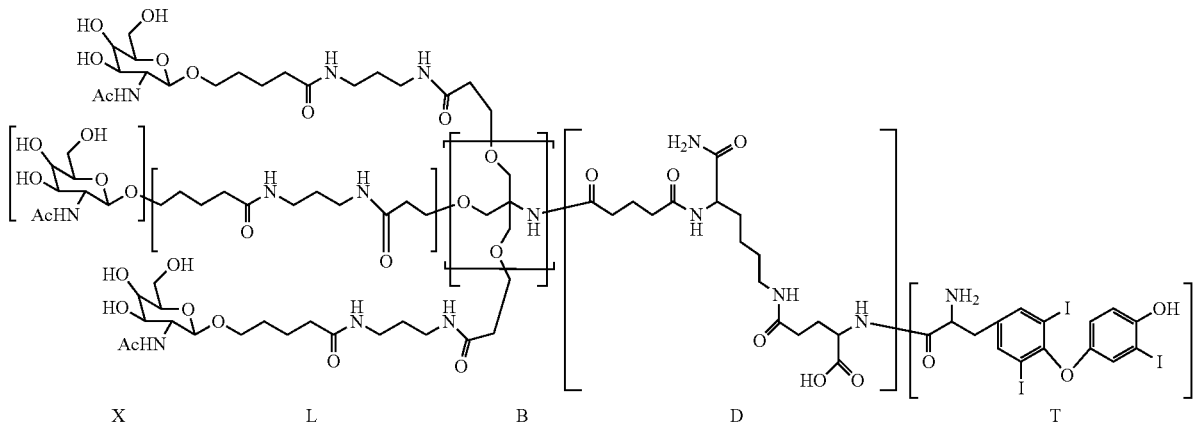

Kylo-0101

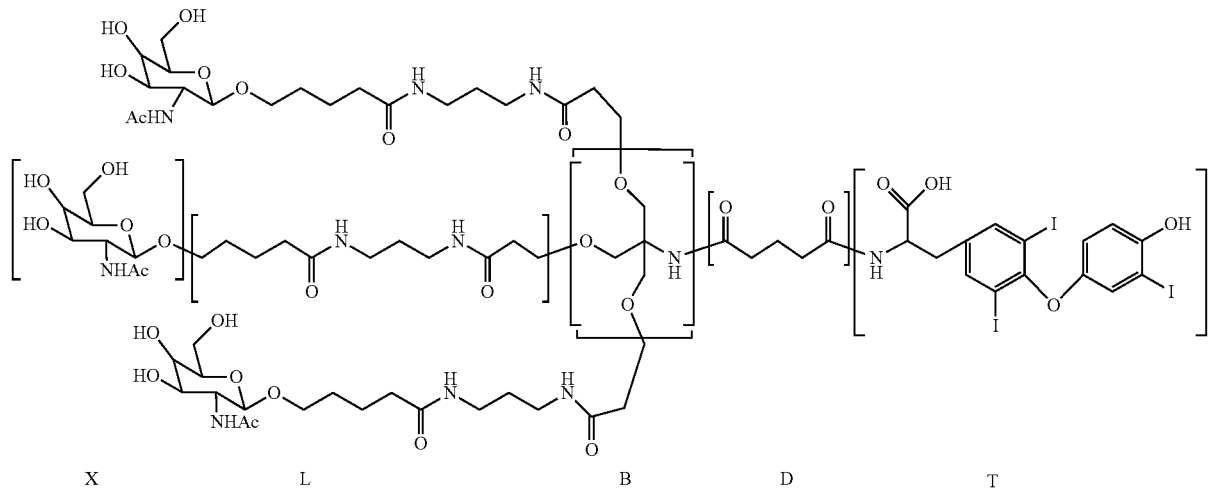

Kylo-0102

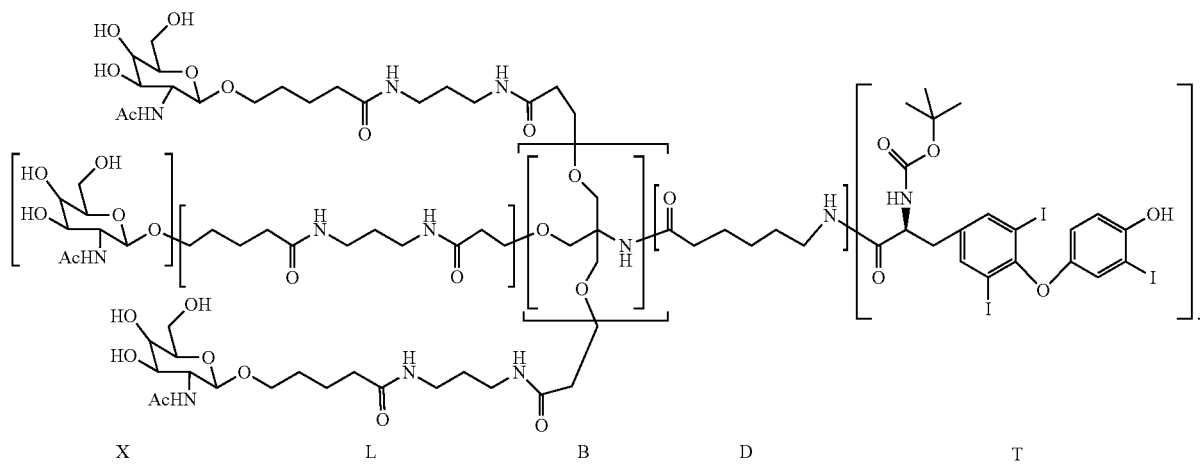

Kylo-0103

2. A pharmaceutical composition comprising the compound according to claim 1 and a pharmaceutically acceptable excipient.

3. The pharmaceutical composition according to claim 2, which is an injectable or oral preparation.

4. A method for treating a liver-derived disease wherein the liver-derived disease is non-alcoholic fatty liver or non-alcoholic steatohepatitis comprising administering a pharmaceutically acceptable amount of a compound of claim 1 to a subject in need thereof.

* * * * *